US007915008B2

(12) United States Patent
Larsen

(10) Patent No.: US 7,915,008 B2
(45) Date of Patent: Mar. 29, 2011

(54) METHODS FOR ISOLATION AND ANALYSIS OF SIALYLATED AND PHOSPHORYLATED PEPTIDES

(75) Inventor: Martin Rossel Larsen, Odense (DK)

(73) Assignee: Syddansk Universitet, Odense (DK)

( * ) Notice: Subject to any disclaimer, the term of this patent is extended or adjusted under 35 U.S.C. 154(b) by 803 days.

(21) Appl. No.: 11/741,055

(22) Filed: Apr. 27, 2007

(65) Prior Publication Data
US 2009/0029343 A1      Jan. 29, 2009

Related U.S. Application Data

(60) Provisional application No. 60/795,158, filed on Apr. 27, 2006, provisional application No. 60/802,509, filed on May 23, 2006.

(51) Int. Cl.
*C12P 21/06* (2006.01)
*C12Q 1/00* (2006.01)
*C07K 7/08* (2006.01)
*C07K 1/14* (2006.01)

(52) U.S. Cl. ............ 435/68.1; 435/4; 530/327; 530/344

(58) Field of Classification Search ........................ None
See application file for complete search history.

(56) References Cited

U.S. PATENT DOCUMENTS

2007/0227974 A1* 10/2007 Anders et al. ................. 210/638
2008/0261321 A1* 10/2008 Patton et al. .................. 436/104

FOREIGN PATENT DOCUMENTS

EP      1 428 878 A1      6/2004
EP      1 477 800 A1      11/2004

OTHER PUBLICATIONS

Stewart et al "18O Labeling:a tool for proteomics" Pub 2001 Rapid Commun. Mass Spectrom 15 pp. 2456-2465.*
Mirgorodskaya et al "Quantitation of peptides and proteins by matrix-assisted laser desorption /ionization mass spectrometry using 18O-labeled internal standards" Pub 2000 Rapid ommuications in Mass Spectrometry 14 pp. 1226-1232.*
Aparna H S et al , Isolation and Characterization of a Sialo-Glycopeptide from Buffalo Colostrum, Glycoconjugate Journal (1996) vol. 13: pp. 63-67, 1996 by Chapman & Hall.
Connor P A et al , Phosphate Adsorption onto TiO2 from Aqueous Solutions: An in Situ Internal Reflection Infrared Spectroscopic Study, Langmuir 1999, vol. 15, pp. 2916-2921, 1999 American Chemical Society, published on web Mar. 27, 1999.
Dobson K D et al., In Situ Infrared Spectroscopic Analysis of the Adsorption of Aromatic Carboxylic Acids to TiO2, ZrO2, Al2O3, and Ta2O5 from Aqueous Solutions, Spectrochimica Acta Part A vol. 56 (2000), pp. 557-565. 2000 by Elsevier Science B V , New Zealand.
Ficarro S et al , Phosphoproteome Analysis of Capacitated Human Sperm, The Journal of Biological Chemistry, vol. 278, No. 13, Issue of Mar. 28, pp. 11579-11589, 2003, by JBC Papers in Press, Dec. 30, 2002, Printed in U S A.

Figeys D et al , Electrophoresis Combined With Novel Mass Spectrometry Techniques: Powerful Tools for the Analysis of Proteins and Proteomes, Electrophoresis 1998, vol. 19. pp. 1811-1818, 1998 by Wiley-VCH Verlag GmbH, 69451 Weinheim.
Gruhler A et al , Quantitative Phosphoproteomics Applied to the Yeast Pheromone Signaling Pathway, Molecular & Cellular Proteomics 4 3, pp. 310-327, 2005 by The American Society for Biochemistry and Molecular Biology, Inc.
Irmak S et al., Stage-dependent Increase of Orosomucoid and Zinc-Alpha2-Glycoprotein in Urinary Bladder Cancer, Proteomics 2005, vol. 5, pp. 4296-4304, 2005 by Wiley-VCH Verlag GmbH & Co KGaA Weinheim.
Kweon H K et al , Selective Zirconium Dioxide-Based Enrichment of Phosphorylated Peptides for Mass Spectrometric Analysis, Analytical Chemistry, vol. 78, No. 6, Mar. 15, 2006, pp. 1743-1749.
Larsen M R et al , Highly Selective Enrichment of Phosphorylated Peptides from Peptide Mixtures Using Titanium Dioxide Microcolumns, Molecular & Cellular Proteomics 4 7, pp. 873-886, 2005 by the American Society for Biochemistry and Molecular Biology, Inc.
Li S et al , Iron(III)-Immobilized Metal Ion Affinity Chromatography and Mass Spectrometry for the Purification and Characterization of Synthetic Phosphopeptides, Analytical Biochemistry vol. 270, pp. 9-14 (1999), Article ID abio 1999 4060 , 1999 by Academic Press.

(Continued)

*Primary Examiner* — Herbert J. Lilling
(74) *Attorney, Agent, or Firm* — Birch, Stewart, Kolasch & Birch, LLP

(57) ABSTRACT

Changes in sialylation of cell surface or plasma proteins are often associated with various cancers and other disease conditions. Provided are methods of detecting biomarkers of conditions associated with a change of sialylation status. Sialylated peptides are first isolated from biological and other samples by loading onto titanium dioxide (TiO2) or zirconium dioxide (ZrO2) stationary phase under acidic conditions in a solution comprising at least 20% organic phase and at least about 6.5 mM of substituted aromatic carboxylic acid, or, alternatively, at least about 11 mM short chain, non-aromatic, hydroxylated carboxylic acid. Sialic acid containing proteins can then be eluted from loaded stationary phase material by exposure to an alkaline solution having pH of 9.0 or greater, preferably at least 10.5. Sialylated peptides isolated by the methods provided can then be analysed by mass spectrometry to identify patterns of sialylation across a sialiome (the entire complement of sialic acid containing peptides in a biological sample) and/or to identify proteins in a sample that are sialylated or that show changes in sialylation status between two or more different samples. In preferred embodiments, sialylated peptides from control and patient samples can be differentially isotopically labelled and compared in a single mass sprectrometry experiment. Also provided are specific biomarkers of bladder cancer. The methods for isolating and analysing sialylated proteins can also by applied to phosphorylated proteins.

25 Claims, 43 Drawing Sheets

OTHER PUBLICATIONS

Neville DCA et al, Evidence for Phosphorylation of Serine 753 in CFTR Using a Novel Metal-Ion Affinity Resin and Matrix-assisted Laser Desorption Mass Spectrometry, Protein Science 1997 vol. 6, pp. 2436-2445, 1997 by Cold Spring Harbor Laboratory Press.

Nühse T S et al, Large-scale Analysis of in Vivo Phosphorylated Membrane Proteins by Immobilized Metal Ion Affinity Chromatography and Mass Spectrometry, Molecular & Cellular Proteomics vol. 2 11, pp. 1234-1243, 2003 by American Society for Biochemistry and Molecular Biology, Inc.

Pal S et al, Purification and Characterization of 9-O-acetylated Siaioglycoproteins from Leukemic Cells and Their Potential as Immunological Tool for Monitoring Childhood Acute Lymphoblastic Leukemia, Glycobiology vol. 14, No. 10, 2004, pp. 859-870, by Advance Access Publication on Jun. 9, 2004.

Pinkse M W H et al, Selective Isolation at the Femtomole Level of Phosphopeptides from Proteolytic Digests Using 2D-NanoLC-ESI-MS/MS and Titanium Oxide Precolumns. Analytical Chemistry, vol. 76, No. 14, Jul. 15, 2004, pp. 3935-3943, 2004 by American Chemical Society.

Posewitz M C et al., Immobilized Gallium(III) Affinity Chromatography of Phosphopeptides, Analytical Chemistry, vol. 71, No. 14, Jul. 15, 1999, pp. 2883-2892, 1999 by American Chemical Society.

Rinal Ducci S. et al, Novel Protein Phosphorylation Site Identification in Spinach Stroma Membranes by Titanium Dioxide Microcolumns and Tandem Mass Spectrometry, Journal of Proteome Research 2006, vol. 5, pp. 973-982, 2006 by American Chemical Society.

Treuheit M J et al, Analysis of the Five Glycosylation Sites of Human Alpha1-acid Glycoprotein, Biochem J (1992), vol. 283, pp. 105-112, Printed in Great Britain.

\* cited by examiner

**(P14151) L-selectin
IGGIWTWVGTNK**

**(Q13201) Multimerin-1
FNPGAESVVLSNSTLK**

METHODS FOR ISOLATION AND ANALYSIS OF SIALYLATED AND PHOSPHORYLATED PEPTIDES

REFERENCE TO RELATED APPLICATIONS

The present application claims benefit of priority to U.S. Provisional applications Nos. U.S. 60/795,158, filed on Apr. 27, 2006, and 60/802,509, filed on May 23, 2006, the entire contents of which are incorporated by reference herein.

FIELD OF THE INVENTION

The present invention relates in general to methods for isolating and analyzing sialylated and phosphorylated peptides. More particularly, the invention relates to methods of identifying biomarkers of conditions associated with a change of protein sialylation status and to methods for derivatizing phosphorylated peptides while loaded onto stationary phase.

BACKGROUND OF THE INVENTION

Abnormal glycosylation is a well known attribute of cancer cells. (1-4) A number of specific glycan structures serve as biomarkers of tumor growth. Of particular significance are the sialic acids, of which more than 40 naturally occurring derivatives have been identified. Sialic acids are nine-carbon carboxylated sugars which exist in three primary forms. The most common is N-acetyl-neuraminic acid (2-keto-5-acetamido-3,5-dideoxy-D-glyc-ero-D-galactononulopyranos-1-onic acid (often abbreviated as NeuSAc, NeuAc, or NANA). A second common form is N-glycolyl-neuraminic acid (Neu5Gc or NeuGc), in which the N-acetyl group of NeuAc is hydroxylated. A third primary sialic acid is 2-keto-3-deoxy-nonulosonic acid (KDN).

Typically found at the reducing end of glycans attached to cell surfaces or plasma proteins, sialic acids are typically over expressed in tumor cells, relative to normal tissues. These terminal sialic acids are involved in cellular adhesion and are components of cell surface receptors. Excess sialylation may mask specific cellular recognition sites, which is an important component of physiological responses to cancer cells. Lewis X and Lewis A blood group antigens, which are sialic acid containing proteins, are also typically overexpressed in carcinomas. Additional qualitative and quantitative changes in tumor cell surface sialic acids are associated with progression to malignancy. Tumor cells can change the sialo-glyco-conjugates expressed on their plasma membranes, which affects their ability to invade. (5-16) Quantitative and qualitative assessment of protein sialylation in biological samples is increasingly recognized as a valuable contribution to diagnosis, prognosis and monitoring of conditions associated with over-sialylation of proteins. Such conditions include diabetes and myeloma, epithelial, breast, ovarian, oral, gastrointestinal, prostate, endometrial, lung, colon, pancreatic, and thyroid cancers. Assessments of protein sialylation are also useful in diagnosis, prognosis and monitoring of conditions associated with under-sialylation of proteins, including HIV-1 infection, cystic fibrosis, hereditary inclusion body myopathy (HIBM), Henoch-Schonlein purpura, and IgA nephropathy. (17-27)

Changes in sialylation status associated with disease conditions often involve low abundance proteins. Accordingly, an initial purification of sialic acid containing proteins is required for analysis of sialylation status. Methods for isolation of sialylated proteins thus provide means of qualitative and quantitative assessment of sialylation status as well as means of identifying specific biomarkers of conditions associated with a change of sialylation status. A variety of techniques for purification of sialylated proteins have been reported. WO2005/107491 teaches a lectin affinity chromatography. EP 1 428 878 teaches an anion exchange method. JP 08027181 teaches use of a chitosan-immobilized stationary phase. A variety of HPLC and hydrophilic interaction chromatography techniques have also been reported. These techniques generally require expensive reagents or relatively cumbersome procedures or utilize buffers that are not suited for mass spectrometry studies.

Accordingly, the present invention provides a simple, convenient method for isolation of sialylated peptides that is particularly suited for mass spectrometry analysis. The method generally utilizes titanium dioxide or zirconium dioxide chromatographic stationary phase material and a loading buffer comprising a substituted aromatic carboxylic acid, preferably dihydroxy benzoate or phthalic acid. The invention further provides methods of identifying biomarkers of a condition associated with change of sialylation status as well as methods for diagnosing, prognosing or monitoring such conditions. In other embodiments, the method is also useful for isolation and analysis of phosphorylated peptides.

SUMMARY OF THE INVENTION

One aspect of the present invention provides a method for isolation of sialylated peptides from biological and other samples. A sample is loaded onto titanium dioxide (TiO2) or zirconium dioxide (ZrO2) stationary phase under acidic conditions in a solution comprising at least 20% organic phase and at least about 6.5 mM of substituted aromatic carboxylic acid, preferably dihydroxy benzoate or phthalic acid, or, alternatively, at least about 11 mM short chain, non-aromatic, hydroxylated carboxylic acid, preferably lactic acid, glycolic acid, beta-hydroxy proprionic acid, or citric acid. Optionally, the loaded stationary phase material may be washed with the same solution. Sialic acid containing proteins can then be eluted from loaded stationary phase material by exposure to an alkaline solution having pH of 9.0 or greater, preferably at least 10.5.

In another aspect, the invention provides a method for analysing sialylated peptides by combining isolation of sialylated peptides with mass spectrometry. Sialylated peptides are isolated by the method of the present invention and then analysed by mass spectrometry to identify patterns of sialylation across a sialiome (the entire complement of sialic acid containing peptides in a biological sample) and/or to identify proteins in a sample that are sialylated or that show changes in sialylation status between two or more different samples.

In a preferred embodiment, proteins from a biological or other sample are cleaved into smaller peptide fragments prior to isolation of sialylated peptides and mass spectrometry analysis. For example, the isolated sialylated proteins can be subject to enzymatic hydrolysis to produce peptide fragments. In one preferred embodiment, the isolated sialylated proteins are fragmented by treatment with trypsin, which cleaves at LYS and ARG residues.

In another preferred embodiment, proteins from a biological or other sample are mass-modified with isotopic labels prior to isolation of sialylated peptides and mass spectrometry analysis. Isotopic modification may, optionally, be done before, after or during enzymatic hydrolysis of proteins in a biological or other sample. For example, to facilitate comparisons of changes in sialylation state between two different samples, trypsin digestion can be undertaken in buffers containing either ordinary water, as control, or $O^{18}$-labelled water, for comparison. This produces mass-modified peptides in a comparison sample that can be conveniently and easily compared in a single mass spectrometry experiment with corresponding peptides in control samples.

In still another aspect, the invention provides a method for identifying biomarkers of conditions associated with change of sialylation status by combining isolation of sialylated peptides with mass spectrometry. Sialylated peptides are isolated by the method of the present invention from samples taken from ordinary healthy persons, as controls, and from patients suffering from a condition associated with change of sialylation status, for comparison. Any suitable sample may be used for comparison. The control and patient samples are then compared to identify specific proteins that exhibit a change of sialylation status.

In one preferred embodiment, proteins from control and patient samples are subject to enzymatic hydrolysis with trypsin in a buffer comprising unlabelled water. The control and patient samples are then subject to re-hydrolysis with trypsin, wherein ordinary samples are re-hydrolysed in a buffer comprising unlabelled water, while patient samples are re-hydrolysed in a buffer comprising $O^{18}$-labelled water. The sialylated tryptic peptides from control and patient samples can then be isolated according to the methods of the present invention and compared in a single mass spectrometry experiment. Because of a 4 atomic unit mass offset in $O^{18}$-labelled compared with unlabelled peptides, sialylated peptides in patient samples can be readily identified which exhibit a change of sialylation status relative to corresponding peptides in control samples. Each of these differently-sialylated peptides is a candidate biomarker for the condition from which the patient was suffering. Candidate biomarkers can then be validated by comparison with samples from additional patients suffering from the same condition.

A variety of mass spectrometry techniques can be used to characterize candidate biomarker peptides. In certain preferred embodiments, the isolated sialylated peptides are identified from analysis using tandem mass spectroscopy techniques, such as LC/MS/MS (Liquid Chromatography tandem Mass Spectrometry). The molecular weight of a fragment, as determined from the mass spectrometry data, can be used to identify possible matches in databases indexed by predicted molecular weights of protein fragments which would result under similar conditions as those generated in the subject method. However, the subject method can also be carried out using mass spectrometry techniques which produce amino acid sequence mass spectra for the isolated sialylated peptides. The sequence data can be used to search one or more sequence databases well known in the art.

The invention further provides a method for isolation of phosphorylated peptides from biological and other samples. A sample is loaded onto titanium dioxide (TiO2) or zirconium dioxide (ZrO2) stationary phase under acidic conditions in a solution comprising at least 20% organic phase and at least about 6.5 mM of substituted aromatic carboxylic acid, preferably dihydroxy benzoate or phthalic acid. Optionally, the loaded stationary phase material may be washed with the same solution. Phosphorylated peptides can then be eluted from loaded stationary phase material by exposure to an alkaline solution having pH of 9.0 or greater, preferably at least 10.5.

The invention further provides a method for analysing phosphorylated proteins by combining isolation of phosphorylated peptides with mass spectrometry. Phosphorylated proteins are loaded onto titanium dioxide (TiO2) or zirconium dioxide (ZrO2) stationary phase by the method of the present invention and then derivatised with one or more selective detection groups while immobilised on the stationary phase. Derivatised peptides are then eluted by exposure to an alkaline solution having pH of 9.0 greater and analysed by mass spectroscopy to identify patterns of phosphorylation across a proteome and/or to identify proteins in a sample that are phosphorylated or that show changes in phosphorylation state between two or more different samples.

Additional objects and advantages of the present invention will be apparent from the detailed description that follows.

DETAILED DESCRIPTION OF THE PREFERRED EMBODIMENTS

Figure 1:
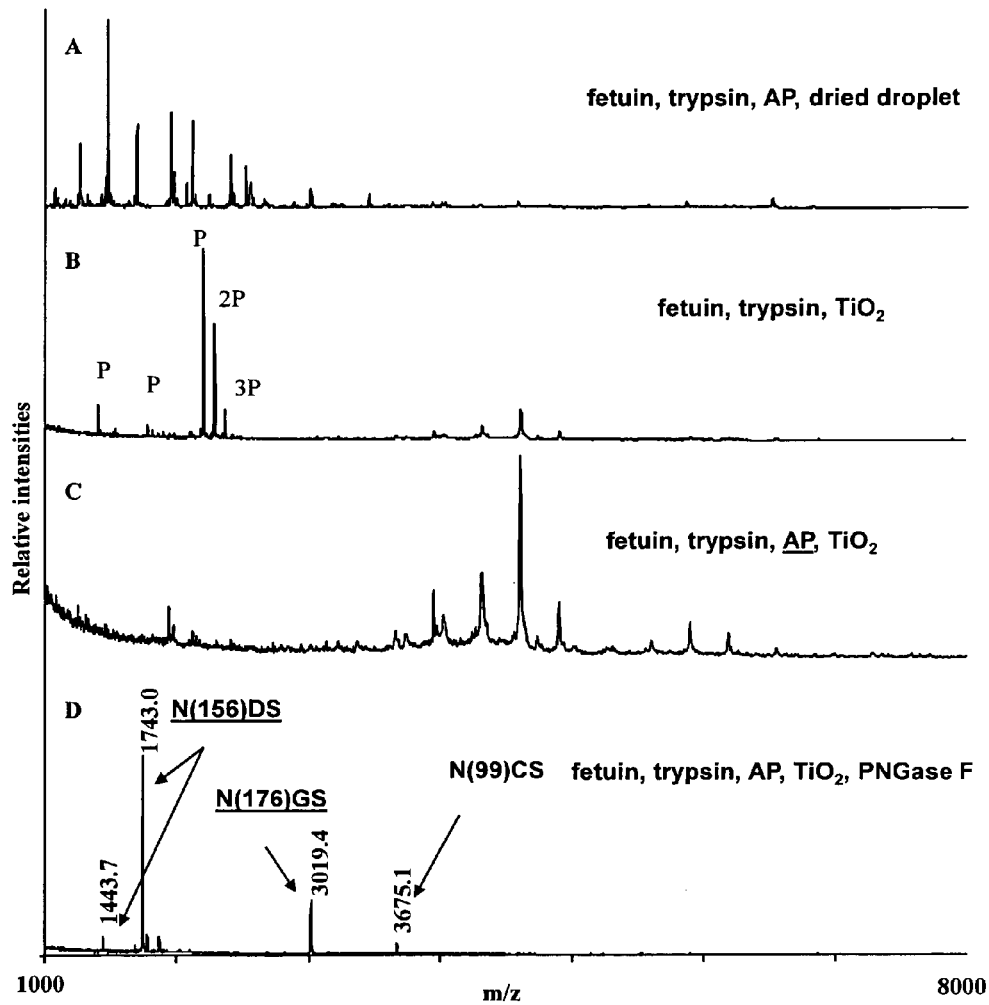
FIG. 1A shows MALDI mass spectra of feutin and its tryptic fragments in a tryptic peptide mixture.
FIG. 1B shows MALDI mass spectra of feutin and its tryptic fragments in a tryptic peptide mixture eluted off a $TiO_2$ column.
FIG. 1C shows MALDI mass spectra of feutin and its tryptic fragments in a tryptic peptide mixture treated with alkaline phosphatase and subsequently eluted off a $TiO_2$ column.
FIG. 1D shows MALDI mass spectra of feutin and its tryptic fragments in a tryptic peptide mixture treated with N-glycosidase F subsequently eluted off a $TiO_2$ column.

As used herein, the following terms have the following meanings:

"Acidic" refers to a pH of 3.0 or less.

"Container" refers to means for enclosing or otherwise supporting a volume of chromatographic stationary phase material so as to permit contact with solutions. The term "container" encompasses a surface coated with chromatographic stationary phase material.

"Eluting" refers to the process of removing an adsorbed sample from chromatorgraphic stationary phase material.

"Glycan heterogeneity" refers to variability of glysoyl moieties and/or glycosidic linkages associated with a glycosyated protein.

"Isolated" refers to one component of a mixture that has been enriched over other components of the mixture. "Isolated sialylated peptides" are sialylated peptides that have been enriched from a mixture that initially included non-sialylated peptides and/or other components.

"Loading" refers to the process of contacting a sample with chromatographic stationary phase material.

"Obtained" as used in the phrase "wherein the solution is obtained from" may include any process of purification, derivitization, concentration, digestion, labelling and/or other treatment of a sample.

"Organic phase" refers to one more carbon-containing solvent components of a liquid chromatography solution other than an additive which could be termed a "substituted aromatic carboxylic acid"

"Patient" refers to human or animal subjects (animals being particularly useful as models for clinical efficacy of a particular composition).

"Peptide" refers to an amino acid polymer, or poly amino acid, or polypeptide of any length greater than two amino acid residues.

"Phosphorylated" refers to covalent modification by one or more phosphate groups "Protein" refers to an amino acid polymer, or poly amino acid, or polypeptide of any length greater than two amino acid residues.

"Sample" refers to any protein-containing material. Samples may be obtained from humans, cultured cells, or other sources and may comprise tissues or bodily fluids. The term "sample" encompasses both an initial cell culture aliquot, tissue biopsy, fluid sample, or other source of proteins as well as the product of any manipulation of the initial source of proteins, including but not limited to partial purification, enzyme digestion, or other treatment.

"Short chain, non-aromatic, hydroxylated carboxylic acid" refers to any carboxylic acid having more than 2 but fewer than 16 carbons, which is hydroxylated at one or more positions, and which may contain any number of unsaturations or branching points. Di- and tri-carboxylic acids are "hydroxylated" within the meaning of "short chain, non-aromatic, hydroxylated carboxylic acid." The term as used may include one or more different species. When a concentration of "short chain, non-aromatic, hydroxylated carboxylic acid" is expressed, the term is additive across one or more different species. Concentrations can be expressed in mM terms. For example, the molecular weight of lactic acid is 90.8 daltons. Concentrations of lactic acid of about 1 mg/ml accordingly constitute solutions of about 11 mM.

"Sialic acid" refers to any member of a family of nine-carbon carboxylated sugars. Also included are sialic acid analogues that are derivatized with linkers, reactive functional groups, detectable labels and targeting moieties. The most common member of the sialic acid family is N-acetyl-neuraminic acid (2-keto-5-acetamido-3,5-dideoxy-D-glycero-D-galactononulopyranos-1-onic acid (often abbreviated as NeuSAc, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261: 11550-11557; Kanamori et al., J. Biol. Chem. 265: 21811-21819 (1990)). Also included are 9-substituted sialic acids such as a 9-O—C.sub.1-C.sub.6 acyl-Neu5Ac like 9-O-lactyl-Neu5Ac or 9-O-acetyl-NeuSAc, 9-deoxy-9-fluoro-Neu5Ac and 9-azido-9-deoxy-Neu5Ac. For review of the sialic acid family, see, e.g., Varld, Glycobiology 2: 25-40 (1992); Sialic Acids: Chemistry, Metabolism and Function, R. Schauer, Ed. (Springer-Verlag, New York (1992)).

"Sialylated" refers to covalent modification by one or more sialic acid moities

"Sialylation status" refers to both the quantitative amount of sialic acid moieties associated with a protein glycosylation site and also to the qualitative nature of glycosidic linkages in sialic acid containing glycosyl moities and also to the nature and extent of any modifications of sialic acid moieties including but not limited to acetylation.

"Substituted aromatic carboxylic acid" refers to a carboxylic acid comprising one or more aromatic rings at least one of which rings which bears one or more substituent groups. The term as used may include one or more different species. When a concentration of "substituted aromatic carboxylic acid" is expressed, the term is additive across one or more different species. Concentrations can be expressed in mM terms. For example, the molecular weight of 2,5-dihydroxybenzoic acid is 154.12 daltons. Concentrations of DHB of about 1 mg/ml accordingly constitute solutions of about 6.5 mM.

"Titanium dioxide stationary phase" refers to any chromatographic stationary phase material in which the interacting surface is comprised primarily of titanium dioxide, either as free spheres, as a surface coating of other material or in any other form suitable for use in liquid chromatography. The phrase "titanium dioxide or zirconium dioxide stationary phase" encompasses any combination of titanium dioxide and zirconium dioxide. The term "liquid chromatography" encompasses use of "titanium dioxide stationary phase" as an affinity adsorbent surface, for example, in microtitre plates formatted for multiple sample analysis.

"Zirconium dioxide stationary phase" refers to any chromatographic stationary phase in which the interacting surface is comprised primarily of zirconium dioxide, either as free spheres, as a surface coating of other material or in any other form suitable for use in liquid chromatography. The phrase "titanium dioxide or zirconium dioxide stationary phase" encompasses any combination of titanium dioxide and zirconium dioxide. The term "liquid chromatography" encompasses use of "zirconium dioxide stationary phase" as an affinity adsorbent surface, for example, in microtitre plates formatted for multiple sample analysis.

Isolation of Sialylated Peptides Using Titanium Dioxide or Zirconium Dioxide Stationary Phase and a Buffer Comprising a Substituted Aromatic Carboxylic Acid.

Protein containing samples from which sialylated peptides are isolated according to the method of the invention may be obtained from any desired organism. For example, the sample may be obtained from bacteria, yeast, worms, amphibia, fish, plants, parasites, insects, or mammals. In a preferred embodiment, the organism is a mammal. In another preferred embodiment, the mammal is a human. The method can be applied to one or more samples from one or more cell types or fluid samples derived from any organism. Fluid samples may be bodily fluids, such as serum, urine, spinal fluid, or synovial fluid. Blood samples may also be employed, whether cells, e.g. erythrocytes, are first removed or not. In a preferred embodiment, the fluid sample is human plasma.

In other embodiments, methods of the present invention may be employed with non-biological samples.

Samples may also be obtained directly from tissues. In a preferred embodiment, the tissue sample is a biopsy sample. These small pieces of living tissue, typically weighing less than 500 milligrams, are taken directly from an organism and used directly without growth in tissue culture. The use of such living tissue allows direct analysis of the biological state of the tissue without introducing artifacts that may arise as a consequence of growth in culture. Any desired cell type from a given organism may be utilized. For example, tumor cells (e.g. from breast, prostate, etc.) may be cultured or obtained by biopsy. Samples may contain peptides or proteins from multiple cell lines or types. In other preferred embodiments, samples are obtained from bodily fluids, such as serum, urine, spinal fluid, or synovial fluid. Preparations from blood samples may also be employed, whether cells, e.g. erythrocytes, are first removed or not.

A sample, which may contain a great variety of different proteins, can be digested with a suitable proteolytic enzyme, e.g. trypsin or chemical cleavage reagent. Any suitable enzyme that yields a significantly digested proteinaceous preparation (i.e. mostly peptides as opposed to proteins) may be employed, for example endoproteinases Lys-C, Glu-C, Asp-N, chymotrypsin, and thermolysin. In a preferred embodiment, the enzyme is trypsin. If desired, digestion with two or more different proteolytic enzymes may be carried out to yield smaller peptides suitable for mass spectrometry analysis (e.g., peptides of about 30 amino acids in length or less, for current MS methods).

In certain preferred embodiments, the sample comprises a digested biological sample selected from the group consisting of a digested crude cell extract, a digested tissue sample, a digested serum sample, a digested blood sample, a digested urine sample, a digested synovial fluid sample, and a digested spinal fluid sample. The digested preparation may be obtained using at least one proteolytic enzyme, such as trypsin.

In an especially preferred embodiment, samples are digested with both a proteolytic enzyme and also with any suitable phosphatase, including alkaline phosphatase, to remove phosphoric groups from phosphorylated peptides in the preparation. This avoids possible contamination of isolated sialylated peptides with phospho-peptides. Preparations may optionally be digested with one more glycosidase enzyme before or after initial isolation of sialylated peptides.

Any suitable titanium dioxide or zirconium dioxide stationary phase material may be used with the methods of the present invention, including but not limited to titanium dioxide or zirconium dioxide particles used as free particles or used to form a surface coat on some other material. Titanium dioxide or zirconium dioxide stationary phase material may be packed in any suitable container known in the art or used in batch, or in flow lines. In one non-limiting example, titanium dioxide spheres may be packed into thin capillary columns, with an internal diameters of about 50 to 300 micrometers. Capillary columns of this type containing reversed-phase or ion exchange supports are widely used in the art. In another non-limiting example, titanium dioxide or zirconium dioxide can be used to coat microtitre plates formatted for processing of multiple samples.

It will be readily understood by those skilled in the art that the stationary phase may be coupled in line with one or mass spectrometers or other analytical devices.

Titanium dioxide or zirconium dioxide stationary phase material can be adapted to be used as (i.e. coupled to) part of an electrospray source on a mass spectrometer, so that peptides can be readily analyzed after isolation with minimal sample loss. In one non-limiting example, a capillary column itself is fitted directly to the mass spectrometer and acts as a fritless electrospray interface. For example, using standard low-volume HPLC fittings, the column is inserted into a plastic (PEEK) micro-tee fitting (shaped like the letter T). A capillary line from a solvent delivery system is attached to the opposite side of the micro-tee fitting, in line with the column, so different solvents can be delivered through the column to elute samples bound to the column. A gold rod is inserted into the third stem of the micro-tee, perpendicular to the solvent delivery lines and column, to supply the electrical connection from the mass spectrometer through a liquid-metal junction. All three devices are secured in the fitting with standard PEEK micro-fingertight fittings and tubing sleeves. The source normally used with the mass spectrometer is removed and replaced by a metal platform that holds this micro-tee assembly. The position of the capillary column tip can be precisely controlled by making adjustments with an XYZ micromanipulator on the platform, so the position of the spraying column tip relative to the mass spectrometer orifice is optimized for maximum ion current signal. In this way microcolumn chromatography and micro-electrospray ionization may be combined into one device.

Alternatively, titanium dioxide or zirconium dioxide stationary phase material can be used off-line, for example, in a micropipette tip. These devices are well known in the art, and may be attached to standard laboratory pipetting devices and are used in the same manner as pipette tips: as the sample is aspirated into the tip, it becomes bound to the chromatography support, which is then washed before eluting the sample in a small volume for analysis. The tip, for example, may be fabricated by embedding titanium dioxide or zirconium dioxide stationary phase material in a gel matrix in the dispensing end of a standard micropipette tip or by packing the material into a constricted tip or a tip that is closed with a plug or into any tip in a manner that permits loading and elution of samples.

Preparations containing one or more sialylated proteins are loaded onto titanium dioxide or zirconium dioxide stationary phase in a loading buffer comprising at least about 20% of an organic phase, preferably acetonitrile. It is important that sufficient organic phase be present to suppress adsorption of non-sialylated proteins to titanium dioxide or zirconium dioxide stationary phase. Any suitable organic phase solvent known in the art may be used, preferably acetonitrile. The amount of organic phase, preferably acetonitrile, may be at least about 30%, at least about 40%, at least about 50%, at least about 60%, at least about 70%, most preferably, at least about 80%, at least about 90% or 100%.

It is important that the loading buffer be acidic. As used herein, the term "acidic" means, at most pH 3.0, most preferably 2.0 or below.

It is important that the loading buffer comprise substituted aromatic carboxylic acid, most preferably dihydroxy benzoate or phthalic acid. Other substituted aromatic carboxylic acids may also be used, including but not limited to salicylic acid. The loading buffer should comprise at least about 6.5 mM of substituted aromatic carboxylic acid, preferably 2.2 M. The amount of substituted aromatic carboxylic acid can be at least about 64.9 mM, at least about 129.6 mM, at least about 324.5 mM, at least about 649.0 mM, at least about 1.3 M or at least about 2.2 M. Alternatively, the loading buffer can comprise at least about 11 mM of short chain, non-aromatic, hydroxylated carboxylic acid, preferably 1 M. The amount of substituted aromatic carboxylic acid can be at least about 110 mM, at least about 220 mM, at least about 330 mM, at least about 600 mM, at least about 1 M or at least about 2.2 M.

The loaded stationary phase can, optionally, be washed with any suitable buffer with pH below 7.0. In one non-limiting example, loaded stationary phase can be washed with loading buffer.

A preparation enriched in sialylated proteins can then be eluted from loaded stationary phase with an elution solution, having pH at least 9.0, preferably 10.5. Any suitable buffer may be used as an elution buffer. In one non-limiting example, proteins are eluted in a small volume by directly applying 3 ul of NH4OH solution.

In one embodiment, the present invention provides a method for isolation of sialylated peptides comprising the steps of
  loading a solution containing one or more sialylated peptides onto titanium dioxide or zirconium dioxide stationary phase material wherein said solution is acidic and comprises at least 20% organic phase and at least about 6.5 mM of substituted aromatic carboxylic acid
  eluting proteins from said stationary phase material with an alkaline solution having pH of at least 9.0

In another embodiment, the present invention provides a method for isolation of sialylated peptides comprising the steps of
  loading a solution containing one or more sialylated peptides onto titanium dioxide or zirconium dioxide stationary phase material wherein said solution is acidic and comprises at least 20% organic phase and at least about 6.5 mM of short chain, non-aromatic, hydroxylated carboxylic acid
  eluting proteins from said stationary phase material with an alkaline solution having pH of at least 9.0

Method for Analysing Sialylated Proteins by Combining Isolation of Sialylated Peptides with Mass Spectroscopy.

Isolated sialylated peptides may be analyzed by standard methods to determine peptide sequence, sialylation status, and mass of glycosylated peptide and/or de-glycosylated peptide. In certain preferred embodiments, modified peptides isolated according to the method of the invention are analyzed by mass spectrometry (MS) methods, since MS is presently the most sensitive method for analyzing peptides. MS requires less analyte material to provide high-quality information about peptides than other current methods. It will be recognized by one skilled in the art that equivalent or subsequently improved methods of analyzing modified peptides are within the scope of the invention. For example, at present, peptides of about 30 amino acids in length or less are most suitable for MS analysis, but future improvements in methods may allow the analysis of longer peptides.

Accordingly, in a preferred embodiment, the general method of the invention further encompasses characterization of sialylated proteins isolated according to methods of the present invention. Characterization can be by mass spectrometry (MS), tandem mass spectrometry (MS-MS), and/or $MS^3$ analysis. In one preferred embodiment, matrix-assisted laser desorption/ionization time-of-flight (MALDI-TOF) mass spectrometry is utilized to measure the masses of purified peptides. MALDI-TOF mass spectrometry is useful for rapidly screening samples before analyzing them by other, more complex methods such as tandem mass spectrometry (MS/MS) (see below), and is both sensitive and simple. For proof-of-principle experiments or diagnostic assays, where the objective of the isolation is to determine if an expected peptide is present among the purified sialylated peptides, the mass of the purified peptide(s) is calculated from the peptide's known sequence and searched for in the mass spectrum.

It will be readily understood by one skilled in the art that the present invention further provides a method of diagnosis, prognosis or monitoring a condition associated with a change of sialylation status. Sialylation status of sialylated peptides isolated from a patient sample can be compared with sialylation status of corresponding peptides in a healthy control sample to identify any changes in sialylation status of isolated sialylated peptides.

MALDI-TOF mass analysis of peptides is a rapidly evolving field, and the preferred methods for preparing isolated modified peptides for analysis and carrying out such analysis is likely to change over time. Nonetheless, MALDI-TOF analysis is carried out according to standard methods, and improvements in these methods are within the scope of the present invention.

To identify sialylation sites, all or some portion of the sample is preferably analyzed before and after treatment with one or more enzymes that remove glycosyl groups from the peptide. For example, terminal sialic acids can generally be removed by treatment with neuramidase. This is a simple and reliable assay to confirm that peptides are sialylated, and to count the number of terminal sialylic groups present in each peptide. The mass of a peptide that is not sialylated will not change as a result of neuramidase treatment.

In some applications, it may not be possible to identify the sialylated peptides isolated from the complex mixture present in preparation simply by measuring peptide masses because many different peptide sequences could produce each mass observed. Accordingly, in another preferred embodiment, modified peptides isolated from complex mixtures are analyzed by tandem mass spectrometry (MS/MS or MS$^3$), where peptide ions isolated in one stage of mass spectrometry are deliberately fragmented by collisions in the mass spectrometer, and then the fragment masses are measured. The fragment masses observed for each peptide are a property of that peptide's sequence and are a more specific indicator of the parent protein than the peptide's mass, i.e. the fragment masses are related to the peptide's sequence and can be used to identify the protein from which the peptide originated. If the sequence of the peptide's parent protein is known, then the peptide can be unambiguously matched to its parent protein without directly interpreting a sequence from the fragment mass spectrum.

A particular peptide's measured mass and partial sequence is sufficient to unambiguously match it to its parent protein. Parent protein sequences are increasingly becoming available as the genomes of common biological model organisms become known. MS/MS spectra can be collected rapidly (<400 msec per peptide) and in a data-dependent manner through instrument-control software, so very complex samples are amenable to analysis. With nanospray infusion methods, sample volumes of 2 microliters can be analyzed for an hour or longer. Accordingly, in a preferred embodiment of the disclosed method, isolated sialylated peptides can be characterized by tandem MS, for example liquid chromatography (LC)-MS/MS.

Following MS/MS characterization, sialylated peptides may be unambiguously identified by analyzing the product ion spectra with a search program in an attempt to match the spectra obtained for the modified peptide with the spectra for a known peptide sequence, thereby identifying the parent protein(s) of the sialylated peptide. For example, Sequest, a program that correlates an experimental spectrum to a library of theoretical spectra derived from protein sequence databases to find a best-fit match, may advantageously be used for such a search. It will be recognized that equivalent search programs may be employed in the practice of disclosed method. Accordingly, in a preferred embodiment, the method of the invention further comprises the step of utilizing a search program to substantially match the spectra obtained for the modified peptide with the spectra for a known peptide sequence, thereby identifying the parent protein(s) of the sialylated peptide.

As discussed above, in practising the isolation methods of the invention, a device for isolating sialylated peptides may be coupled directly to a mass spectrometer so that peptides are analyzed as they elute from the titanium dioxide or zirconium dioxide stationary phase. In this manner, the method of the invention may be readily automated, so as to allow the efficient, high-throughput isolation and characterization of sialylated peptides from complex mixtures.

The chromatography system may also be multi-modal, i.e. it can operate in two or more separation modes sequentially. In one non-limiting example, one dimension of multi-modal liquid chromatography could be immunoaffinity depletion of plasma samples, using antibodies specific for high abundance plasma proteins, such as albumin, IgG, IgA, haptoglobin, transferring and antitrypsin. One skilled in the art will readily envision other treatments, such as a column of immobilized protein used upstream of a mass spectrometer to catalyze a reaction on the sample to be analyzed.

In some cases it is useful to mass-modify isolated sialylated peptides with isotopic labels. Isotopic modification may, optionally, be done before, after or during enzymatic hydrolysis. For example, to facilitate comparisons of changes in sialylation state between two different samples, trypsin digestion can be undertaken in buffers containing either ordinary water, as control, or O$^{18}$-labelled water, for comparison. This produces mass-modified peptides in a comparison sample that can be conveniently and easily compared in a single mass spectroscopy experiment with corresponding peptides in control samples.

Method for Identifying Biomarkers of Conditions Associated with Chance of Sialylation Status.

Sialylated proteins are isolated by the method of the present invention from samples taken from ordinary healthy persons, as controls, and from patients suffering from a condition associated with change of sialylation status, for comparison. Any suitable sample may be used for comparison. The control and patient samples are then compared using mass spectroscopy to identify specific proteins that exhibit a change of sialylation status.

In a preferred embodiment, sialylated proteins from control or patient samples are mass-modified with isotopic labels to permit convenient comparison in a single mass spectroscopy experiment. Alternatively, control and patient samples may be compared by LC-retention time and accurate mass measurement or the samples can be labelled by using the iTRAQ technology well known in the art.

In one embodiment, the invention provides a method of identifying biomarkers of a condition associated with change in sialylation status comprising the steps of
  obtaining samples from ordinary healthy controls and from patients suffering from a condition associated with change of sialylation status
  loading said samples in an acidic solution comprising at least 20% organic phase and at least about 6.5 mM of substituted aromatic carboxylic acid onto titanium dioxide or zirconium dioxide stationary phase material
  eluting peptides from said stationary phase material with an alkaline solution having pH of at least 9.0
  analyzing eluted peptides by mass spectroscopy
  comparing sialylation status of control and patient samples to identify proteins in which levels of sialylation and/or glycan heterogeneity are altered in patient samples.

In another embodiment, the invention provides a method of identifying biomarkers of a condition associated with change in sialylation status comprising the steps of
  obtaining samples from ordinary healthy controls and from patients suffering from a condition associated with change of sialylation status
  loading said samples in an acidic solution comprising at least 20% organic phase and at least about 11 mM short chain, non-aromatic, hydroxylated carboxylic acid onto titanium dioxide or zirconium dioxide stationary phase material
  eluting peptides from said stationary phase material with an alkaline solution having pH of at least 9.0
  analyzing eluted peptides by mass spectroscopy
  comparing sialylation status of control and patient samples to identify proteins in which levels of sialylation and/or glycan heterogeneity are altered in patient samples.

It will be readily understood that eluates can optionally be derivatized or otherwise treated prior to analysis by mass spectrometry.

Purification of Phosphorylated Peptides Using Titanium Dioxide or Zirconium Dioxide Stationary Phase Material and a Buffer Comprising a Substituted Aromatic Carboxylic Acid.

The methods of the present invention may be used as described for sialylated peptides to isolate phosphorylated peptides.

In one embodiment, the present invention provides a method for isolation of phosphorylated peptides comprising the steps of
- loading a solution containing one or more phosphorylated peptides onto titanium dioxide or zirconium dioxide stationary phase material wherein said solution is acidic and comprises at least 20% organic phase and at least about 6.5 mM of substituted aromatic carboxylic acid
- eluting proteins from said stationary phase material with an alkaline solution having pH of at least 9.0

The phosphate group is believed to have an effect on the ionization of phosphorylated peptides in MS, resulting in decreased signal intensity for phosphorylated peptides in the presence of non-phosphorylated peptides (i.e., an ion suppression phenomenon). Matrix additives like ammonium citrate or phosphoric acid have been shown to enhance the relative abundance of phosphorylated peptides in the presence of non-phosphorylated peptides in MALDI MS.

To reduce the suppression of phosphorylated peptides, caused by the presence of non-phosphorylated peptides, it is advantageous to pre-purify the phosphorylated peptides, especially from complex peptide mixtures. Enrichment of phosphorylated peptides from peptide mixtures using immobilized metal affinity chromatography (IMAC) is widely used (28-34). With this approach the negatively charged phosphorylated peptides are purified by their affinity to metal ions like $Fe^{3+}$ or $Ga^{3+}$. However, frequently non-phosphorylated peptides, including those containing multiple acidic residues, are also enriched by this method (35). Blocking the acidic residues by O-methylesterification has been shown to enhance the specificity of the phospho-peptide binding (35). Nonetheless, in our experience the yield of this derivatization is below 100%, which compromises the sensitivity of this procedure and increase the complexity of the sample. In addition, O-methylesterification often causes a partially deamidation and subsequent methylation of Asn and Gln residues, and these byproducts complicate the MS analysis and data interpretation further (36). Furthermore, this method requires evaporation of the aqueous solvent from the peptide sample prior to the addition of the esterification reagent and this step is know to cause adsorptive losses, resulting in decreased sensitivity (37-38).

Chemical modification by β-elimination and concurrent Michael addition has also been widely used for affinity purification and quantitation of phosphorylated peptides (e.g., (39)). However, this strategy is suffering from several shortcomings including lack of reproducibility, sensitivity and introduction of unwanted side reactions (40).

Pinkse et al. (41) introduced a strategy whereby titanium dioxide ($TiO_2$) was used as an alternative to IMAC for the selective enrichment of phosphorylated peptides prior to ESI liquid chromatography tandem MS. They used an on-line $TiO_2$ pre-column coupled directly to a reversed-phase capillary column and with this setup successful analysis of various phosphorylated peptides was achieved. However, the selectivity of this method was somewhat compromised by the detection of several acidic non-phosphorylated peptides which were also retained by their $TiO_2$ column.

Embodiments of the present invention provide a new and improved procedure for using titanium dioxide or zirconium dioxide stationary phase which significantly enhances binding selectivity for phosphorylated peptides, thereby enabling phosphorylated peptide characterization from low femtomole level phosphorylated proteins.

Method for Quantifying Phosphorylated Peptides Involving Derivatisation of Peptides while Immobilised on Stationary Phase.

The purification methods of the present invention can be used in improved methods for identification and quantification of phosphorylated peptides. Known methods for derivatization of peptides to facilitate mass spectrometric analysis can be undertaken using peptides loaded onto a stationary phase. In particular, the methods of derivitization which can be undertaken using peptides loaded onto a stationary phase, as described herein, include methods disclosed by Haystead et. al. in "Method for determination of the amount of either phosphotyrosine or phosphoserine in a protein," U.S. Pat. No. 5,686,310, which US patent is hereby incorporated by reference in entirety into this specification. Other examples of methods of derivitization which can be undertaken using peptides loaded onto a stationary phase, as described herein, include methods disclosed by Lee et. al. in "Isotope-coded N-terminal sulfonation of peptides allows quantitative proteomic analysis with increased de novo peptide sequencing capability," Rapid Communications in Mass Spectrometry, 18:3019 (2004) (42), which is hereby incorporated by reference in entirety into this specification.

In one embodiment, the present invention provides a method for quantifying phosphorylated peptides, which method comprises:
- loading a solution comprising a mixture of peptides onto stationary phase material comprising TiO2 wherein said solution is acidic and comprises at least 20% acetonitrile and at least about 6.5 mM of substituted aromatic carboxylic acid
- derivatising said peptides while immobilized on said stationary phase at a pH below 9.5;
- eluting derivatized phosphorylated peptides from said stationary phase by increasing the pH to above 9.5 or by contacting the support with a phosphoric compound or by irradiating the support
- quantifying the derivatized biomolecules by an analytical instrument.

Method for Analysing Phosphorylated Peptides by Combining Isolation of Phosphorylated Peptides with Mass Spectrometry The methods of the present invention may be used as described for sialylated peptides to analyse phosphorylated peptides.

Dynamic post-translational modification of proteins is important for maintaining and regulating protein structure and function. Among the several hundred different types of post-translational modifications characterized to date, protein phosphorylation plays a prominent role. Enzyme-catalyzed phosphorylation and de-phosphorylation of proteins is a key regulatory event in the living cell. Complex biological processes such as cell cycle, cell growth, cell differentiation and cell metabolism are orchestrated and tightly controlled by reversible phosphorylation events which modulate protein activity, stability, interaction and localization. Perturbations in phosphorylation states of proteins, e.g. by mutations which generate constitutively active or inactive protein kinases and phosphatases, play a prominent role in oncogenesis. Comprehensive analysis and identification of phosphoproteins, combined with exact localization of phosphorylation sites in those proteins ('phosphoproteomics') is a prerequisite for understanding complex biological systems and the molecular features leading to disease.

It is estimated that ⅓ of all proteins present in a mammalian cell are phosphorylated and that kinases, enzymes responsible for that phosphorylation, constitute about 13% of the expressed genome. Organisms use reversible phosphorylation of proteins to control many cellular processes including signal transduction, gene expression, the cell cycle, cytoskeletal regulation and apoptosis. A phosphate group can modify serine, threonine, tyrosine, histidine, arginine, lysine, cysteine, glutamic acid and aspartic acid residues. However, the phosphorylation of hydroxyl groups at serine (90%), threonine (10%), or tyrosine (0.05%) residues are the most prevalent, and are involved, along with other processes, in metabolism, cell division, cell growth, and cell differentiation. Because of the central role of phosphorylation in the regulation of life, much effort has been focused on the development of methods for characterizing protein phosphorylation.

The identification of phosphorylation sites on a protein is complicated by the facts that proteins are often only partially phosphorylated and that they are often present only at very low levels. Therefore techniques for identifying phosphorylation sites should preferably work in the low picomole to sub-picomole range.

Recently, a number of mass spectrometric (MS) based strategies have been developed which are relative sensitive and in many cases easier to perform than Edman degradation with respect to handling complex mixtures. The increased sensitivity is especially needed for low stoichiometric phosphorylation. However, presently none of these MS based methods can individually provide a complete characterization of a phosphorylated protein. Common for the MS based strategies is that the phosphorylated protein is enzymatically degraded to peptides, which are subsequently analyzed by MS to detect a mass increment of 80 Da per phosphate group. Since sulfonation gives the same mass shift, this strategy is often combined with phosphatase treatment to specifically cleave off the phosphate group from the peptide. This mass shift can be monitored by MS as a loss of 80 Da. This differential peptide mass mapping can be combined with purification of peptides using microcolumns packed with material of increasing hydrophobicity. In MALDI TOF MS operating in reflector ion mode, the loss of phosphoric acid in the gas phase is often detected from phosphorylated peptides as a poorly resolved peak, originating from metastable fragmentation. The exact site of phosphorylation can often be localized using tandem MS, however, the loss of phosphoric acid upon collision induced dissociation (CID) is frequently observed as the major fragmentation pathway and this may interfere with the interpretation, due to inadequate fragmentation of the peptide backbone.

Metastable decomposition may result in the presence of additional peaks in the mass spectrum. Metastable decomposition of phosphopeptides has been noted by others and can be used to recognize and assign phosphopeptides in a MALDI-TOF mass spectrum (Annan and Carr, Anal. Chem. 68: 3413-21 (1996)(43)). The peaks for decomposition products are broader than the peaks for phosphopeptides because the decomposition products form after ionization and the instrument is configured to focus ions that are stable during analysis. For similar reasons, the expected mass shift for loss of phosphate is −98, but −84 mass shifts are observed because, unlike a stable ion, the mass of a decomposition product changes during analysis. Analysis of a large number of synthetic phosphopeptides by MALDI-TOF mass spectrometry has indicated that some peptides containing phosphoserine or phosphothreonine—but not phosphotyrosine—residues undergo metastable decomposition. Accordingly, metastable decomposition is a reliable indicator of peptides that contain phosphoserine or phosphothreonine. Metastable decomposition may be observed in the MALDI-TOF spectra of some peptides that contain phosphoserine or phosphothreonine, without additional sample treatment steps and without consuming more sample.

If phosphopeptides are being isolated, it may be observed that during the fragmentation process of MS/MS, peptides containing phosphoserine or phosphothreonine often form an ion by simple loss of phosphate to produce a neutral-loss ion that has a mass 98 lower than the unfragmented parent ion. If the parent ion has a charge of +1, the neutral-loss ion has a mass-to-charge value (m/z) of 98/1 or 98 lower than the parent ion mass-to charge value. Likewise, phosphopeptide parent ions with charges of +2, +3, or +4 will give neutral-loss ions with m/z values that are 49, 32.7, and 24.5 lower than the parent ion.

Neutral loss during MS/MS is the same process as metastable decomposition during MALDI-TOF mass spectrometry. Therefore many of the phosphopeptides showing neutral loss during LC-MS/MS are expected to be the same phosphopeptides that give metastable decomposition during MALDI-TOF mass spectrometry. For each neutral-loss MS/MS spectrum, the parent ion mass (m) can be calculated from the parent ion mass-to-charge value (m/z) and the charge (z) inferred from the neutral loss value (+2 for neutral loss of 49, +3 for 32.7, and +4 for 24.5). Some individual peptides may be observed to undergo neutral loss as +2, +3, and +4 ions. A comparison of datasets can confirm that the same peptides are detected by both mass analysis methods.

EXAMPLES

1. Isolation of Sialylated Tryptic Fragments of Fetuin with Titanium Dioxide Stationary Phase Material Modified trypsin was from Promega (Madison, Wis., USA). Fetuin was from Sigma. Poros R2 and Poros Oligo R3 reversed phase material were from PerSeptive Biosystems (Framingham, Mass.). GELoader tips were from Eppendorff (Eppendorf, Hamburg, Germany). 2,5-Dihydroxybenzoic acid (DHB) was from Fluka (St. Louis, Mo.). 3M Empore C8 disk was from 3M Bioanalytical Technologies (St. Paul, Minn., USA). Syringe for HPLC loading were from SGE (Victoria, Australia). The water was from a Milli-Q system (Millipore, Bedford, Mass.). Titanium dioxide beads were obtained from a disassembled $TiO_2$ column (1350L250WO46 Titansphere, 5 micron, 250×4.6 mm) purchased from GL sciences Inc, Japan.

Fetuin

Bovine fetuin was dissolved in 50 mM $NH_4HCO_3$, pH 8, 10 mM DTT and incubated at 56° C. for 30 min. Iodoacetamide was added to the solution (final concentration 20 mM) and it was incubated at room temperature for 1 h in the dark. Adding more DTT quenched the reaction. The alkylated protein was diluted to 20 pmol/μL and subsequently digested over night at 37° C. by trypsin (substrate/enzyme ratio of 100/2). The resulting peptides were further treated with alkaline phosphatase in order to avoid co-purification of phosphorylated peptides from Fetuin.

Alkaline Phosphatase Treatment

The tryptic peptides originating from Fetuin were treated with 0.1-0.5 U alkaline phosphatase in 50 mM $NH_4HCO_3$, pH 7.8 at 37° C. for 1 hour.

Glycosidase Treatment

N-Glycosidase F: Glycosylated peptides purified by $TiO_2$ were lyophilized and redissolved in 50 mM $NH_4HCO_3$, pH 7.8 containing 0.2 U N-glycosidase F. The deglycosylation was performed from 2-12 h at 37° C.

Purification of Sialic Acid Containing Glycopeptides Using TiO$_2$ Microcolumns

TiO$_2$ microcolumns were packed in GELoader tips essentially as described in (26) or in p10 micropipette tips (depending on the amount of material to be purified). Briefly, a small plug of C8 material was stamped out of a 3M Empore™ C8 extraction disk (e.g., using a HPLC syringe needle) and placed at the end of the tip. TiO2 beads were dissolved in acetonitrile and packed on top of the C8 disk using a 1 mL disposable syringe. Peptides originating from proteolytic digestion of fetuin or human plasma proteins were diluted 1:5 in loading buffer (2,5-Dihydroxybenzoic acid (DHB) (350 mg/mL) in 80% acetonitrile/3-5% TFA) and loaded onto the TiO$_2$ microcolumn. The column was washed with 10 µL loading buffer followed by 20-40 µL washing buffer (80% acetonitrile/1% TFA). The glycopeptides were eluted using 20-60 µL NH$_4$OH, pH 10.5. An aliquot of the eluate was acidified, purified using Poros R3 reversed phase microcolumns and analyzed by MALDI MS. The remaining eluate was lyophilized for N-glycosidase F digestion.

Matrix-Assisted Laser Desorption/Ionization Time-of-Flight Mass Spectrometry (MALDI-TOF MS)

MALDI-MS was performed using a Voyager STR (PerSeptive Biosystems, Framingham, Mass.). All spectra were obtained in positive reflector or linear mode. Mass spectrometric data analysis was performed using either the MoverZ software (www.proteometrics.com) or the software MassLynx 3.5.

FIG. 1 (A) shows the MALDI mass spectrum of fetuin tryptic fragments, treated with alkaline phosphatase to remove phosphoryl groups that might otherwise contaminate isolation of sialylated fragments. FIG. 1 (B) shows the MALDI mass spectrum of fetuin tryptic fragments, without alkaline phosphatase treatment after purification using titanium dioxide stationary phase. As shown, in the absence of alkaline phoshatase treatment, considerable contamination is observed of the three sialylated tryptic fragments of fetuin by phosphorylated, non-sialylated fragments. FIG. 1(C) shows the MALDI mass spectrum of fetuin tryptic fragments treated with alkaline phosphatase after purification with titanium dioxide stationary phase. FIG. 1 (D) shows the MALDI mass spectrum of fetuin tryptic fragments treated with alkaline phosphatase and PNGaseF to remove glycosyl moieties, after purification with titanium dioxide comprising stationary phase.

2. Specificity of Isolation Using Titanium Dioxide Stationary Phase for Sialylated Compared with Non-Sialylated Fragments O$^{18}$-labelling of tryptic fragment.

Fetuin tryptic peptides were lyophilized and redissolved in O$^{18}$ buffer containing 1 µg trypsin and 20% methanol and incubated over night in 37° C. (27).

Glycosidase Treatment

Neuramidase: Dephosphorylated tryptic peptides originating from Fetuin or plasma proteins were lyophilized and redissolved in NH$_4$Acn, pH 6. Neuramidase was added to the peptide mixtures and the sample was incubated over N-Glycosidase F as described for example 1.

To measure the specificity of the titanium dioxide procedure towards sialic acid containing glycopeptides compared to non-sialic acid containing glycopeptides, tryptic peptide from fetuin with O$^{16}$ and without O$^{18}$ neuramidase treatment were mixed 1:1 and separated by titanium dioxide stationary phase. The eluate was treated with PNGaseF and analysed by MALDI MS, as described in example 1.

Figure 2:
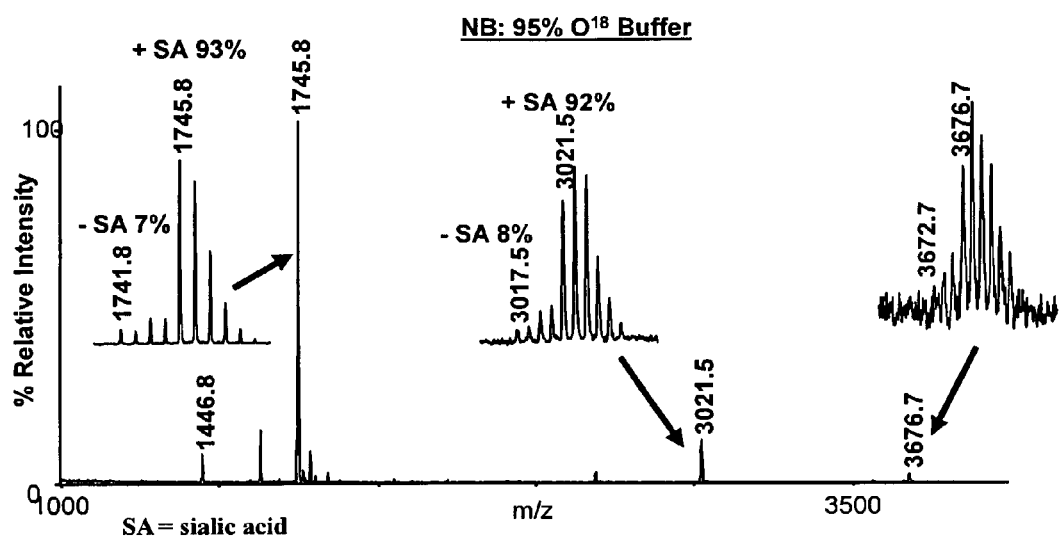
FIG. 2 shows MALDI mass spectra of $O^{16}$-and $O^{18}$-labelled sialylated and de-sialylated tryptic fragments of feutin, which were subject to purification with titanium dioxide stationary phase and a loading buffer comprising a substituted aromatic carboxylic acid. Specificity of the purification for sialylated fragments is illustrated.

FIG. 2 shows the MALDI mass spectrum of O$^{16}$- and O$^{18}$-labelled tryptic fragments of sialylated and de-sialylated fetuin. As shown, the titanium dioxide procedure enriches sialylated fragments at least 13-fold over non-sialylated fragments.

3. Specificity of Isolation Using Titanium Dioxide Stationary Phase for Sialylated Compared with Non-Sialylated, Fragments—Importance of a Substituted Aromatic Carboxylic Acid or a Non-Aromatic Short Chain, Hydroxylated Carboxylic Acid in the Loading Buffer Titanium dioxide has been used as material for normal phase separation of glycopeptides using hydrophilic interaction chromatography (HILIC). The glycopeptides from RNAse B (high mannose structures) were subject to purification using titanium dioxide stationary phase in an HILIC loading buffer and compared with purification using a loading buffer that included Dihydroxybenzoic acid (DHB) (350 mg/mL or 2.27 M) in 80% acetonitrile/3-5% TFA. (Concentrations of DHB of 1 mg/ml constitute solutions of about 6.5 mM). Eluates were analysed by MALDI MS as described for example 1.

Figure 3:
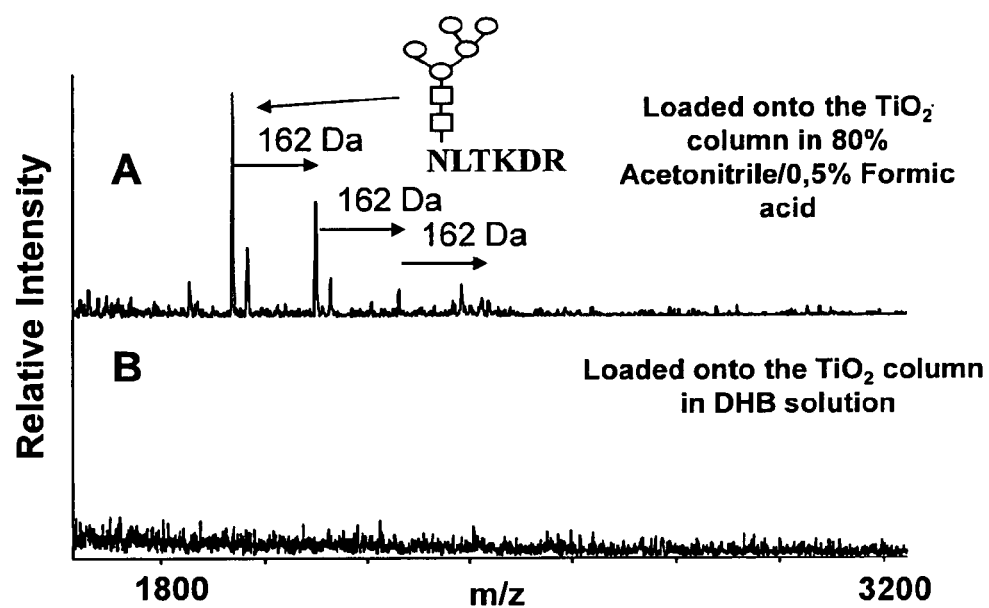
FIG. 3A shows MALDI mass spectra of tryptic fragments of a non-sialylated glycoprotein isolated with HILIC buffers.
FIG. 3B shows MALDI mass spectra of tryptic fragments of a non-sialylated glycoprotein isolated with DHB buffer.

FIG. 3 (A) shows the MALDI mass spectrum of mannose rich, non-sialylated RNAse B peptides loaded on titanium dioxide stationary phase in 80% acetonitrile with 0.5% formic acid. FIG. 3(B) shows the MALDI mass spectrum of RNAse B peptides loaded on titanium dioxide stationary phase in 80% acetonitrile with 3-5% TFA and 350 mg/ml of dihdroxybenzoic acid (DHB). As shown, the use of DHB in the loading buffer greatly enhances specificity of titanium dioxide stationary phase for sialic acid containing fragments.

Figure 4:
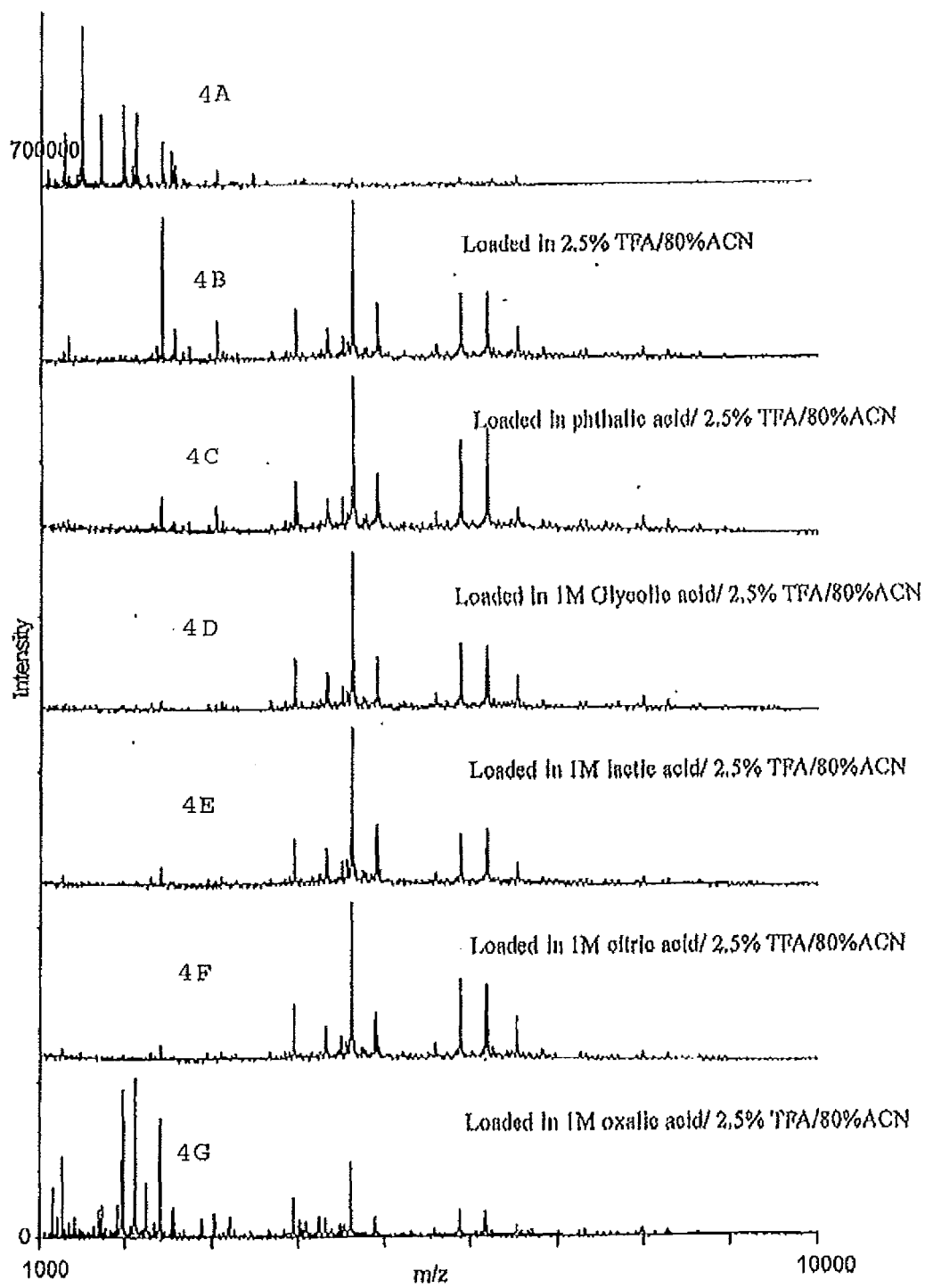
FIG. 4A shows MALDI mass spectra of sialylated tryptic fragments of feutin treated with alkaline phosphatase and loaded on $TiO_2$ in acidic loading buffer alone.
FIG. 4B shows MALDI mass spectra of sialylated tryptic fragments of feutin treated with alkaline phosphatase and loaded on $TiO_2$ in acidic loading buffer comprising 2.5% TFA and 80% acetonitrile.
FIG. 4C shows MALDI mass spectra of sialylated tryptic fragments of feutin treated with alkaline phosphatase and loaded on $TiO_2$ in acidic loading buffer comprising 2.5% TFA and 80% acetonitrile and saturated phthalic acid.
FIG. 4D shows MALDI mass spectra of sialylated tryptic fragments of feutin treated with alkaline phosphatase and loaded on in acidic loading buffer comprising 2.5% TFA and 80% acetonitrile and 1 M glycolic acid.
FIG. 4E shows MALDI mass spectra of sialylated tryptic fragments of feutin treated with alkaline phosphatase and loaded on $TiO_2$ in acidic loading buffer comprising 2.5% TFA and 80% acetonitrile and 1 M lactic acid.
FIG. 4F shows MALDI mass spectra of sialylated tryptic fragments of feutin treated with alkaline phosphatase and loaded on $TiO_2$ in acidic loading buffer comprising 2.5% TFA and 80% acetonitrile and 1 M citric acid.
FIG. 4G shows MALDI mass spectra of sialylated tryptic fragments of feutin treated with alkaline phosphatase and loaded on $TiO_2$ in acidic loading buffer comprising 2.5% TFA and 80% acetonitrile and 1 M oxalic acid.

FIG. 4 shows the MALDI mass spectrum of fetuin tryptic peptides loaded onto titanium dioxide stationary phase in 80% acetonitrile with 2.5% TFA and 1 M glycolic, lactic, citric or oxalic acid. As shown, except for 2 carbon oxalic acid, non-aromatic, short chain, hydroxylated carboxylic acids in the loading buffer also greatly enhance specificity of titanium dioxide stationary phase for sialic acid containing fragments.

4. Isolation of Sialylated Peptides from Human Plasma

Plasma

Human plasma (60 ul) was depleted for the six highest abundant proteins: albumin, IgG, IgA, haptoglobin, transferrin, and antitrypsin using affinity-purified antibodies (Agilent). The plasma proteins were reduced and alkylated as described for Fetuin in example 1 and digested over night with trypsin.

Prior to purification of sialylated-glycopeptides with TiO$_2$ plasma samples were treated with alkaline phosphatase as described for example 1. Sialylated peptides were isolated as described for example 1. Eluates were analysed by MALDI MS as described for example 1. Isolated sialylated peptides were treated with PNGas F as described for example 1 to remove glycosyl moieties. PNGase F treated sialylated peptides were further analysed by MALDI MS.

FIG. 5(A) shows gel electrophoresis of plasma protein samples before and after removal of high abundance proteins and before and after purification using titanium dioxide stationary phase and a loading buffer comprising dihydroxy benzoate. As shown, sialylated low abundance plasma proteins are substantially enriched by the purification method. FIG. 5(B) shows MALDI mass spectra of tryptic fragments of low abundance plasma proteins. FIG. 5(C) shows MALDI mass spectra of isolated sialylated fragments. The inset shows MALDI mass spectra an aliquot of the sialylated peptides after treatment with PNGase F.

5. Identification of Sialylation Sites in Human Plasma Proteins

LC-MSMS

Purified SA-glycopeptides and deglycosylated peptides were analyzed using a QTOF Ultima mass spectrometer (Waters/Micromass UK Ltd., Manchester, UK) utilizing automated data-dependent acquisitionor on a LTQ-FT (Hybrid-2D-Linear Quadrupole Ion Trap—Fourier Transform Ion Cyclotron Resonance (FTICR) Mass Spectrometer, (Thermo Electron, Germany). A nanoflow HPLC system (Ultimate, Switchos2, Famos, LC Packings, Amsterdam, The Netherlands) was used for chromatographic separation of the peptide mixture prior to MS detection on the Ultima QTOF system whereas an Agilent 1100 nanoflow LC system was used for peptide separation prior to detection on the LTQ-FT instrument. The peptides were concentrated and desalted on a precolumn (75 µm inner diameter, 360 µm outer diameter, ReproSil-Pur C18 AQ 3 µm (Dr. Maisch, Germany)) and eluted at 200 nl/min by an increasing concentration of acetonitrile (2%/min gradient) onto an analytical column (50 µm inner diameter, 360 µm outer diameter, ReproSil-Pur C18 AQ 3 µm).

The PNGaseF treated sialic acid containing glycopeptides of example 4 were analysed by LC-MSMS. A total of 195 glycosylation sites were identified in 101 proteins. Examples of some specific sialylation sites are shown in FIG. 6.

Figure 6:
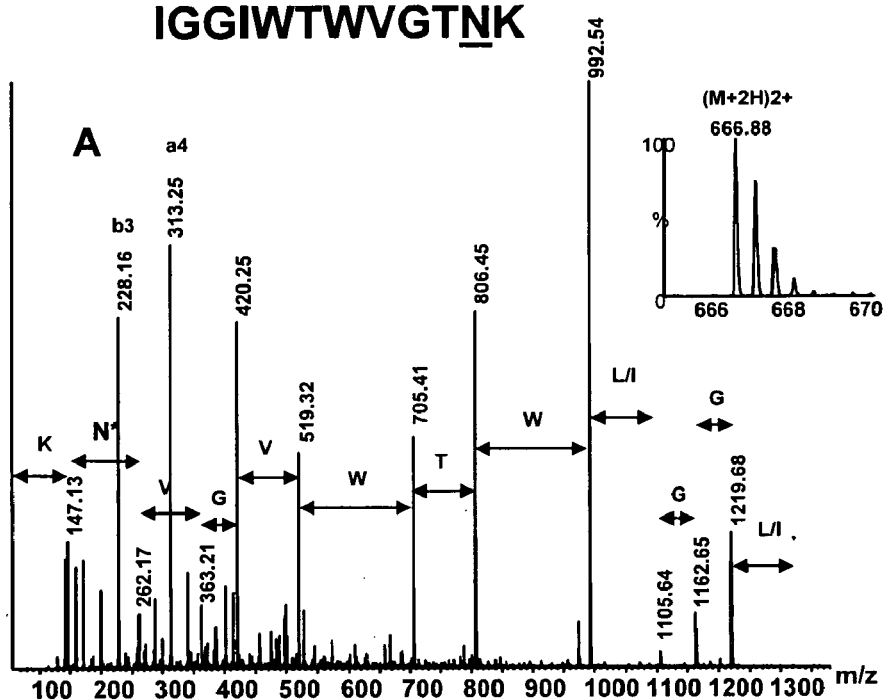
FIG. 6A shows LC-MSMS spectra of sialylated tryptic L-selectin fragments isolated from human plasma samples.
FIG. 6B shows LC-MSMS spectra of sialylated tryptic multimerin-1 fragments isolated from human plasma samples.
Figure 6:
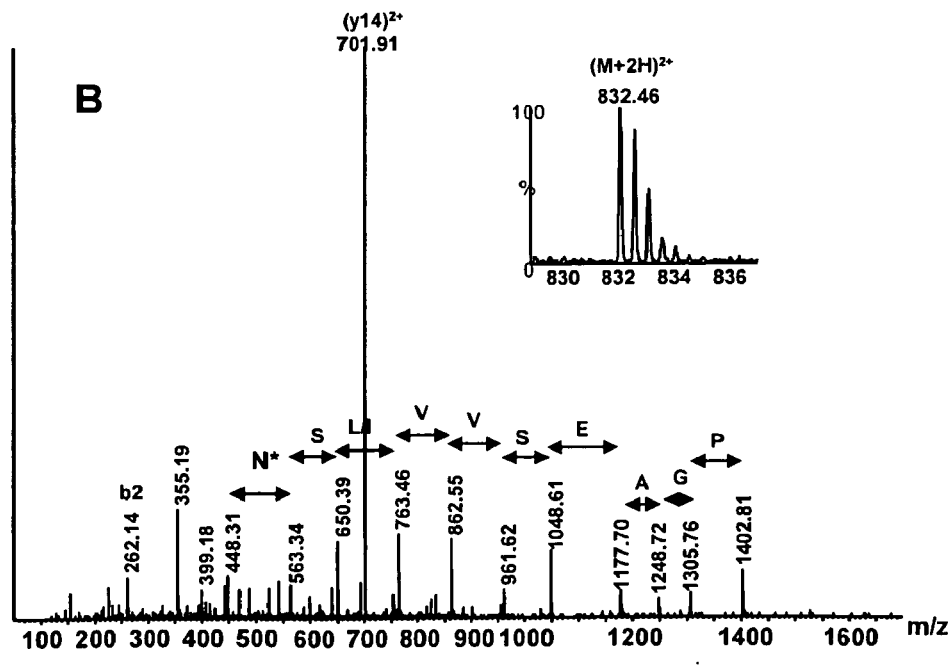

FIG. 6 shows LC-MSMS spectra of sialylated fragments isolated from human plasma samples. The samples are identified as a sialylated fragment of L-selectin FIG. 6 (A) and a sialylated fragment of Multimerin-1 FIG. 6 (B). As shown, specific sialylation sites can be readily identified by the methods of the present invention.

6. Identification of Biomarkers of Bladder Cancer

Plasma

Plasma from control and bladder cancer patient were depleted for the six highest abundant proteins: albumin, IgG, IgA, haptoglobin, transferrin, and antitrypsin using affinity-purified antibodies (Agilent). The plasma proteins were reduced and alkylated as described for Fetuin in example 1 and digested over night with trypsin. Prior to purification of SA-glycopeptides with $TiO_2$ the samples were treated with alkaline phosphatase.

Figure 7:
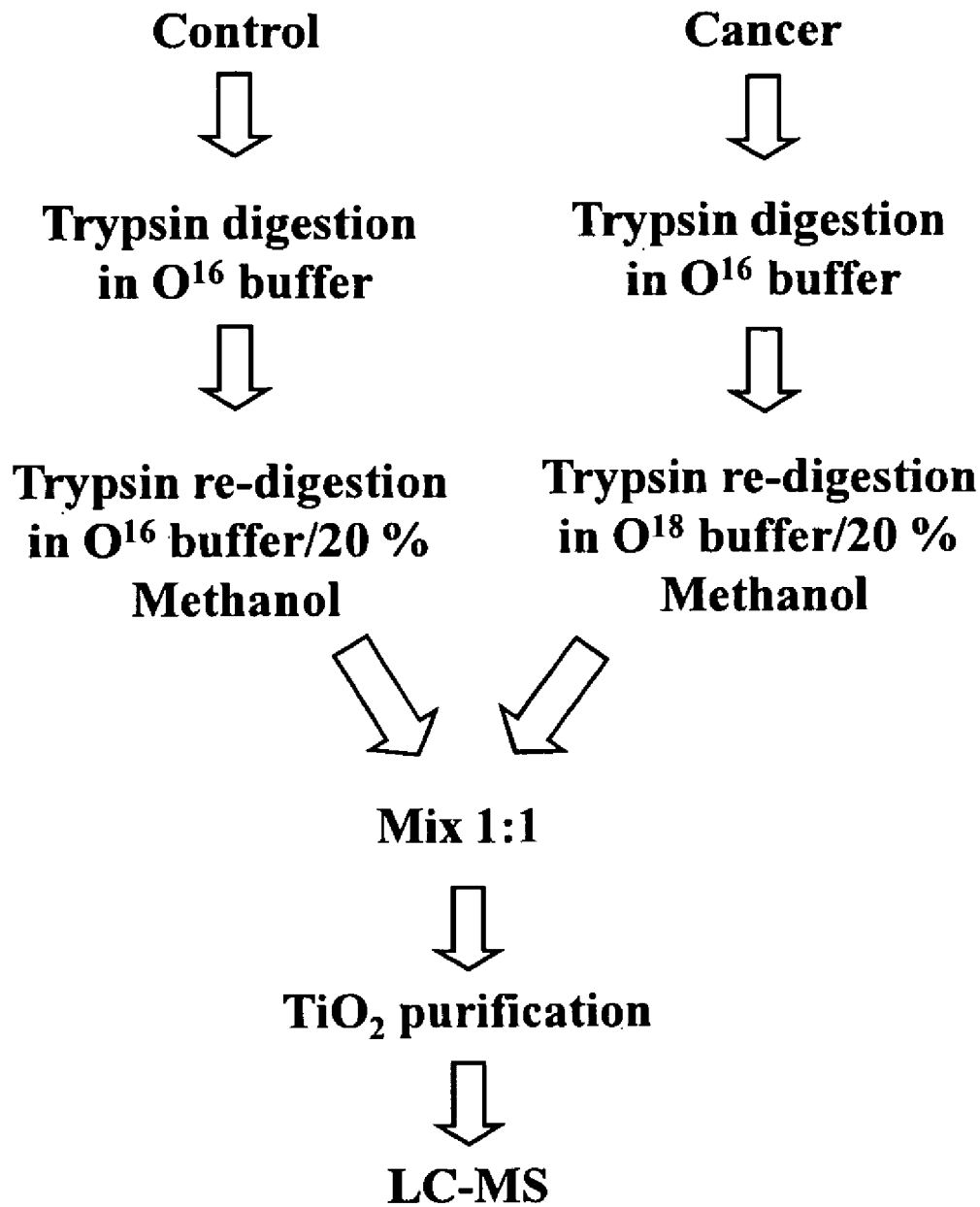
FIG. 7 outlines a strategy for identification of biomarkers of conditions associated with a change of sialylation status.

FIG. 7 outlines a strategy for identification of biomarkers of conditions associated with a change of sialylation status.

Equivalent samples from bladder cancer patients were labelled using $O^{18}$ to distinguish them from normal controls. The tryptic peptides were lyophilized and redissolved in $O^{18}$ buffer containing 2 µg trypsin and 20% methanol and incubated over night in 37° C.

Figure 8:
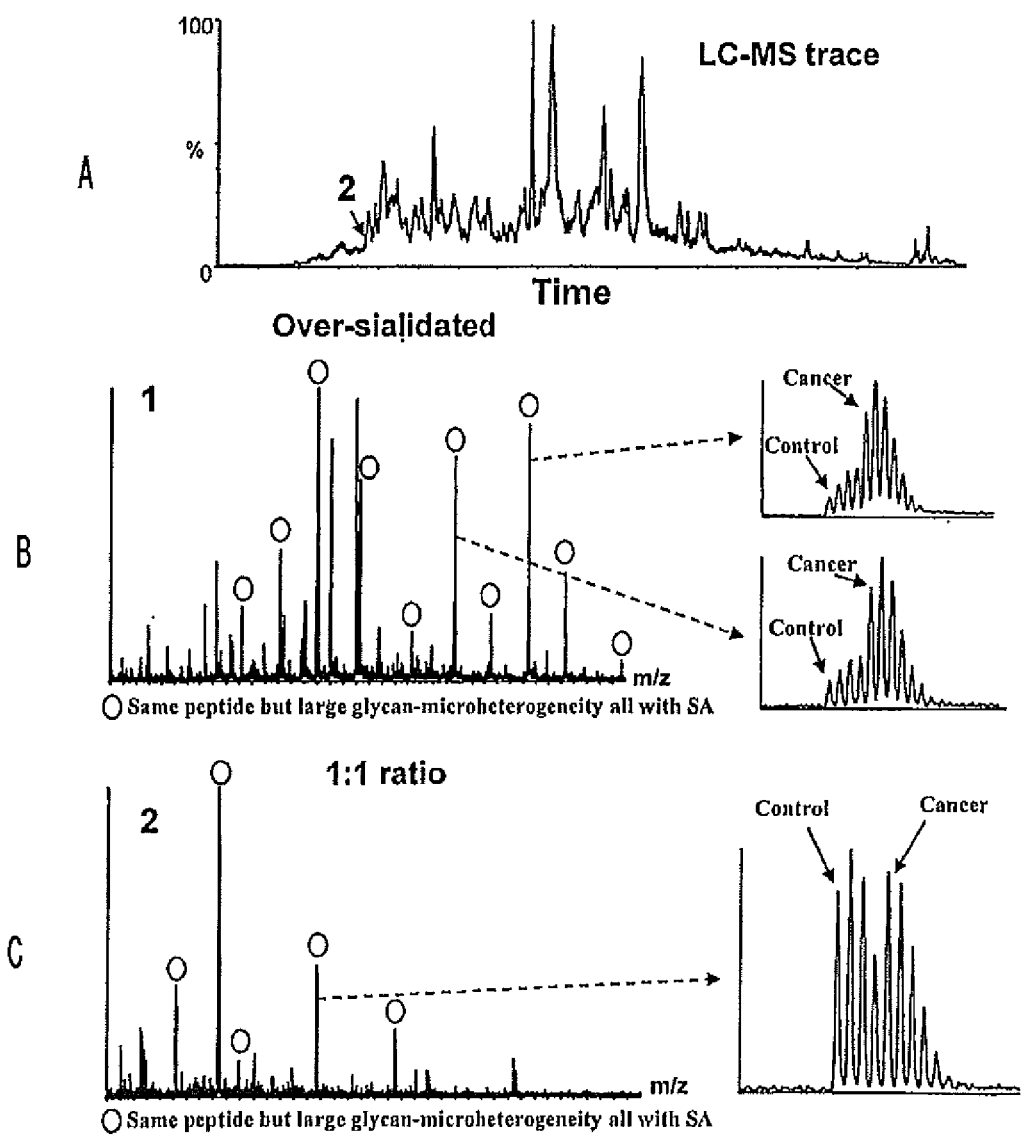
FIG. 8A shows LC-MSMS spectra of purified sialylated glycopeptides labeled with $O^{18}$ (bladder cancer) and $O^{16}$ (normal).
FIG. 8B shows MALDI mass spectra of purified sialylated glycopeptides labeled with $O^{18}$ (bladder cancer) and $O^{16}$ (normal) eluted from a reversed-phase LC-column at time 1.
FIG. 8C shows MALDI mass spectra of purified sialylated glycopeptides labeled with $O^{18}$ (bladder cancer) and $O^{16}$ (normal) eluted from a reversed-phase LC-column at time 2.

$O^{16}$- and $O^{18}$-labelled tryptic fragments were purified using the present methods. An LC-MS mass spectrum ion trace of the isolated sialylated fragments is shown in FIG. 8 (A). The $O^{16}$- and $O^{18}$-labelled sialylated tryptic fragments were then further analysed by LC-MSMS. FIG. 7(B) shows LC-MSMS spectra of peptides that elute from LC-column at the time labelled 1 in FIG. 8 (A). As shown, ten peptides were identified which are over-sialylated in the bladder cancer sample relative to control. FIG. 8(C) shows LC-MSMS spectra of peptides that elute from LC-column at the time labelled 2 in FIG. 8 (A). As shown, five peptides were identified that, while not over-sialylated, had increased glycan heterogeneity in bladder cancer samples.

7. Identification of Biomarkers of Bladder Cancer

Plasma from control and bladder cancer sample were prepared as described for example 6. $O^{16}$- and $O^{18}$-labelled sialylated tryptic fragments were prepared and isolated as described for example 6.

Identification of potential biomarkers is illustrated in FIG. 9. Purified sialic acid containing glycopeptides from plasma labelled with $O^{18}$ (cancer) and normal ($O^{16}$) were analyzed by LC-MS which is shown as an ion trace in FIG. 9 (A). FIG. 9 (B) shows the mass spectrum of the sialic acid containing glycopeptides that elutes from the reversed-phase LC-column at the time labelled with a circle. FIG. 9 (C) shows the mass spectrum of the triply charged sialic acid containing glycopeptide at m/z 1472.61 (control) and 1473.94 (cancer). The signal from the cancer is significantly higher than control indicating over-sialylation in cancer. The signal at m/z 1473.94 was selected for tandem MS and collision induced dissociation and the fragment ion spectrum is shown in FIG. 9 (D). From the masses of the fragments and the knowledge that N-linked glycans always have a common core structure ((N-acetylglucoseamine)$_2$(Mannose)$_3$) the mass of the peptide can be calculated and a putative composition of the glycan structure described. This glycan structure is shown in the inset in the upper right part of FIG. 9 (D). Monosaccharide symbols are indicated. After deglycosylation with N-glycosidase F (PNGaseF) which gives a mass increment of 1 Da for each N-linked glycosylation, the isotope distribution is as shown in FIG. 9 (E). As shown, a large increase in sialylation of the 1472.61 peptide is observed in the cancer sample. Upon collision induced dissociation this peptide is fragmented to give the fragment ion spectrum shown in FIG. 9 (F). From this fragment ion spectrum the sequence LVPVPITNATLDR (SEQ ID NO. 1) can be read, which belongs to Human Alpha-1-acid glycoprotein 2. The N in NAT is glycosylated. Accordingly, the invention further provides a biomarker of bladder cancer consisting of human alpha-1-acid glycoprotein 2 N-glycosylated at SEQ ID NO. 1. It will be readily understood that human alpha-1-acid glycoprotein 2 may be treated with peptidase or other enzymes such that the actual peptide observed in diagnosis or detection can be a fragment of the whole protein.

8. Validation of Identified Biomarkers

Potential biomarkers identified by the methods of the present invention can then be validated by repeating measurements described above using similar samples additional patients.

9. Specificity of Isolation Using Titanium Dioxide Stationary Phase for Phosphorylated Compared with Non-Phosphorylated Fragments Modified trypsin was from Promega (Madison, Wis., USA). Poros R2 and Poros Oligo R3 reversed phase material were from PerSeptive Biosystems (Framingham, Mass.). GELoader tips were from Eppendorff (Eppendorf, Hamburg, Germany). 2,5-Dihydroxybenzoic acid (DHB) was from Fluka (St. Louis, Mo.). 3M Empore C8 disk was from 3M Bioanalytical Technologies (St. Paul, Minn., USA). Syringe for HPLC loading (P/N 038030, N25/500—7C PKT 2) were from SGE (Victoria, Australia). The water was from a Milli-Q system (Millipore, Bedford, Mass.). Titanium dioxide beads were obtained from a disassembled $TiO_2$ cartridge (4.0 mm ID—5020-08520-5u-TiO2) purchased from GL sciences Inc, Japan. All other chemicals and reagents were of the highest grade commercially available.

Serum albumin (bovine), β-lactoglobulin (bovine), Carbonic anhydrase (bovine), β-casein (bovine), α-casein (bovine) and ovalbumin (chicken) were from Sigma (St. Louis, Mo., USA). Each protein was dissolved in 50 mM ammonium bicarbonate, pH 7.8 and treated with trypsin (1-2% w/w) at 37° C. for 12 hours.

Peptide mixture 1: Peptides originating from a tryptic digestion of 0.5 μmol of commercial α-casein.

Peptide mixture 2: Peptides originating from tryptic digestions of serum albumin, β-lactoglobulin, carbonic anhydrase, β-casein, α-casein and ovalbumin. Peptide mixture 2, ratio 1:1, 1:10 and 1:50, refer to a mixture of peptides originating from a tryptic digestion of 0.5 μmol of the phosphorylated proteins (β-casein, α-casein and ovalbumin) and 0.5, 5 and 25 μmol of the non-phosphorylated peptides (serum albumin, β-lactoglobulin and carbonic anhydrase), respectively.

$TiO_2$ microcolumns with a length of approximately 3 mm were packed in GELoader tips. A small plug of $C_8$ material was stamped out of a 3M Empore™ $C_8$ extraction disk using a HPLC syringe needle and placed at the constricted end of the GELoader tip. The $C_8$ disk serves only as a frit to retain the titanium dioxide beads within the GELoader tip. Note, that the solvent used for either washing or loading the sample onto the $TiO_2$ microcolumn contains organic solvent (50-80% $CH_3CN$), which abrogates adsorption of peptides to the $C_8$ material. The $TiO_2$ beads were suspended in 80% acetonitrile/ 0.1% TFA and an aliquot of this suspension (depending on the size of the column) was loaded onto the GELoader tip. Gentle air pressure created by a plastic syringe was used to pack the column as previously described.

The efficacy of four different procedures for selective binding of phosphorylated peptides was investigated. The first procedure (A) was adopted from the previously published method (41). In the following development (procedures A-D), peptide mixture 1 was used. (A) Peptides were loaded onto $TiO_2$ columns in 0.1 M acetic acid. The columns were washed with 20 μL 80% acetonitrile/0.1 M acetic acid and the bound peptides were eluted with 3 μL 250 mM ammonium bicarbonate, pH 9.0. An aliquot of the eluate (0.7 μL) was mixed with 0.3 μL 2% TFA and 0.5 μL DHB/PA matrix solution (2,5-Dihydroxybenzoic acid (20 g/L) in 50% acetonitrile, 1% phosphoric acid) directly on the MALDI target. (B) Same procedure as in (A) was used, with the exception that the peptides were eluted with $NH_4OH$, pH 10.5. (C) The peptides were loaded onto the $TiO_2$ columns in 0.1% TFA and the columns were washed first with 10 μL of the DHB solution (2,5-Dihydroxybenzoic acid (20 mg/mL) in 50% acetonitrile) and then with 10 μL 80% acetonitrile/0.1% TFA, before the bound peptides were eluted using 3 μL $NH_4OH$, pH 10.5. (D) The peptides were loaded onto the $TiO_2$ column in DHB solutions of different concentration (1-350 mg/mL in 80% acetonitrile/0.1% TFA). The columns were washed with 10 μL of the DHB solution and 20 μL 80% acetonitrile/0.1% TFA. The bound peptides were eluted using 3 μL $NH_4OH$, pH 10.5.

Selective adsorption of phosphorylated peptides relative to non-phosphorylated peptides was demonstrated using a series of organic acids solutions as loading/washing solvents. $TiO_2$ microcolumns were loaded with peptide mixture 2 (ratio 1:1). The peptides were loaded onto the $TiO_2$ microcolumns in a 0.13 M solution of one of the following acids in 1:1 (v/v) $H_2O/CH_3CN$ with 0.1% TFA: phosphoric acid, benzoic acid, cyclohexane-carboxylic acid, phthalic acid, salicylic acid, or 2,5-dihydroxybenzoic acid. In case of acetic acid, TFA was omitted from the solution. After loading the peptides onto the $TiO_2$ columns, they were washed with 10 μL 50% acetonitrile/0.1% TFA. Each column was eluted with 3 μL $NH_4OH$, pH 10.5. Each eluate was purified on a poros oligo R3 microcolumn (see below) prior to MALDI MS analysis. For LC-ESI-MSMS analysis the eluted peptides were purified by Poros Oligo R3RP material and eluted by 50% acetonitrile, partly dried and diluted to 13 μL in 0,5% acetic acid.

Custom-made chromatographic reversed-phase microcolumns used for desalting and concentration of peptides were prepared using GELoader tips, as described in details earlier (44,45). The eluates from the $TiO_2$ microcolumns were diluted in formic acid to a final concentration of 5%, and applied onto poros oligo R3 micro-columns using gentle air pressure. The columns were washed with 20 μL 0.1% TFA. The retained peptides were eluted using 0.5 μL DHB/PA matrix solution directly onto the MALDI target.

For comparison, IMAC purification of phosphorylated peptides was performed according to (46) with minor changes. Briefly, 40 μL iron-coated PHOS-select™ metal chelate beads (Sigma) were washed 2 times in 100 μL washing/loading solution (0.25 M acetic acid/30% acetonitrile) and resuspended in 40 μL of washing/loading solution. An aliquot of this solution (20 μL) was incubated with the peptide solution in a total volume of 40 μL of washing/loading solution for 30 min with constant rotating. After incubation, the solution was loaded onto a constricted GELoader tip and a gentle air pressure was used to pack the beads. Subsequently the beads were washed extensively with the washing/loading solution. The bound peptides were eluted using 3 μL $NH_4OH$, pH 10,5 and desalted using poros R3 microcolumns prior to MALDI MS analysis (as described above).

Initially, the procedure was performed using tryptic peptides originating from α-casein (i.e. peptide mixture 1, see material and methods). Commercial α-casein consists of α-casein-S1 and α-casein-S2 and the preparations are usually contaminated with traces of β-casein and Statmin. A list of the theoretical tryptic phosphorylated peptides derived from α- and β-caseins and their molecular masses, is shown in Table 1. Evaluation of the phosphorylated peptide binding selectivity of the $TiO_2$ microcolumns and development of washing/ elution conditions was performed by comparing the relative intensities of the non-phosphorylated tryptic peptides with those of the phosphorylated peptides.

Figure 10:
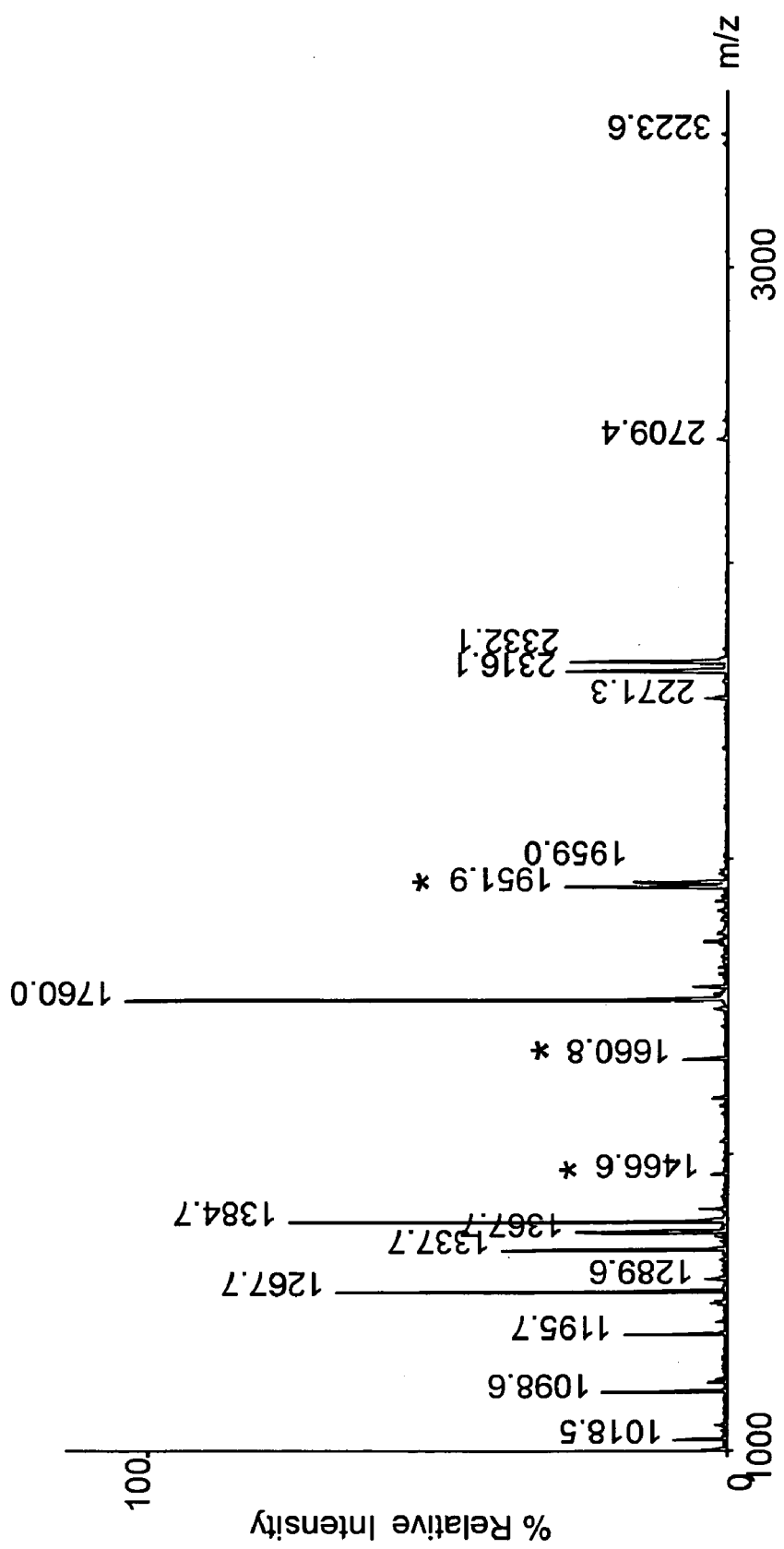
FIG. 10A shows MALDI mass spectra obtained from peptide mixture 1 without $TiO_2$ enrichment.
FIG. 10B shows MALDI mass spectra obtained from peptide mixture 1 enriched by $TiO_2$ using acetic acid as loading buffer and $NH_4HCO_3$ pH 9.0 as elution buffer.
FIG. 10C shows MALDI mass spectra obtained from peptide mixture 1 using $NH_4HCO_3$ pH 10.5 as elution buffer.
FIG. 10D shows MALDI mass spectra obtained from peptide mixture 1 enriched by $TiO_2$ using 0.1% TFA as loading buffer and $NH_4OH$ pH 10.5 as elution buffer.
Figure 10:
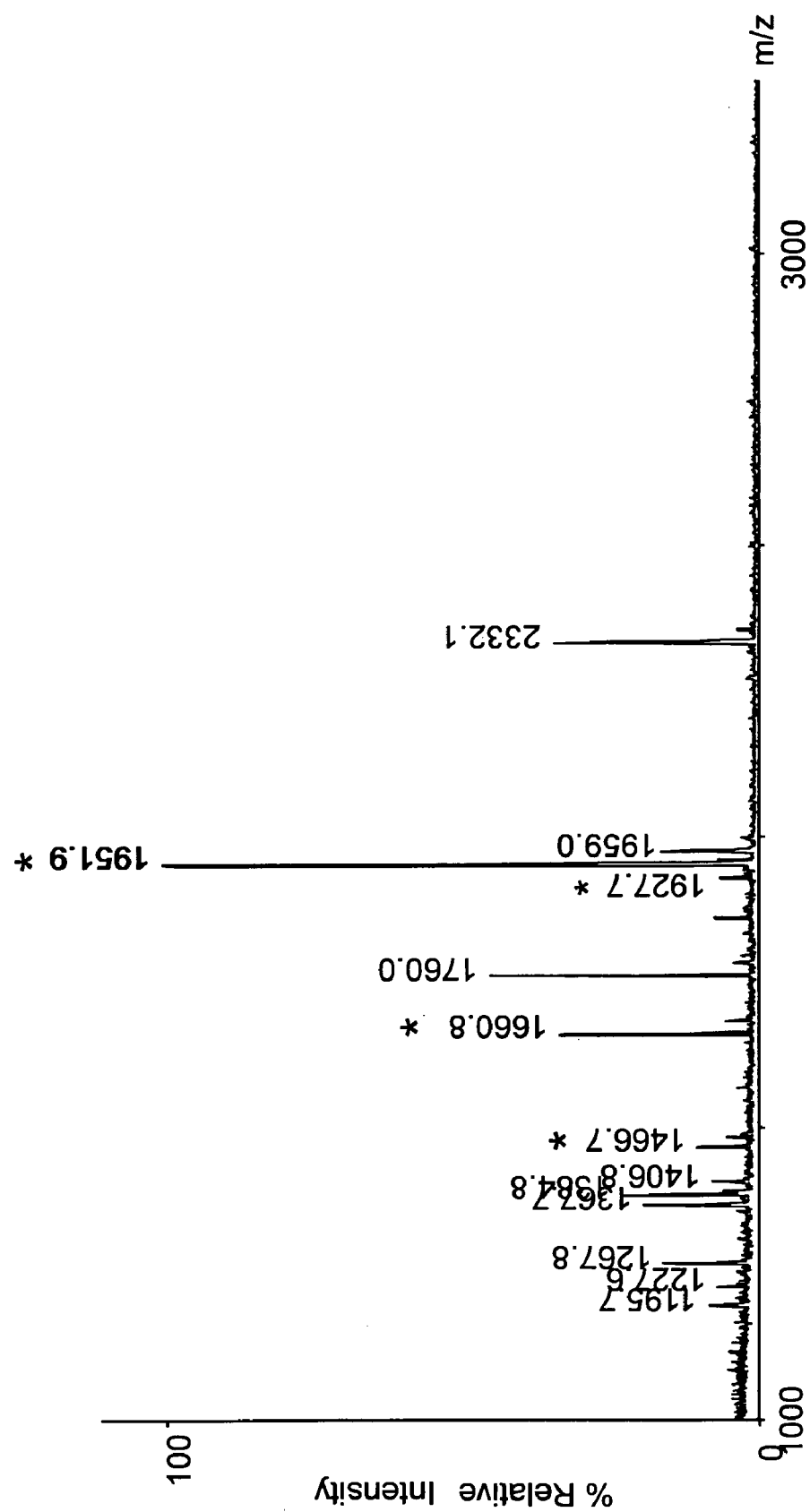
Figure 10:
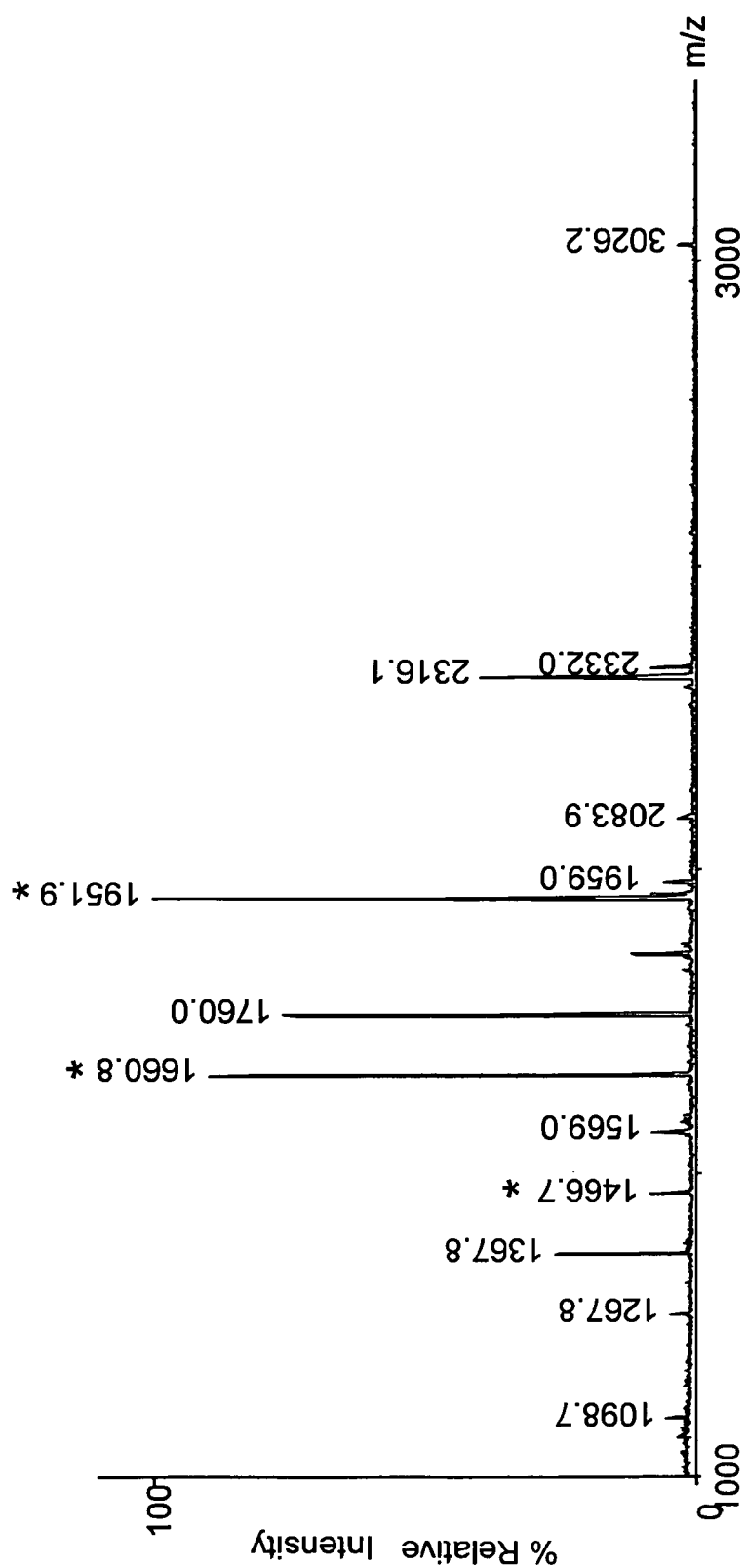
Figure 10:
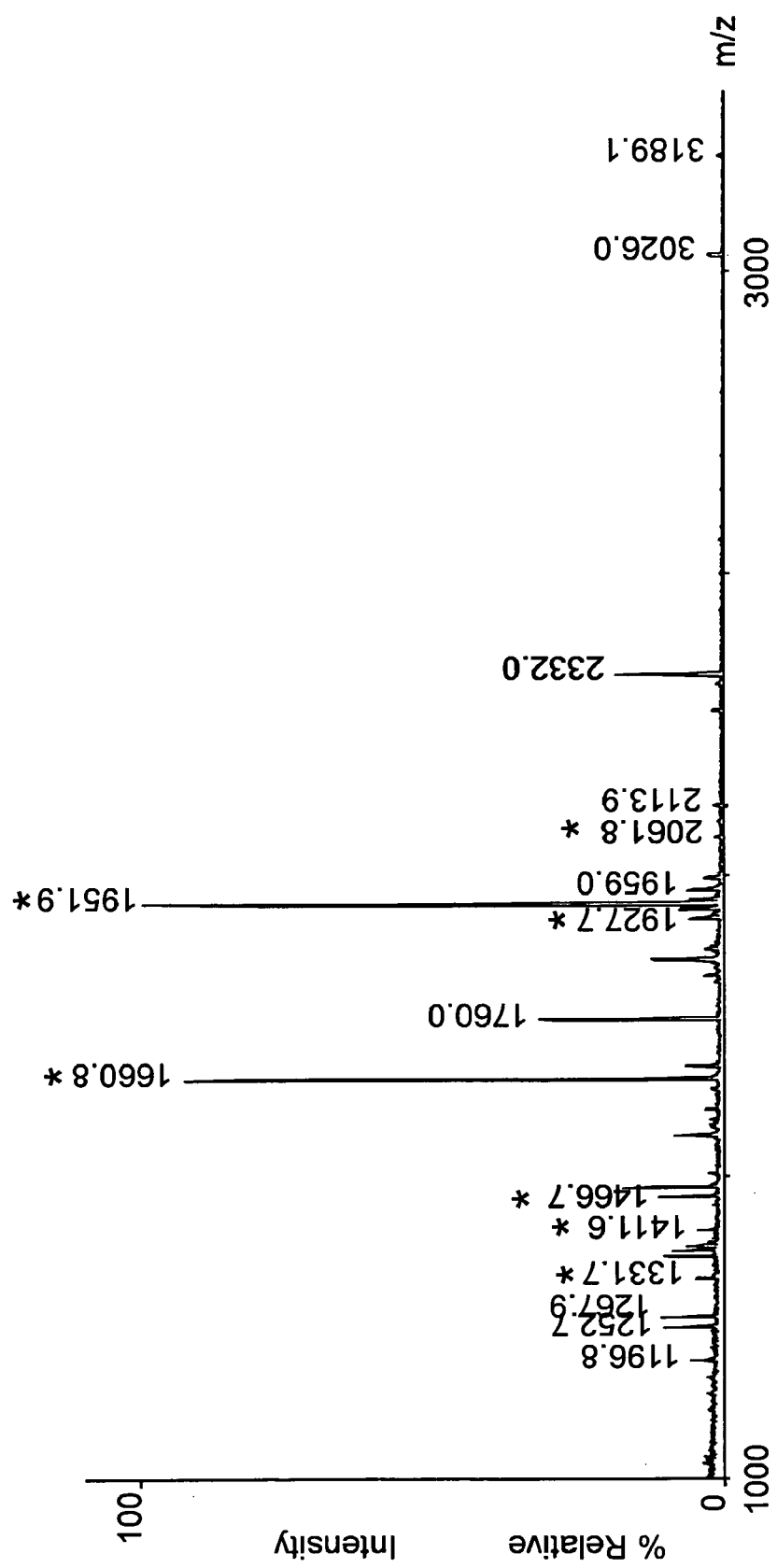

A direct analysis a tryptic digestion of 0.5 μmol of commercial □-casein by MALDI MS using a dried droplet sample preparation, in which the peptide mixture is mixed with 0.1% TFA and DHB matrix solution (including 1% phosphoric acid), results in detection of a few of the theoretical phosphorylated peptides (FIG. 10 A, marked with asterisks).

The MALDI MS spectrum obtained from the $TiO_2$ enrichment of phosphorylated peptides from peptide mixture 1, using the purification conditions as described by Pinkse et al. (41) (elution with 250 mM ammonium bicarbonate, pH 9.0), is shown in FIG. 10 B. A significant number of non-phosphorylated peptides are observed together with 4 phosphorylated peptides (marked with asterisks). No signals are observed from the multiphosphorylated peptides.

After elution with 250 mM ammonium bicarbonate, pH 9.0, the same microcolumn was subsequently eluted with 3 μL $NH_4OH$, pH 10.5 and the MALDI MS analysis of 0.7 μL of this solution yielded very abundant phosphorylated peptides (FIG. 10 C), thereby demonstrating that elution with pH 9 only release a small fraction of the adsorbed phosphorylated peptides, whereas pH 10.5 elutes most of the bound phosphorylated peptides. Subsequent elution using higher pH did not result in further improvement in the recovery of phosphorylated peptides from the TiO$_2$ microcolumns.

In previous purification procedures for enrichment of phosphorylated peptides using both TiO$_2$ and IMAC 0.1-0.25 M acetic acid (pH 2.7-2.9) has been used as the loading buffer. The reason for choosing this pH value in the loading is to ensure that the acidic residues in the peptides are neutral, whereas the pKa$_1$ value of phosphoric acid is 1.8 and therefore the phosphate group will still have a negative charge at pH 2.9. However, a significant amount of non-phosphorylated acidic peptides binds to either IMAC or TiO$_2$ under those conditions (35, 41). The substitution of an alkyl group onto an acidic phosphate oxygen atom increases the acidity e.g., the pKa$_1$ value of phosphoric acid decreases to 1.1 upon methylation (i.e., CH$_3$OPO(OH)$_2$) (47). Thus, we anticipate that the pKa$_1$ value of the phosphate group also decrease when it is linked to a peptide. Therefore 0.1% TFA, which has a pH value of 1.9 was used in the following buffers for the purification of phosphorylated peptides using TiO$_2$.

A TiO$_2$ microcolumn was loaded with peptide mixture 1 in 0.1% TFA. After washing with 80% acetonitrile/0.1% TFA, the phosphorylated peptides were eluted from the TiO$_2$ with 3 μL NH$_4$OH, pH 10.5, and the MALDI MS analysis of 0.7 μL of this solution resulted in the MALDI spectrum shown in FIG. 10 D. Here, the intensity of the phosphorylated peptides increased relative to the non-phosphorylated peptides, indicating a more selective enrichment of phosphorylated peptides when 0.1% TFA was used as loading buffer.

Elution of phosphorylated peptides from immobilized metal affinity chromatography (IMAC) material using the DHB matrix solution has previously been shown to increase the recovery of some phosphorylated peptides from this chromatographic material (48). Since the binding of phosphorylated peptides to TiO$_2$ is attributed to its ion-exchange properties (41), which is similar to the binding observed in IMAC experiments, we attempted to elute the phosphorylated peptides with the DHB matrix solution.

Figure 11:
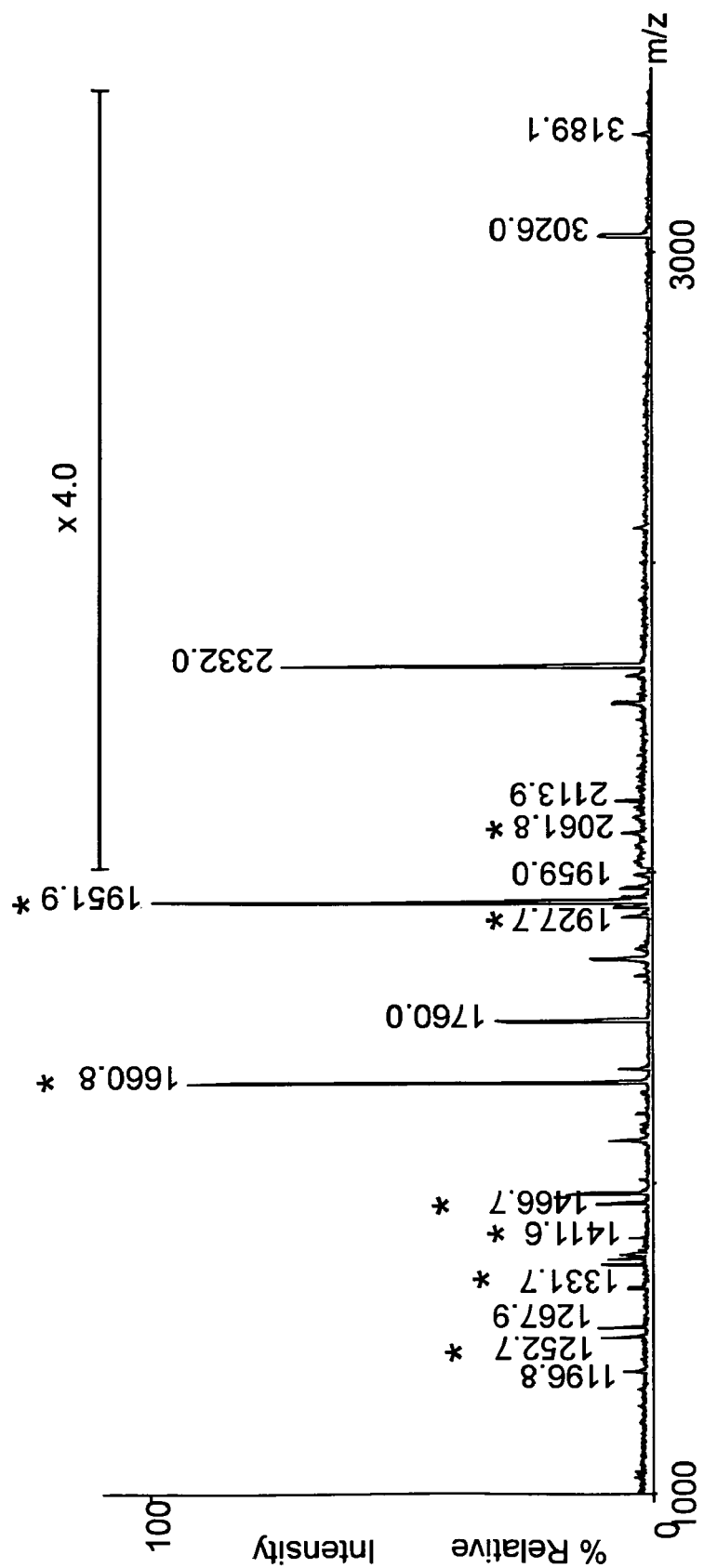
FIG. 11A shows MALDI mass spectra obtained from peptide mixture 1 enriched by $TiO_2$ using 0.1% TFA as loading buffer and $NH_4OH$, pH 10.5 as elution buffer.
FIG. 11B shows MALDI mass spectra obtained from peptide mixture 1 enriched by $TiO_2$ using 0.1% TFA as loading buffer and acidic DHB solution as elution buffer.
FIG. 11C shows MALDI mass spectra obtained from peptide mixture 1 subsequent elution with $NH_4OH$, pH 10.5.
FIG. 11D shows MALDI mass spectra obtained from peptide mixture 1 enriched by $TiO_2$ using acidic DHB solution as loading buffer and $NH_4OH$ pH 10.5 as elution buffer.
Figure 11:
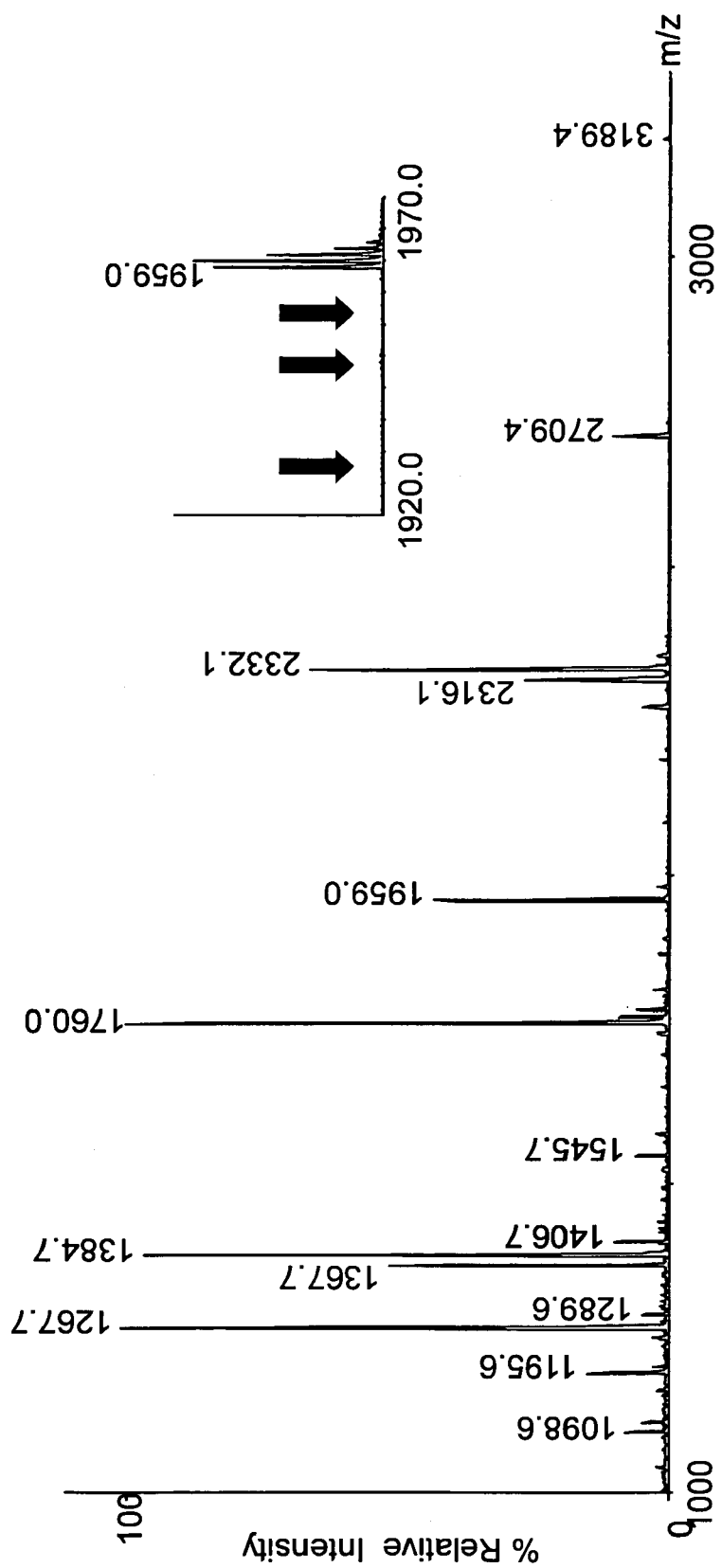
Figure 11:
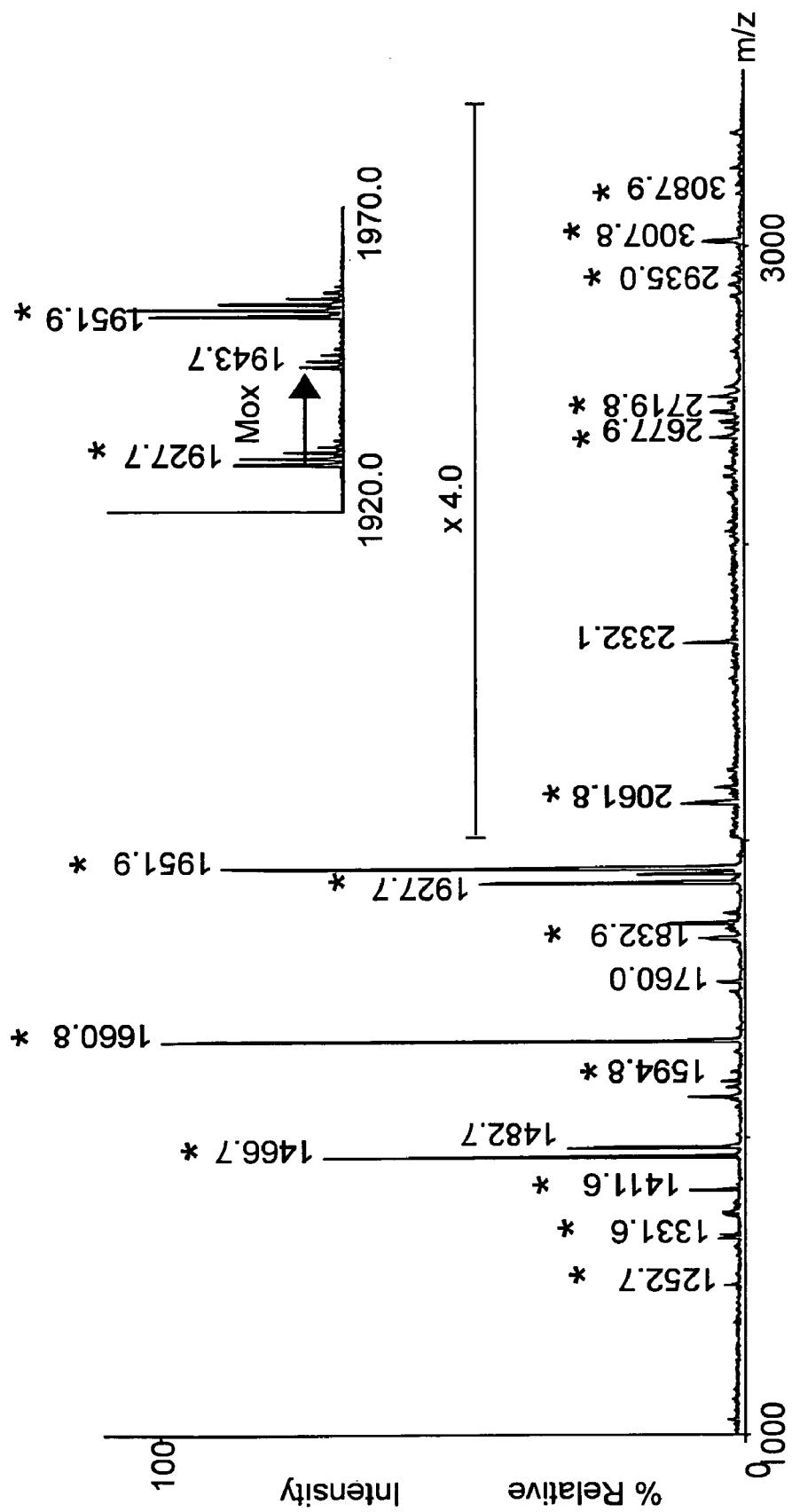
Figure 11:
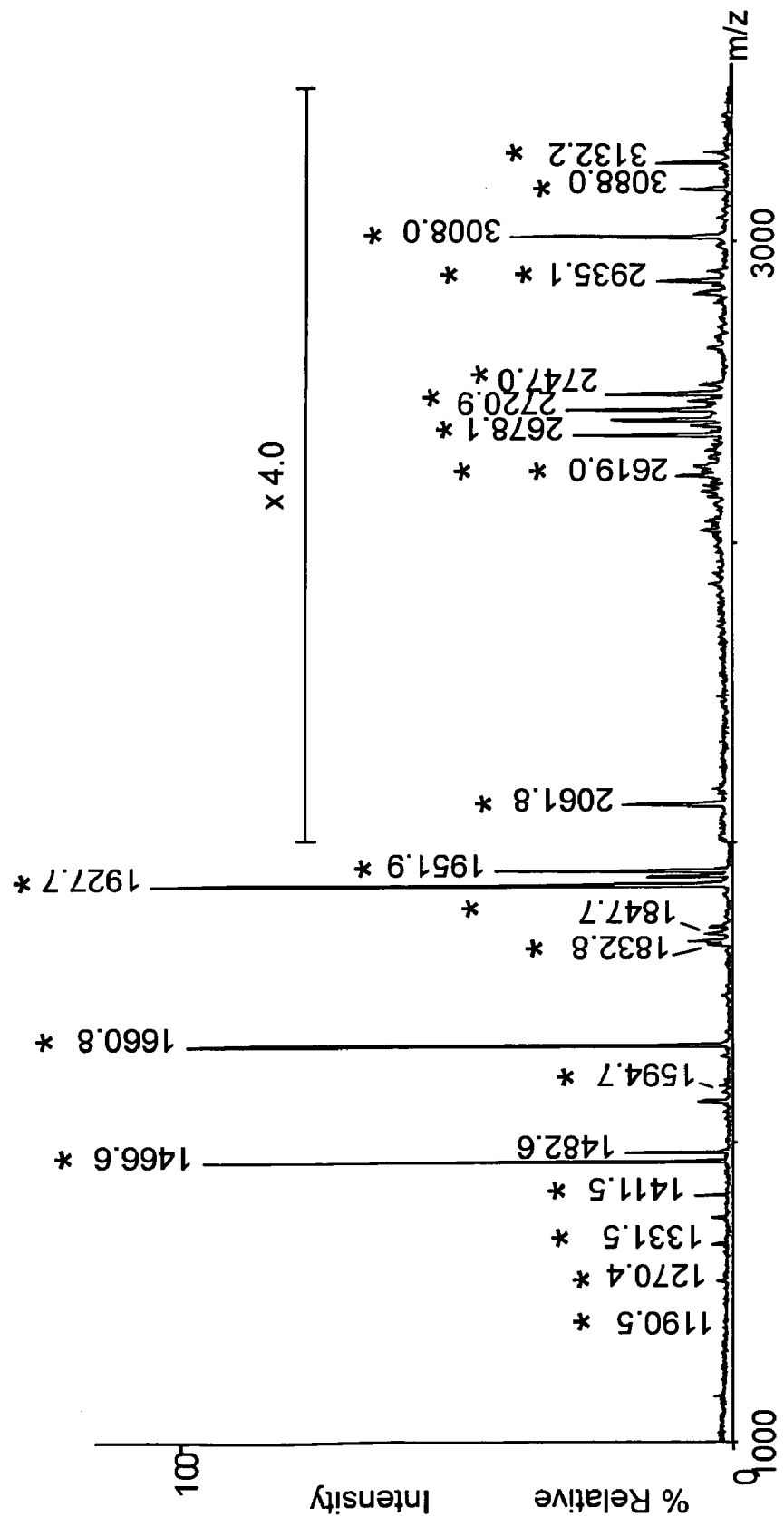

The enrichment of phosphorylated peptides from peptide mixture 1 using TiO$_2$ loaded in 0.1% TFA, followed by washing in 80% acetonitrile/0.1% TFA and elution of the phosphorylated peptides with pH 10.5 is shown in FIG. 11 A. Peptides from peptide mixture 1 were loaded onto a new TiO$_2$ microcolumn, as above, however, after washing with 80% acetonitrile/0.1% TFA, the peptides were eluted directly onto the MALDI target using DHB matrix solution (20 mg/mL in 50% acetonitrile/0.1% TFA). Phosphoric acid (1%) was added after the elution and the eluate was subsequently analysed by MALDI MS (FIG. 11 B). Only non-phosphorylated peptides were detected, as illustrated by the insets in the Figure, where arrows indicate the expected masses of some of the phosphorylated peptides. Thus, all phosphorylated peptides were retained by the TiO$_2$ resin after elution with the DHB matrix solution. Subsequent elution from the same column with NH$_4$OH, pH 10.5 recovered a larger number of phosphorylated peptides (FIG. 11 C, marked with asterisks) compared to the procedure where the column was only washed with 80% acetonitrile/0.1% TFA (FIG. 11 A). In addition, a surprisingly low abundance and number of non-phosphorylated peptides were observed (4 in total). In IMAC, DHB is sufficient to displace the bound phosphorylated peptides, whereas the interaction between TiO$_2$ and the phosphate group appears to be much stronger and cannot be dissociated by DHB. However, acidic non-phosphorylated peptides can be displaced from TiO$_2$ by competitive binding of DHB thereby increasing the selective binding of phosphorylated peptides.

Since DHB is capable of displacing non-specifically bound acidic peptides from the TiO$_2$ microcolumn, another experiment was performed, in which peptide solution 1 was applied onto a TiO$_2$ microcolumn in 20 μL of a DHB matrix solution (20 mg/mL in 80% acetonitrile/0.1% TFA). The column was subsequently washed with 10 μL of the DHB solution and 20 μL of 80% acetonitrile/0.1% TFA, respectively. The bound peptides were eluted with 3 μL NH$_4$OH, pH 10.5 and 0.7 μL of this solution were mixed with 0.3 μL 2% TFA and 0.5 μL DHB/PA matrix solution on the MALDI target. The resulting MALDI peptide mass map is shown in FIG. 11 D. Here a total of 20 signals were detected, which all represent phosphorylated peptides and no significant signals were detected from non-phosphorylated peptides. Note the absence of the signal at m/z 1760. The flow-through from the loading was collected directly on the MALDI target and analysed for the presence of phosphorylated peptides. Here only non-phosphorylated peptides could be detected.

The two very low abundant ions at m/z 1190.5 and m/z 1270.4 carrying one and two phosphate groups, respectively, originates from the contaminating protein statmin as verified by MALDI tandem MS.

Figure 12:
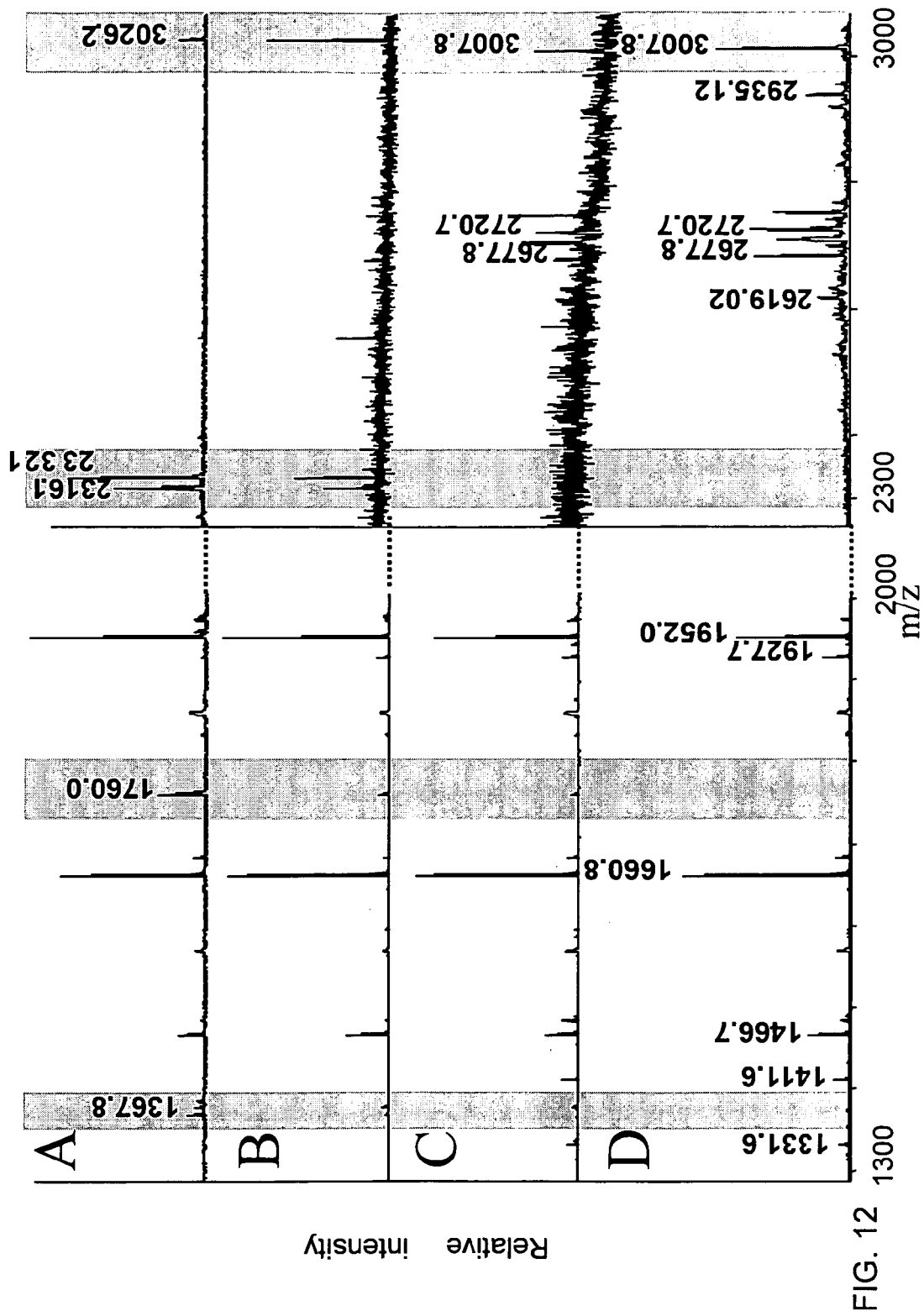
FIG. 12A shows MALDI mass spectrum of $TiO_2$ enriched peptides from peptide mixture 1 without DHB.
FIG. 12B shows MALDI mass spectrum of $TiO_2$ enriched peptides from peptide mixture using 1 mg/ml DHB in 80% acetonitrile and 0.1% TFA.
FIG. 12C shows MALDI mass spectrum of $TiO_2$ enriched peptides from peptide mixture using 10 mg/ml DHB in 80% acetonitrile and 0.1% TFA.
FIG. 12D shows MALDI mass spectrum of $TiO_2$ enriched peptides from peptide mixture using 20 mg/ml DHB in 80% acetonitrile and 0.1% TFA.
Figure 13A:
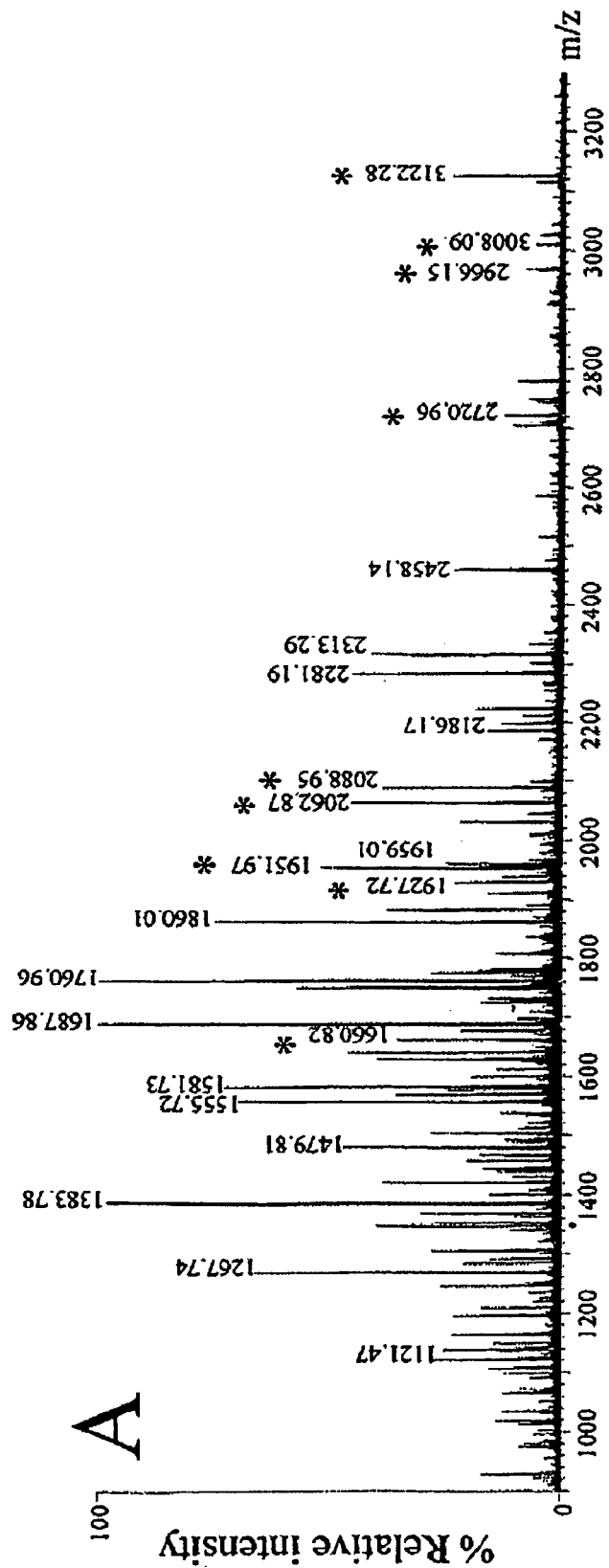
FIG. 13A shows MALDI mass spectrum of phosphorylated peptides from mixture 2 obtained without $TiO_2$ enrichment.
Figure 13B:
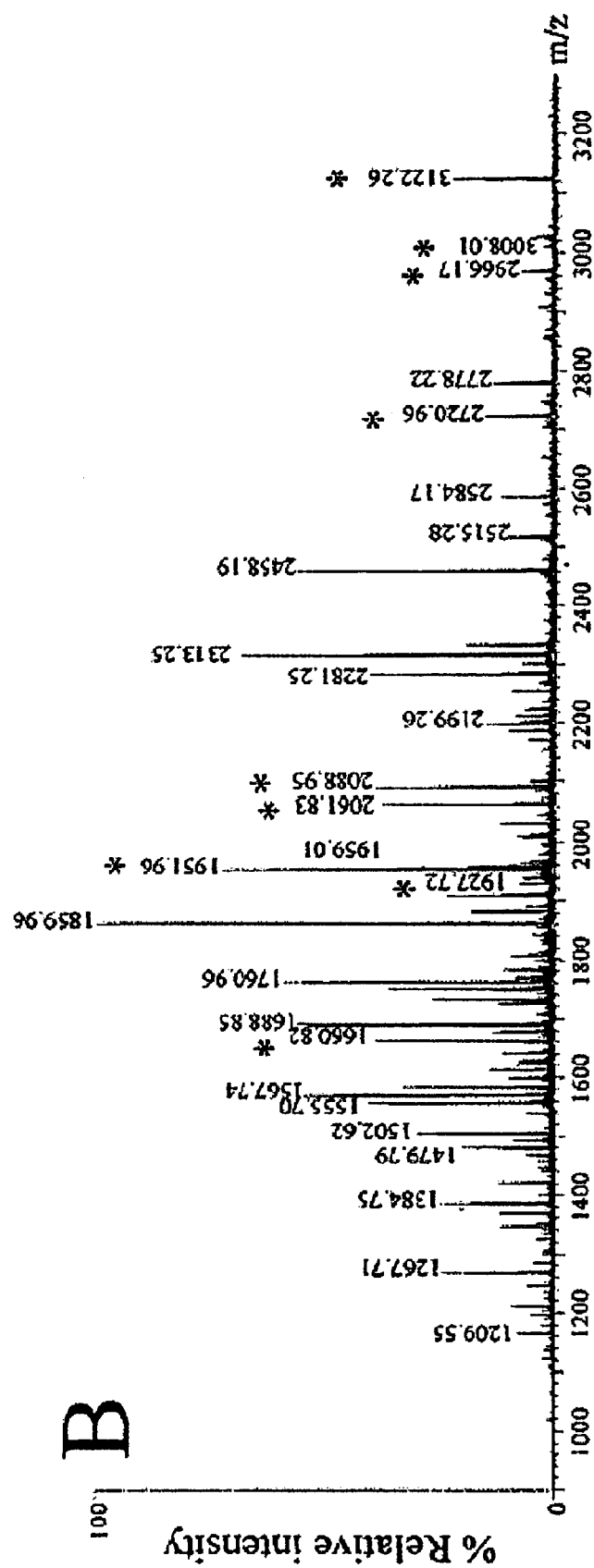
FIG. 13B shows MALDI mass spectrum of phosphorylated peptides from mixture 2 enriched by $TiO_2$ using acetic acid as loading buffer.
Figure 13C:
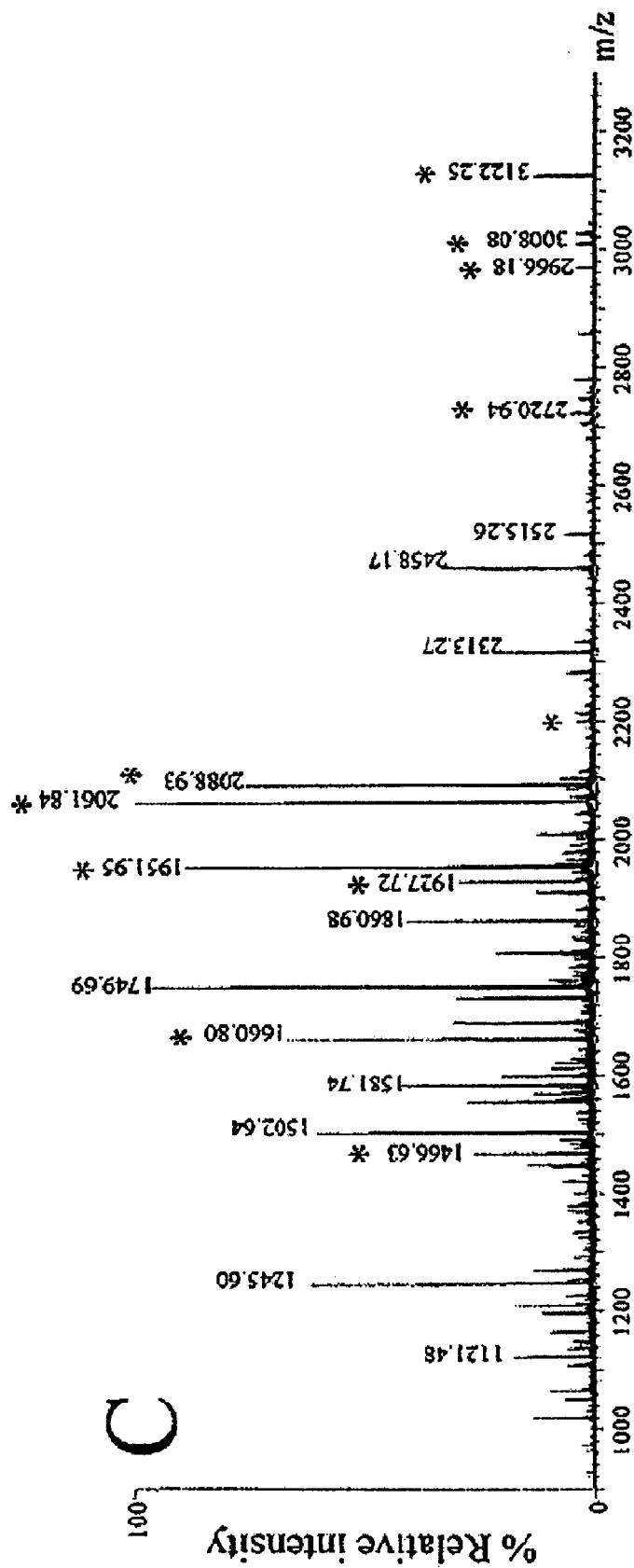
FIG. 13C shows MALDI mass spectrum of phosphorylated peptides from mixture 2 enriched by $TiO_2$ using 0.1% TFA as loading buffer.
Figure 13D:
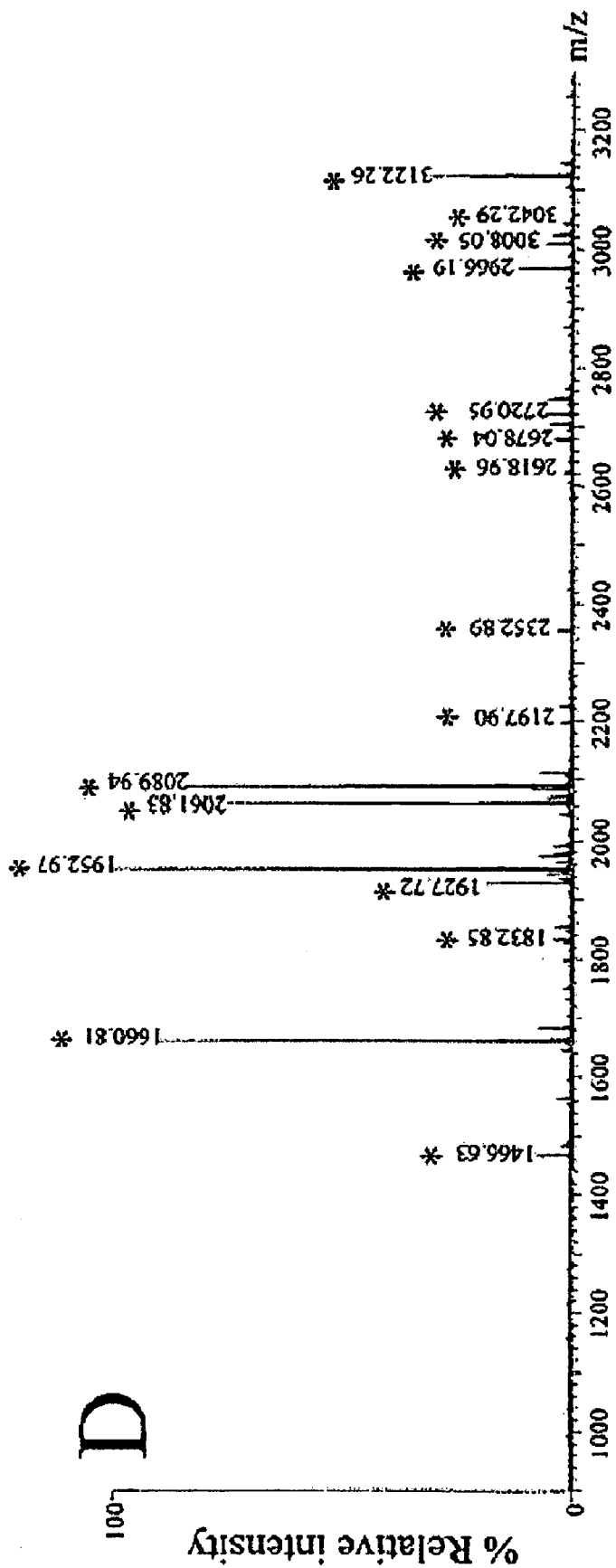
FIG. 13D shows MALDI mass spectrum of phosphorylated peptides from mixture 2 enriched by $TiO_2$ using DHB (300 mg/ml) as loading buffer.

The concentration of DHB in the loading buffer affects the adsorption of non-phosphorylated peptides onto TiO$_2$. A series of experiments were performed using peptide mixture 1 and different concentrations of DHB in the loading buffer. Peptides from peptide mixture 1 were loaded onto equal length TiO$_2$ microcolumns in 0, 1, 10 and 20 mg/ml DHB (in 80% acetonitrile/0.1% TFA), respectively. The MALDI mass spectra covering the mass range 1000-2000 Da and 2300-3100 Da obtained from the elution with NH$_4$OH, pH 10.5, are shown in FIG. 12 A-D. This figure shows that the number of non-phosphorylated peptides decreases with the increasing concentration of DHB. In the experiment where the peptides were loaded in 80% acetonitrile/0.1% TFA alone, 5 signals from non-phosphorylated peptides are observed (FIG. 12 A, shaded areas). Inclusion of as little as 1 mg/mL of DHB, significantly decrease the abundance of these peptides. A further increase in the concentration of DHB to 20 mg/mL completely abrogates the adsorption of these non-phosphorylated peptides to TiO$_2$, as evident by their absence in the mass spectra. Interestingly the multiphosphorylated peptides in the m/z 2300-3100 ranges are only observed at DHB concentrations above 10 mg/mL. This indicates a pronounced suppression of the ionization of multiphosphorylated peptides in the presence of non-phosphorylated peptides The previous analyses using TiO$_2$ microcolumns were performed with peptides derived from a single protein (and low amounts of contaminating proteins). Here, a semi complex peptide mixture (peptide mixture 2 (ratio 1:1), see material and methods) were analysed by TiO$_2$ microcolumns using the new procedure. In this mixture a total of minimum 18 phosphorylated peptides (listed in Table 1) are present. The theoretical number of peptides derived from the 6 proteins by tryptic digestion is 296, allowing for one 1 missed cleavage and a mass range of 700-3500 Da. Peptides from peptide mixture 2 (ratio 1:1) were analysed by MALDI MS using the normal dried droplet method (FIG. 13 A). Here only 9 phosphorylated peptides could be detected (marked with asterisks) probably due to the ion suppression effect caused by the non-phosphorylated peptides. A similar amount of peptides from peptide mixture 2 (ratio 1:1) were applied onto a TiO$_2$ microcolumn using the procedure described by Pinkse et al. (41). The peptides were eluted off the column using 3 μL NH$_4$OH pH 10.5 and the eluted peptides were subsequently purified using a Poros Oligo R3 micro-column, from which the peptides were eluted directly onto the MALDI target using the DHB/PA matrix solution. The resulting MALDI MS peptide mass map is shown in FIG. 13 B. Here the same 9 phosphorylated peptides could be detected, however, a significant amount of non-phosphorylated peptides are observed in the eluate. The experiment was repeated using 0.1% TFA instead of 0.1 M acetic acid in the loading procedure. The resulting MALDI MS peptide mass map is shown in FIG. 13 C. Here a significant amount of non-phosphorylated peptides are still observed in the eluate but the relative signal intensity of the phosphorylated peptides is markedly increased compared to loading in acetic acid. In addition, 2 extra phosphorylated peptides could be detected. Loading peptide mixture 2 (ratio 1:1) in DHB (300 mg/mL in 80% acetonitrile/0.1% TFA) resulted in the selective purification of phosphorylated peptides with hardly any "contamination" with non-phosphorylated peptides (FIG. 13 D). Here a total of 16 phosphorylated peptides are detected. The purification of the eluate using Poros R3 results in loss of at least 2 phosphorylated peptides (m/z 1331.5 and m/z 1411.5), since they do not bind to this reversed phase material. However, these were detected by MALDI MS after purification of the flow-through from the R3 column by using a graphite micro-column.

The absolute abundance of the phosphorylated peptides was markedly increased when using the DHB as loading buffer compared to either acetic acid or TFA, despite the same amount of starting material. The same observation was made in all the other experiments performed in this study. This indicates a more efficient ionization for phosphorylated peptides in the absence of non-phosphorylated peptides.

Figure 14:
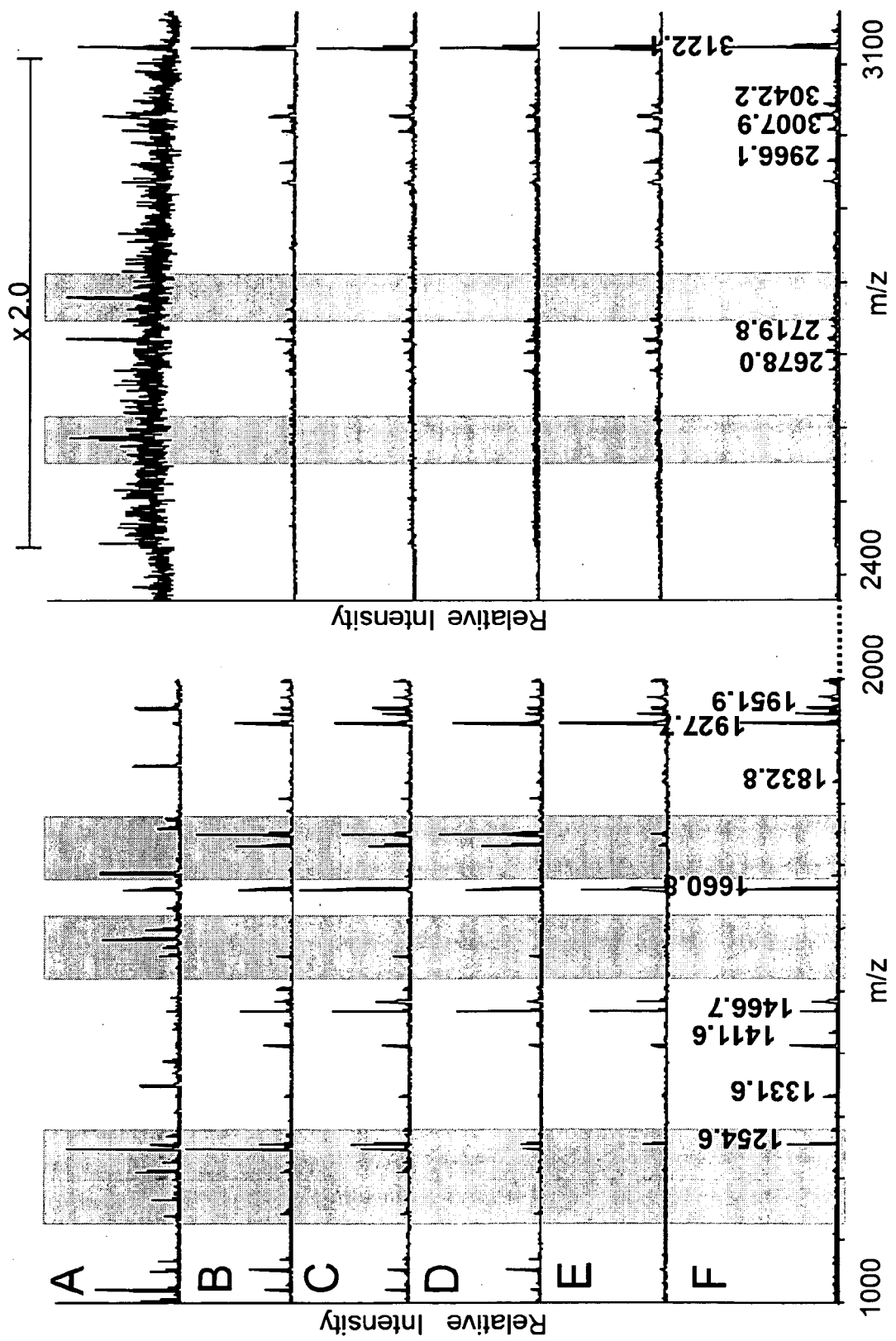
FIG. 14A shows MALDI mass spectrum of phosphorylated peptides from peptide mixture 2 obtained without $TiO_2$ enrichment.
FIG. 14B shows MALDI mass spectrum of phosphorylated peptides from peptide mixture 2 obtained from $TiO_2$ enrichment in a loading buffer containing 10 mg/ml DHB.
FIG. 14C shows MALDI mass spectrum of phosphorylated peptides from peptides mixture 2 obtained from $TiO_2$ enrichment in a loading buffer containing 20 mg/ml DHB.
FIG. 14D shows MALDI mass spectrum of phosphorylated peptides from peptide mixture 2 obtained from $TiO_2$ enrichment in a loading buffer containing 50 mg/ml DHB.
FIG. 14E shows MALDI mass spectrum of phosphorylated peptides from peptide mixture 2 obtained from $TiO_2$ enrichment in a loading buffer containing 100 mg/ml DHB.
FIG. 14F shows MALDI mass spectrum of phosphorylated peptides from peptide mixture 2 obtained from $TiO_2$ enrichment in a loading buffer containing 200 mg/ml DHB.

The effect of the inclusion of DHB in the loading and washing procedure for complex mixtures was investigated using peptide mixture 2 (ratio 1:1). Peptides from peptide mixture 2 (ratio 1:1) were applied onto TiO$_2$ micro-columns of the same length in 0, 10, 20, 50, 100 and 200 mg/mL DHB (in 80% acetonitrile/0.1% TFA), respectively. The resulting MALDI peptide mass maps obtained from 0.7 μL of each of the elutions (performed with 3μL NH$_4$OH pH 10.5) is shown in FIG. 14 A-F. The absence of DHB causes a high number of non-phosphorylated peptides to bind to the columns. The number of non-phosphorylated peptides decreases with the increasing concentration of DHB up to 200 mg/mL, where no non-phosphorylated peptides are observed. In addition, also here the multi-phosphorylated peptides are more clearly detected when higher concentration of DHB is used, probably due to decreased ion suppression effect. This clearly indicates that the more complex the sample is the higher concentration of DHB is needed to exclude the binding of non-phosphorylated peptides. For very complex samples a DHB concentration of 300-400 mg/mL (close to a saturated solution) is preferred.

10. Comparison of the Performance with IMAC for Semi-Complex Samples

Figure 15:
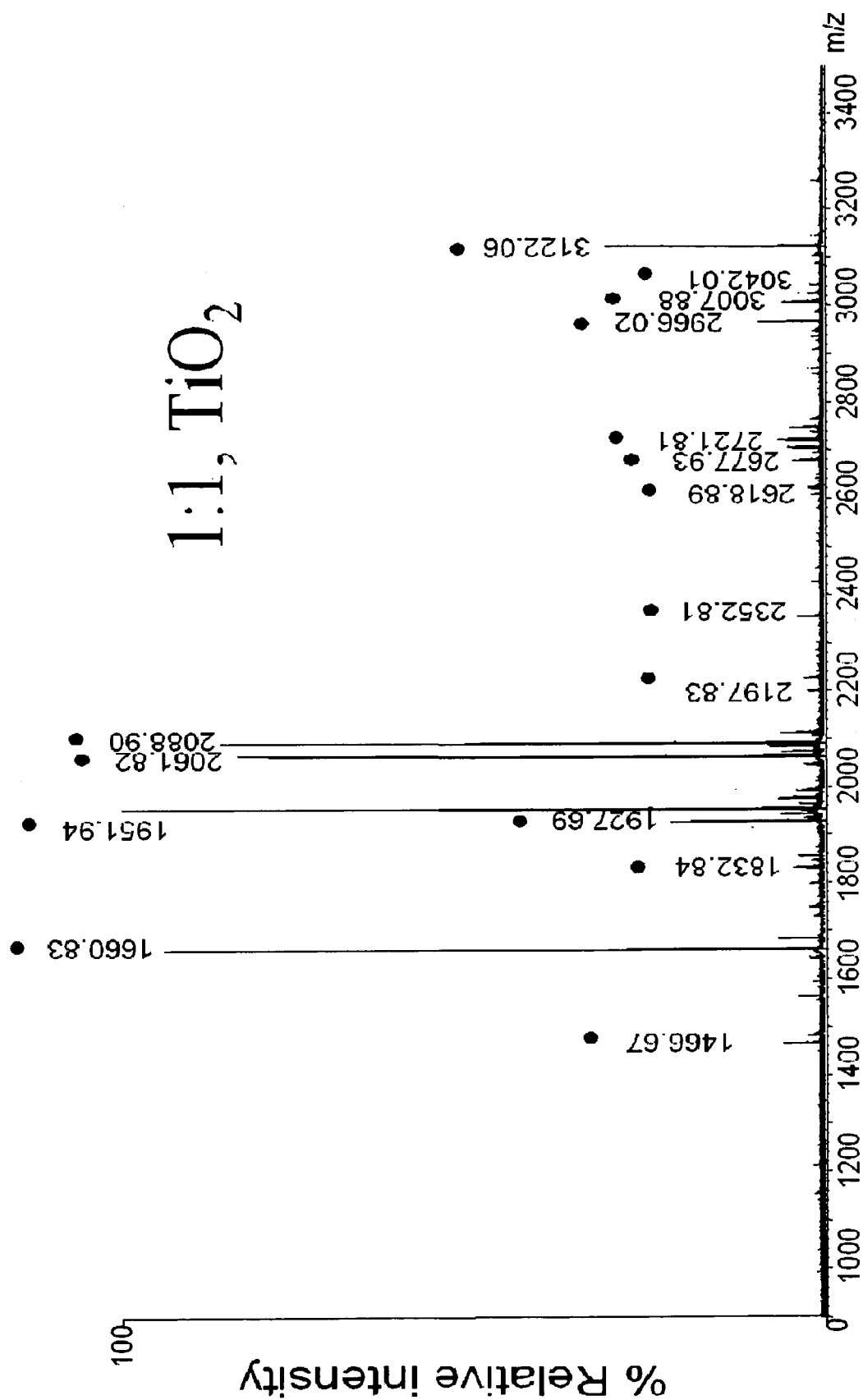
FIG. 15A shows MALDI mass spectra of phosphorylated peptides from peptide mixture 2 in a 1:1 ratio enriched by $TiO_2$.
FIG. 15B shows MALDI mass spectra of phosphorylated peptides from peptide mixture 2 in a 1:10 ratio enriched by $TiO_2$.
FIG. 15C shows MALDI mass spectra of phosphorylated peptides from peptide mixture 2 in a 1:50 ratio enriched by $TiO_2$.
FIG. 15D shows MALDI mass spectra of phosphorylated peptides from peptide mixture 2 in a 1:1 ratio enriched by IMAC beads (PHOSselect™).
FIG. 15E shows MALDI mass spectra of phosphorylated peptides from peptide mixture 2 in a 1:10 ratio enriched by IMAC beads (PHOSselect™).
FIG. 15F shows MALDI mass spectra of phosphorylated peptides from peptide mixture 2 in a 1:50 ratio enriched by IMAC beads (PHOSselect™).
Figure 15:
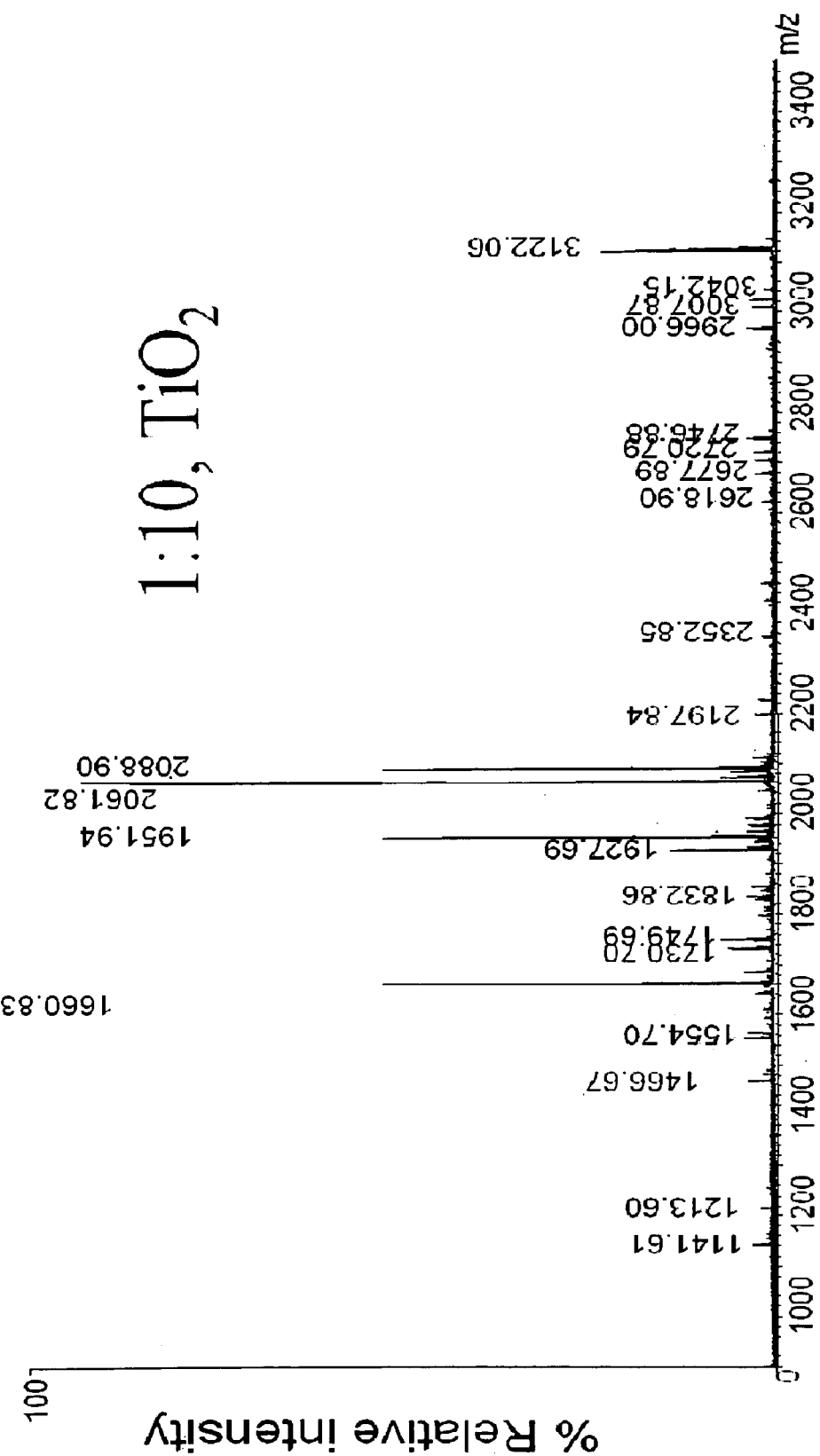
Figure 15:
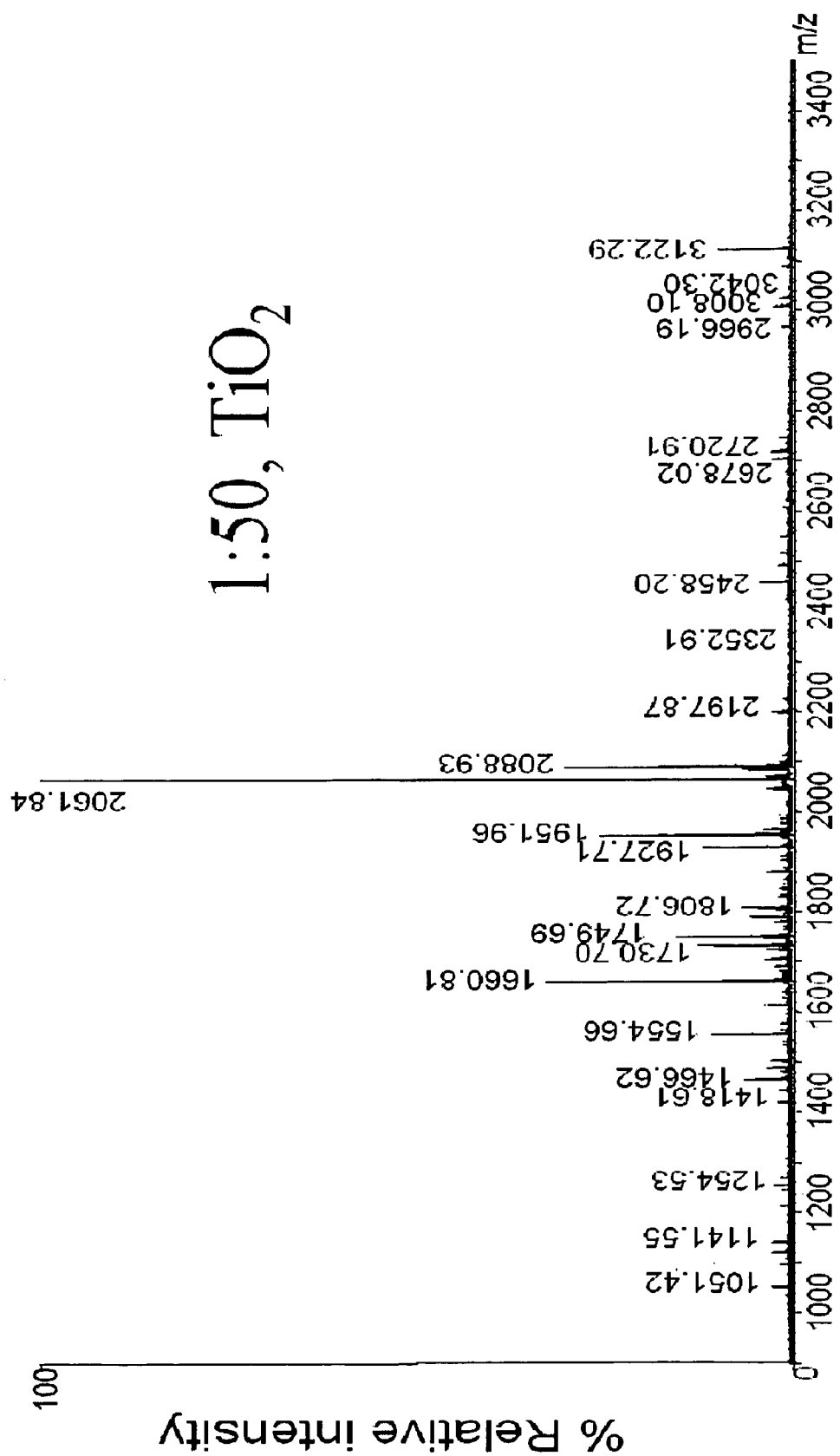
Figure 15:
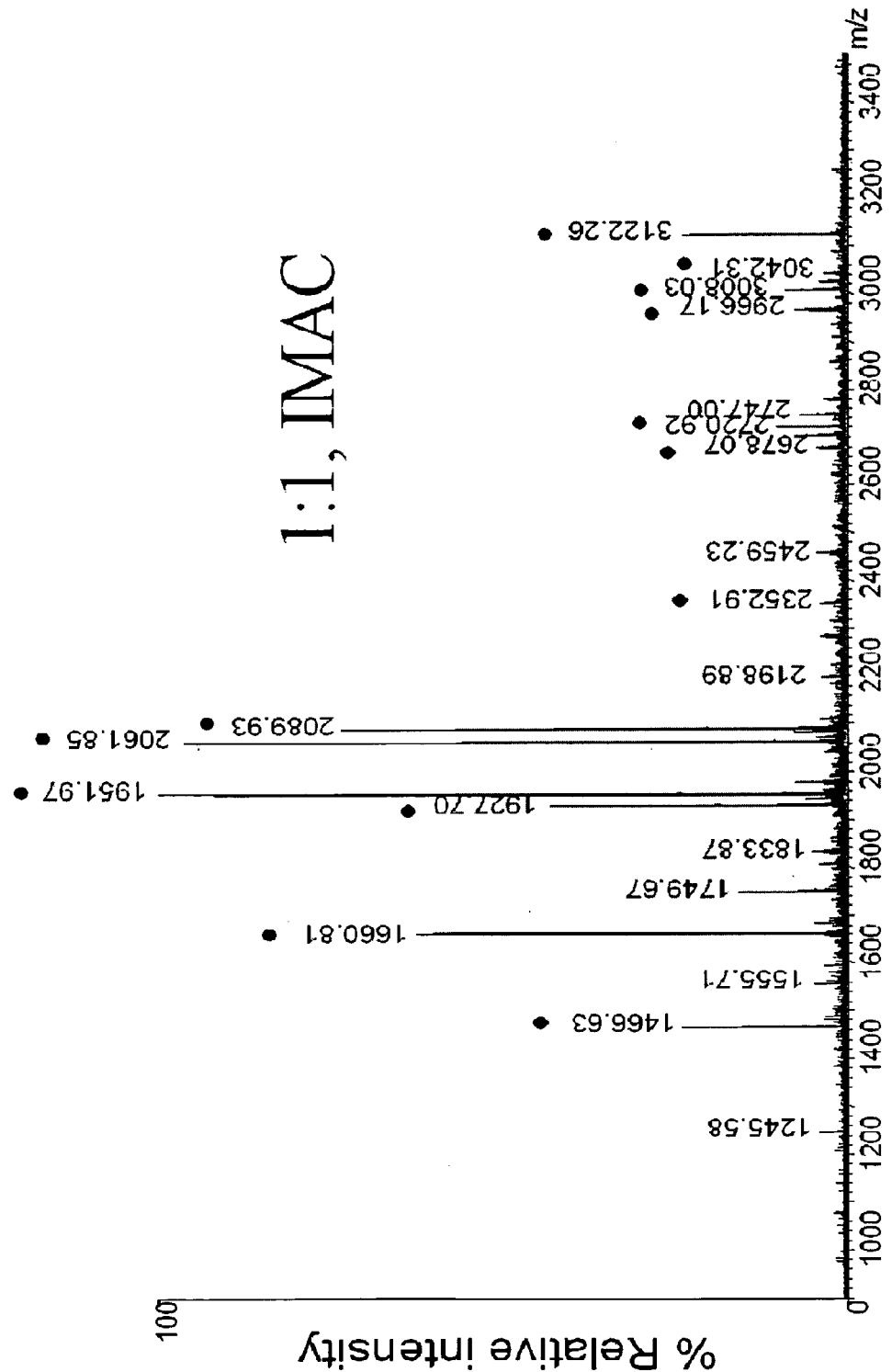
Figure 15:
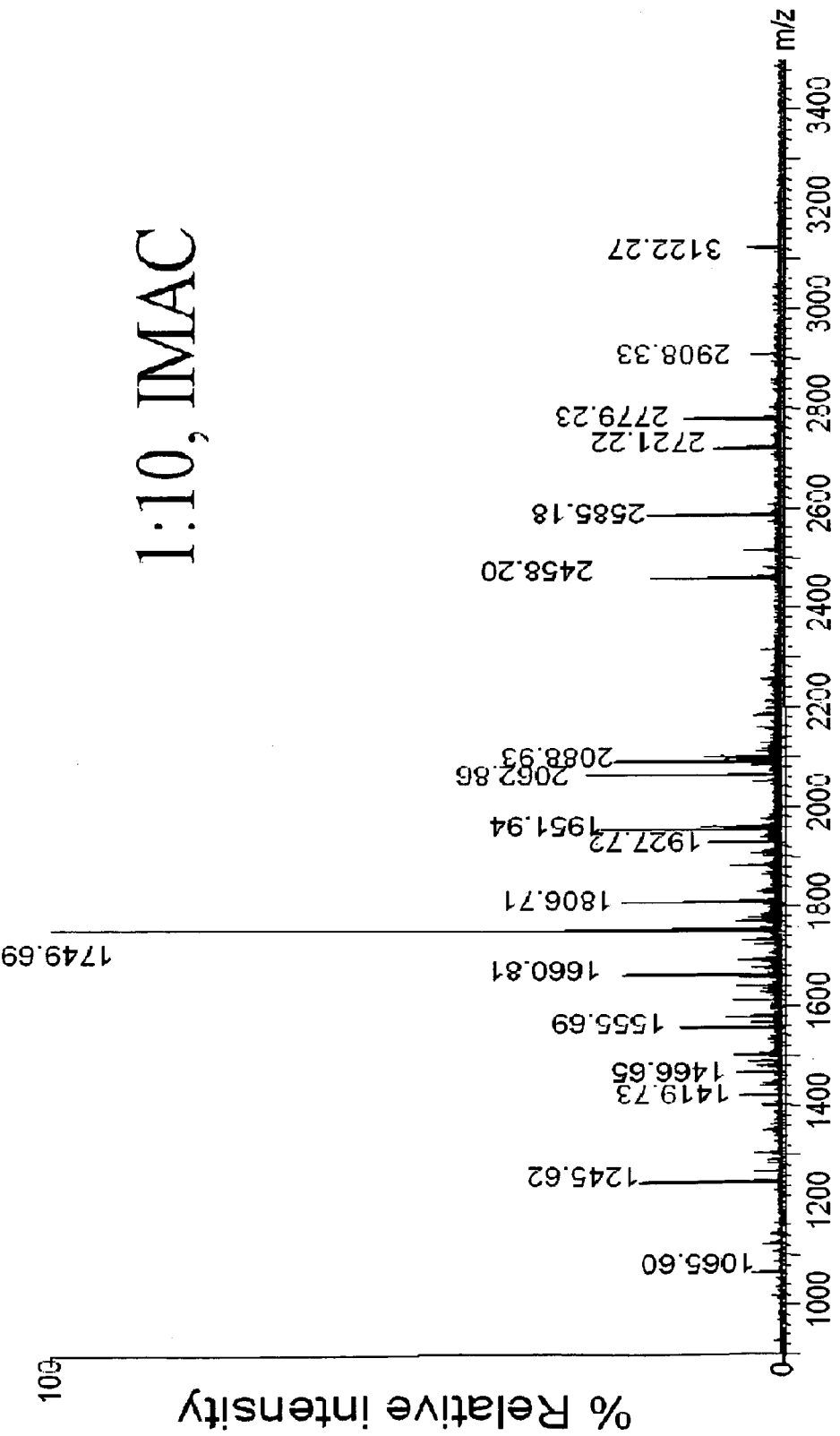
Figure 15:
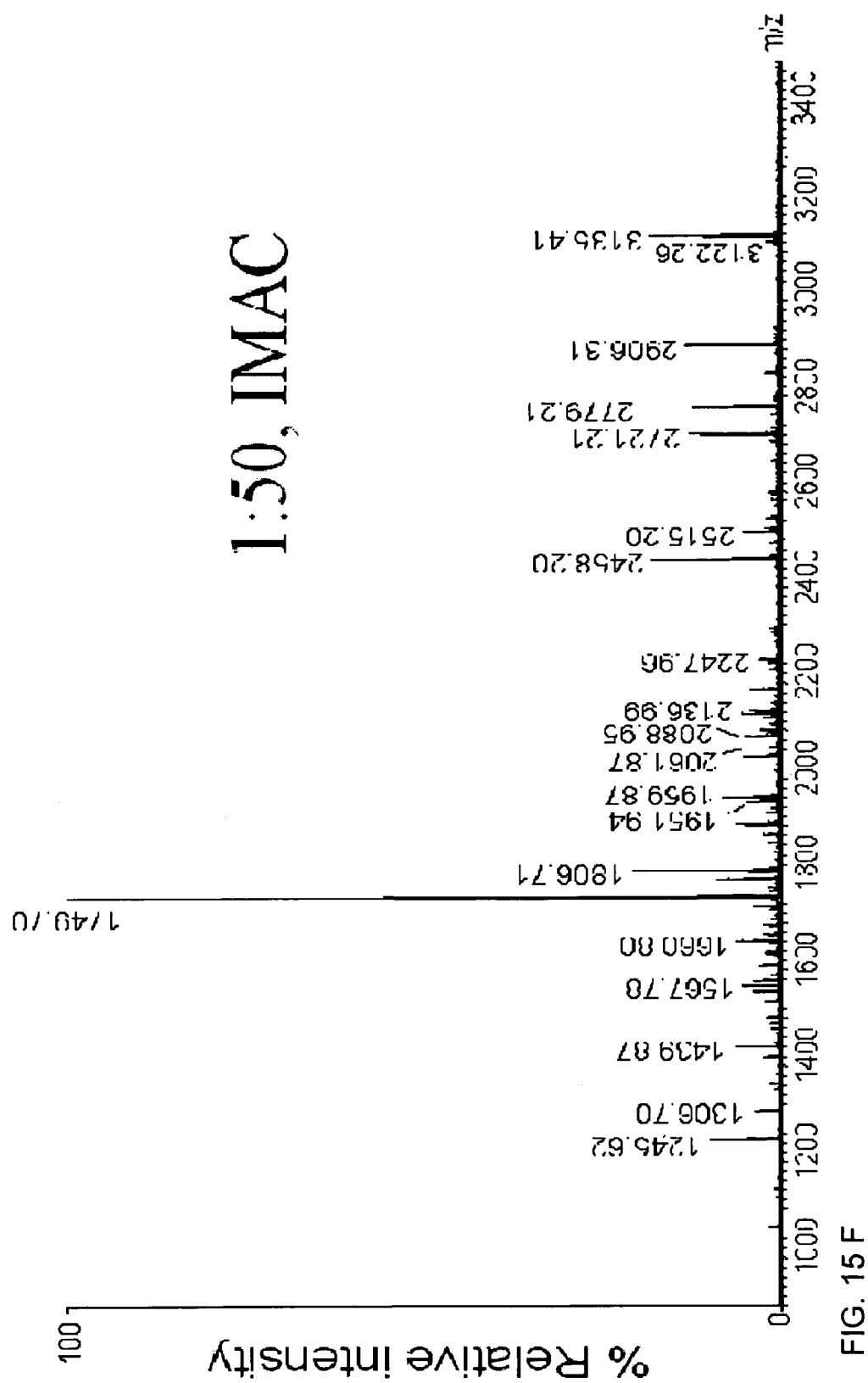

The selective enrichment of phosphorylated peptides using TiO$_2$ micro-columns was compared with IMAC. Peptides from peptide mixture 2 (ratio 1:1, 1:10 and 1:50) were purified using TiO$_2$ micro-columns and IMAC beads (PHOS-select™ (Sigma)), respectively. The resins were in both cases eluted with NH$_4$OH, pH 10.5 and the eluted peptides further purified using Poros Oligo R3 microcolumns and eluted from this column directly onto the MALDI MS target using 0.7 μL of the DHB/PA matrix solution. Elution with DHB from IMAC beads has been shown to improve the recovery of phosphorylated peptides. However, in this study NH$_4$OH, pH 10.5 was used in order to directly compare the binding selectivity of phosphorylated between TiO$_2$ and IMAC. In addition, elution with DHB matrix solution limits the possibility for down-stream applications like liquid chromatography coupled to MS. The resulting MALDI peptide mass maps obtained from the TiO$_2$ purifications are shown in FIG. 15 A-C and the MALDI peptide mass maps obtained from the IMAC purifications are shown in FIG. 15 D-F. The signals corresponding to the detected phosphorylated peptides are indicated by dots in FIGS. 15 A and 15 D. With the peptide mixture 2 (1:1 ratio) the two purification methods perform almost equally well with respect to number of detected phosphorylated peptides. However, a significantly higher number of non-phosphorylated peptides are observed in the IMAC experiment. With increasing ratio (1:10 and 1:50) the performance of the TiO$_2$ method significantly surpass the IMAC method with respect to number of detected phosphorylated peptides and reduction of the number of non-phosphorylated peptides present in the eluate (e.g., FIGS. 15 C and F). This indicates a much more selective binding of the phosphorylated peptides on the TiO$_2$ microcolumn than on the IMAC resin.

An aliquot of the peptide mixture 2 (ratio 1:1) (500 fmol) was loaded onto a TiO$_2$ microcolumn in DHB solution (350 mg/mL in 80% Acetonitrile/0.1% TFA) and the bound phosphorylated peptides were eluted by NH$_4$OH, pH 10.5. This peptide solution was diluted with 0.5% acetic acid and analyzed by LC-ESI-MSMS. The resulting fragment ion spectra were searched by the Mascot database search program and a total of 8 phosphorylated peptides were identified (the identified phosphorylated peptides according to Table 1: α-S1 casein: m/z 1660.8, 1951.9, 2693.9 (2678+oxidation); α-S2 casein: m/z 1331.5, 1411.5, 1466.6; β casein: m/z 2061.8; ovalbumin: m/z 2088.9). In addition to the phosphorylated peptides, 5 non-phosphorylated peptides were identified. Compared to the results obtained with MALDI MS (see e.g., FIG. 13 D), where more than 16 phosphorylated peptides were observed, the LC-ESI-MSMS is clearly showing a bias towards mono-phosphorylated peptides, as several multiphosphorylated peptides are not detected by the LC-ESI-MSMS analysis. Their absence in the LC-ESI-MSMS analysis was manually validated. A similar effect has been observed in a number of ongoing studies in our group employing both MALDI tandem MS and LC-ESI-MSMS (unpublished results). The reason for this bias is presently not known.

Figure 16:
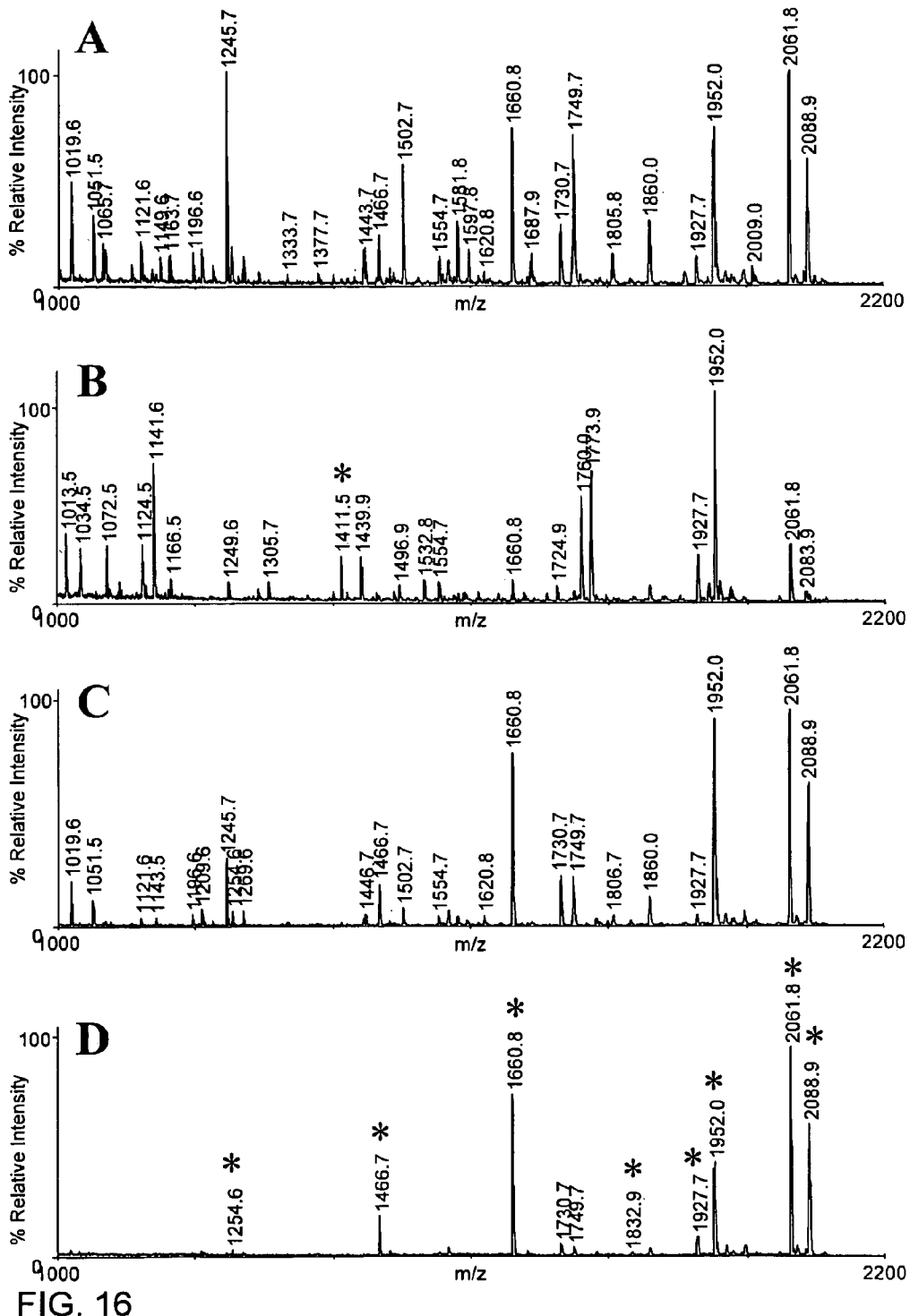
FIG. 16A shows MALDI mass spectra of peptide mixture 2 (ratio 1:1) obtained from $TiO_2$ enrichment using a loading buffer of 0.1% TFA.
FIG. 16B shows MALDI mass spectra of peptide mixture 2 (ratio 1:1) obtained from $TiO_2$ enrichment using a loading buffer of 0.13 M phosphoric acid.
FIG. 16C shows MALDI mass spectra of peptide mixture 2 (ratio 1:1) obtained from $TiO_2$ enrichment using a loading buffer of 0.13 M benzoic acid.
FIG. 16D shows MALDI mass spectra of peptide mixture 2 (ratio 1:1) obtained from TiO$_2$ enrichment using a loading buffer of 0.13 M DHB.

11. Use of Other Substituted Aromatic Carboxylic Acids in the Loading Buffer As shown, the presence of DHB in the loading buffer dramatically enhances the selective retainment of phosphorylated peptides on TiO$_2$. One possible explanation might be a competition for binding sites on TiO$_2$ between non-phosphorylated peptides and DHB molecules. We also tested a number of benzoic acid derivatives and other acids and determined their effect on the selective adsorption of phosphorylated peptides from complex peptide mixtures. Peptides from peptide mixture 2 (ratio 1:1) were applied onto TiO$_2$ microcolumns in 50% acetonitrile containing one of the following acids; trifluoroacetic acid; acetic acid; phosphoric acid; benzoic acid; salicylic acid; cyclohexane-carboxylic acid; phthalic acid; DHB. The bound peptides were eluted using NH$_4$OH, pH 10.5 and desalted and concentrated on Poros Oligo R3 microcolumns prior to MALDI MS analysis. The phosphorylated peptide binding selectivity was evaluated by comparing the relative abundances of these peptides with those of non-phosphorylated peptides. FIG. 16 shows MALDI mass spectra obtained from TiO₂ enrichment of phosphorylated peptides using four different acids in the loading buffer (TFA, phosphoric acid, benzoic acid and DHB). The spectra clearly show that DHB is the most efficient acid to prevent adsorption of nonphosphorylated peptides, while retaining the ability of TiO₂ to bind phosphorylated peptides. In contrast, phosphoric acid is not as effective as DHB to reduce binding of nonphosphorylated peptides and it appears to inhibit the adsorption of some of the phosphorylated peptides. For example, the relative abundances of the phosphorylated peptides at m/z 2088.9, m/z 1660.8 and 1466.7 are dramatically reduced when the loading buffer contains phosphoric acid, while the relative abundances of these peptides are rather similar in case of the other acids. Using salicylic acid or phthalic acid in the loading buffer yielded spectra very similar to those obtained from DHB, while cyclohexane carboxylic acid gave results very close to that of benzoic acid. The efficacy in inhibiting adsorption of nonphosphorylated peptides follows the order DHB~salicylic acid~phthalic acid>benzoic acid~cyclohexane carboxylic acid>phosphoric acid>TFA>acetic acid. Thus, the substituted aromatic carboxylic acids (i.e., DHB, salicylic acid and phthalic acid) are markedly better competitors than the monofunctional carboxylic acid (i.e., TFA, acetic acid, cyclohexane carboxylic acid and benzoic acid) for preventing binding of nonphosphorylated peptides to TiO₂. In line with this observation, infrared spectroscopic studies have shown that substituted aromatic carboxylic acids (including salicylic acid and phthalic acid) coordinate strongly to the surface of TiO₂, whereas monofunctional carboxylic acids (including benzoic acid and acetic acid) only interacts very weakly with TiO₂ (49). Interestingly, phosphate binds to TiO₂ with similar affinity ($K_A=4\times10^4$ $M^{-1}$) as substituted aromatic carboxylic acids ($K_A=10^4-10^5$ $M^{-1}$) (50) but it appears to be significant less effective in preventing binding of nonphosphorylated peptides. In this context, it is important to note that the binding mode of phosphate to TiO₂ differs from that of substituted aromatic carboxylic acids. For example, the binding mode of salicylic acid to TiO₂ is a chelating bidentate salicylate species (49,51), whereas the adsorption of phosphate anions to the surface of TiO₂ is a bridging bidentate surface complex (50) (see FIG. 17). The coordination geometry for an optimal phosphate binding site on TiO₂ is thus likely to differ from that of an optimal binding site for a substituted carboxylic acid. In this picture, phosphate will compete directly with phosphorylated peptides for binding sites on TiO₂, whereas DHB targets other binding sites which appear to be similar to those preferred by nonphosphorylated peptides. Such nonequivalent binding sites on TiO₂ may result from a structural heterogeneity of the TiO₂ surface, but the adsorbate itself is also likely to generate nonequivalent binding sites on TiO₂ by the ability of TiO₂ to transmit inductive electronic effects over a few rows of atoms (52). These results are consistent with an effect of DHB or other substituted aromatic carboxylic acids or non-aromatic, short chain, hydroxylated carboxylic acids to act as a competitive inhibitor of non-phosphorylated peptide binding. However, other mechanisms of the reported selective enrichment might also be relevant.

12. Derivatisation of Phosphopeptides while Immobilised on Stationary Phase

Figure 18:
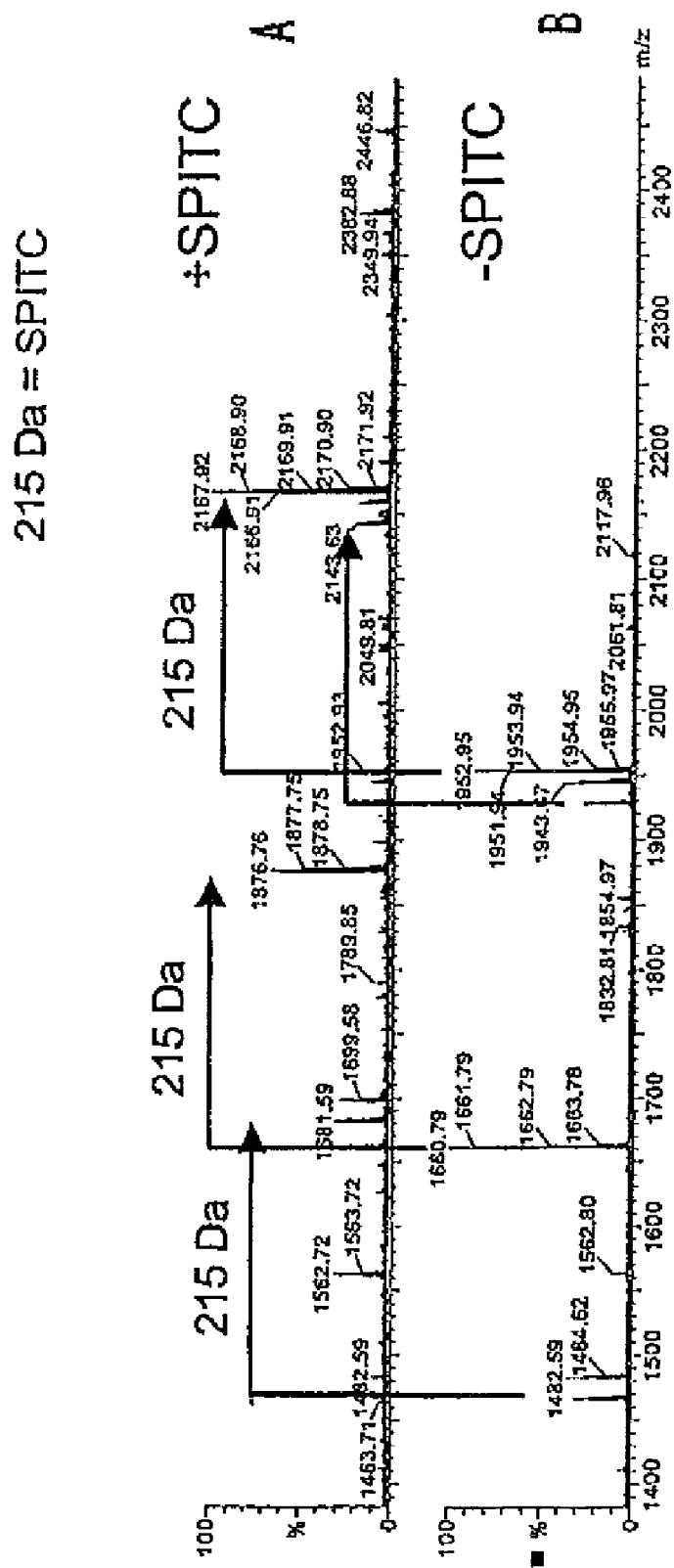
FIG. 18A shows purification of phosphopeptides using TiO$_2$ and immobilized on a stationary phase using the reagent SPITC.
FIG. 18B shows purification of phosphopeptides using TiO$_2$ and immobilized on a stationary phase without reagent SPITC.

Phosphopeptides derived from an enzymatic digest of alpha casein were loaded onto stationary phase as described herein and derivatized, while loaded onto stationary phase, using the reagent SPITC (4-sulfophenyl isothiocyanate). As shown in FIG. 18, the peptides can be derivatized while loaded onto stationary phase.

Peptides loaded onto stationary phase as described herein can be derivatized, while loaded onto stationary phase, using any reagent well known in the art, including but not limited to SPITC, PITC, FITC and CAF.

13. Identification Of Seven Previously Unknown Phosphorylation Sites in Stromal Proteins from *Spinacia oleracea*

The selectivity and practicality of using TiO2 micro-columns with a substituted aromatic carboxylic acid loading buffer for selective purification of phosphopetides allowed the successful analysis of stroma membranes purified by digitonin from illuminated spinach leaves. Novel phosphorylation sites were found in the light-harvesting apparatus of photosystem II (Lhcb1 proteins), in the PSII reaction center protein CP43, and in the cytochrome $b_6f$ Rieske FeS protein. Interestingly, more than one phosphorylation site was revealed on the same protein, and in some cases at different domains. Precise identification of new phosphorylation sites could bring significant biological insights about the cellular mechanisms of signalling activation and inhibition, in particular the existence of different kinases and/or different pathways.

Chemicals and Materials

Magnesium chloride, sodium chloride, sucrose, sodium fluoride, Na-EDTA, hepes, digitonin, phosphoric acid, trifluoroacetic acid, as well as analytical-grade acetonitrile were obtained from Sigma-Aldrich (Milan, Italy). Modified trypsin was purchased from Promega (Madison, Wis., USA), chymotrypsin from La Roche (Basel, Switzerland). GELoader tips were from Eppendorff (Eppendorf, Hamburg, Germany). 2,5-Dihydroxybenzoic acid (DHB) was from Fluka (St. Louis, Mo.). 3M Empore C8 disk was from 3M Bioanalytical Technologies (St. Paul, Minn., USA). Syringe for HPLC loading (P/N 038030, N25/500-7C PKT 2) were from SGE (Victoria, Australia). The water was from a Milli-Q system (Millipore, Bedford, Mass.). Titanium dioxide beads were obtained from a disassembled TiO₂ cartridge (4.0 mm ID—5020-08520-5u-TiO₂) purchased from GL sciences Inc, Japan. All other chemicals and reagents were of the highest grade commercially available.

Light Treatments of the Leaf Discs

Spinach (Spinacia oleracea) leaf discs (diameter 2.7 cm), punched from dark-adapted, fully expanded leaves and floating on distilled water in a Petri dish, were illuminated in a growth chamber under a photon flux densities (PFDs) of 100 $\mu mol$ $m^{-2}$ $s^{-1}$ for 1 hour at 23° C. A metal-halide lamp HQI-T 250W daylight served as a light source. For analysis of thylakoid phosphoproteins, the leaf discs were rapidly frozen in liquid nitrogen and stored at −80° C. until isolation of thylakoid membranes.

Isolation of Thylakoids and Preparation of Stroma Lamellae Membranes

Thylakoid membranes were isolated according to the method of Aro et al. (53) Frozen leaf discs were mixed with ice-cold isolation buffer containing 50 mM HEPES-NaOH, pH 7.5, 300 mM sucrose, 5 mM MgCl₂, 1 mM Na-EDTA, 10 mM NaF, and 1% (w/v) bovine serum albumin and thereafter rapidly homogenized. The homogenates were filtered through Miracloth and centrifuged at 1500×g for 4 min. The pellets were washed with 10 mM HEPES-NaOH, pH 7.5, 5 mM sucrose, 5 mM MgCl₂, and 10 mM NaF and pelleted at 3000×g for 3 min. Thylakoid pellets were resuspended to a concentration of 200 μg of chlorophyll/ml in 10 mM HEPES-NaOH, pH 7.5, 100 mM sucrose, 5 mM NaCl, 10 $MgCl_2$ and 10 mM NaF. Subfractionation of thylakoid membranes into grana and stroma lamellae with digitonin method were performed as described earlier (54). Recrystallized digitonin (1% in distilled water) was added to the stirred membranes to give a final concentration of 0.4%. The 2-min detergent treatment was terminated by a 10-fold dilution of the sample with resuspension buffer at 4° C. Differential centrifugation according to Anderson and Boardman (55) yielded pellets following 1000×g for 10 min, 10 000×g for 30 min, 40 000×g for 30 min, and 140 000×g for 60 min.

The preparations were protected from light and kept ice-cold during the isolation procedure.

Chlorophyll Determinations

The chlorophyll content of the isolated membranes was determined according to the method of Porra et al.(56)

In-Solution Protein Digestion

Preparation of the Surface-Exposed Peptides from Stroma Lamellae was Performed according to Vener et al. (57) with minor modifications as follows: isolated stroma membranes were washed twice with 25 mM $NH_4HCO_3$ (pH 8.0) by centrifugation and resuspended in the same buffer to a concentration of 1.8-2.0 mg of chlorophyll/ml. The suspension was incubated with sequencing-grade modified trypsin (Promega, Madison, Wis., USA) or chymotrypsin (La Roche, Basel, Switzerland) (8 μg of enzyme/mg of chlorophyll) at 22-23° C. for 2 hours. Note that the proteolytic treatment was not performed at 37° C. because a number of PSII phosphoproteins are rapidly dephosphorylated by the heat-shock-activated membrane protein phosphatase. The digestion products were acidified with 5% formic acid (FA), frozen, thawed, and clarified at 14 000 g for 10 min. The supernatant containing released peptides was collected for further analysis.

Purification of Phosphorylated Peptides Using $TiO_2$ Microcolumns $TiO_2$ microcolumns with a length of approximately 3 mm were packed in GELoader Tips. A small plug of C8 material was stamped out of a 3M Empore™ C8 extraction disk using a HPLC syringe needle and placed at the constricted end of the GELoader tip. The C8 disk serves only as a frit to retain the titanium dioxide beads within the GELoader tip. The $TiO_2$ beads were suspended in 80% acetonitrile/0.1% TFA and an aliquot of this suspension (depending on the size of the column) was loaded onto the GELoader tip. Gentle air pressure created by a plastic syringe was used to pack the column. The peptide solution (5-10 μL) was loaded onto $TiO_2$ columns in DHB solutions (200 mg/mL in 80% acetonitrile/0.1% TFA). The columns were washed with 10 μL of the DHB solution and 20 μL of 80% acetonitrile/0.1% TFA. The bound peptides were eluted using 3 μL $NH_4OH$, pH 10.5 and the eluate was analysed directly by LC- or MALDI-MS/MS after acidification.

Nano-Flow Liquid Chromatography Electrospray Tandem Mass Spectrometry Analysis (LC-ESI-MS/MS)

Automated nanoflow liquid chromatography/tandem mass spectrometric analysis was performed using a QTOF Ultima mass spectrometer (Micromass UK Ltd., Manchester, UK) employing automated data dependent acquisition (DDA). A nanoflow-HPLC system (Ultimate; Switchos2; Famos; LC Packings, Amsterdam, The Netherlands) was used to deliver a flow rate of 2 μl/min (loading) and 100 nl/min (elution). Loading was accomplished by using a flow rate of 2 μl/min onto a homemade 2 cm fused silica precolumn (75 μm i.d.; 375 μm o.d.; Resprosil C18-AQ, 3 μm (Ammerbuch-Entringen, DE) using autosampler. Sequential elution of peptides was accomplished using a linear gradient from Solution A (0.6% acetic acid) to 40% of Solution B (80% acetonitrile; 0.5% acetic acid) in 40 minutes over the precolumn in-line with a homemade 10-15 cm resolving column (50 μm i.d.; 375 μm o.d.; Resprosil C18-AQ, 3 μm (Ammerbuch-Entringen, Germany). The resolving column was connected using a fused silica transfer line (20 μm I.D.) to a distally coated fused silica emitter (New Objective, Cambridge, Mass., USA) (360 μm OD/20 μm ID/10 μm tip ID) biased to 1.8 kV.

The mass spectrometer was operated in the positive ion mode and data dependent analysis was employed (three most abundant ions in each cycle): 1 second MS (m/z 350-1500) and 3×2 second MSMS (m/z 50-2000, continuum mode), 30 seconds dynamic exclusion. External mass calibration using NaI resulted in mass errors of less than 50 ppm, typically 5-15 ppm in the m/z range 50-2000. Raw data were processed using Protein Lynx Global Server Protein Lynx (smooth 3/2 Savitzky Golay and center 4 channels/80% centroid) and the resulting MS/MS data set exported in the Micromass pkl format. Automated peptide identification from raw data was performed using an in-house MASCOT server (v. 2.0) (Matrix Sciences, London, UK) using the NCBI non-redundant protein database using the following constraints: only tryptic peptides up to two missed cleavage sites were allowed; 20 ppm tolerance for MS and ±0.2 Da for MS/MS fragment ions; carbamidomethyl cysteine (C) was specified as a fixed modification, deamidation (NQ) phosphorylation (S, and T and Y) and methionine oxidation (M) were specified as variable modifications.

Matrix-Assisted Laser Desorption/Ionization Time-of-Flight Mass Spectrometry (MALDI-TOF MS)

MALDI-MS was performed using a MALDI quadrupole time-of-flight (Q-TOF) mass spectrometer (Micromass, Manchester, UK). All spectra were obtained in positive reflector mode.

Mass spectrometric data analysis was performed using the software MassLynx 3.5. Sequence analysis and peptide assignment were accomplished using the GPMAW software (http://welcome.to/gpmaw). For analysis of phosphorylated peptides, DHB (20 mg/ml) in 50% acetonitrile, 1% phosphoric acid was used as the matrix. Note that inclusion of 1% phosphoric acid in the MALDI matrix solution increases the relative abundance of multiphosphorylated peptides.

Within each chloroplast, the thylakoids form a continuous network which contains two distinct types of membrane domains, the stacked grana thylakoids and the unstacked stroma thylakoids. Photosystem I (PSI) is predominantly localized in stroma lamellae and peripheral membranes of the grana, while photosystem II (PSII) is mainly located in grana appressions. It is well documented that under illumination, the light harvesting proteins of PSII undergo phosphorylation and migrate to PSI. Reversible phosphorylation also controls the photoinhibition-repair cycle of the PSII reaction centre subunits, in particular migration of the damaged PSII to stroma-exposed thylakoids can be regarded as the first step in the PSII repair cycle. With the aim to study the role of photosynthetic protein phosphorylation either regarding the mechanisms of light energy distribution balancing between the two photosystems or the turnover processes, thylakoids from illuminated spinach leaves were fractionated by digitonin and stroma membranes were investigated to identify phosphorylation sites by mass spectrometry. Illumination of spinach leaves was performed at 100 μmol $m^{-2}$ $s^{-1}$ for 1 hour, since it was previously demonstrated that under these experimental conditions maximum phosphorylation occurs. Knowing that protein phosphorylation in thylakoids is restricted to the outer surface-exposed regions of the membrane proteins allowed the "exposed" peptides to be released by the stroma samples being introduced to trypsin. The characterization of the thylakoid phosphopeptides by mass spectrometry has previously been performed by using IMAC enrichment with immobilized Fe(III) and Ga(III) cations.

Phosphorylated peptides were enriched from stroma membranes by using the methods described herein and analysed by both MALDI and nano LC ESI Q-TOF tandem MS. For phosphopeptide detection we utilized the preferred loss of the phosphate group upon collision-induced dissociation (CID). In positive ion tandem MS, an intense neutral loss of 98 Da corresponding to $H_3PO_4$ is observed for serine and threonine phosphorylated peptides.

Preliminary experiments of the phosphorylation status of these photosynthetic proteins showed the presence of CP43 (1+, 1385.65 m/z), D1 (1+, 980.47 m/z), D2 (1+, 710.32 m/z) and Lhcb1.3 (1+, 1501.59 m/z) phosphorylated forms in dark-adapted samples (data not shown). Interestingly, a higher number of phosphopetides were detected after leaf illumination. Table 1 lists the light-activated phosphopeptides identified in the stroma samples after $TiO_2$ enrichment and MS/MS analyses. However, besides the previously known phosphopeptides belonging to photosynthetic proteins, a number of new phosphopeptides were detected, which will be discussed separately below.

Figure 19:
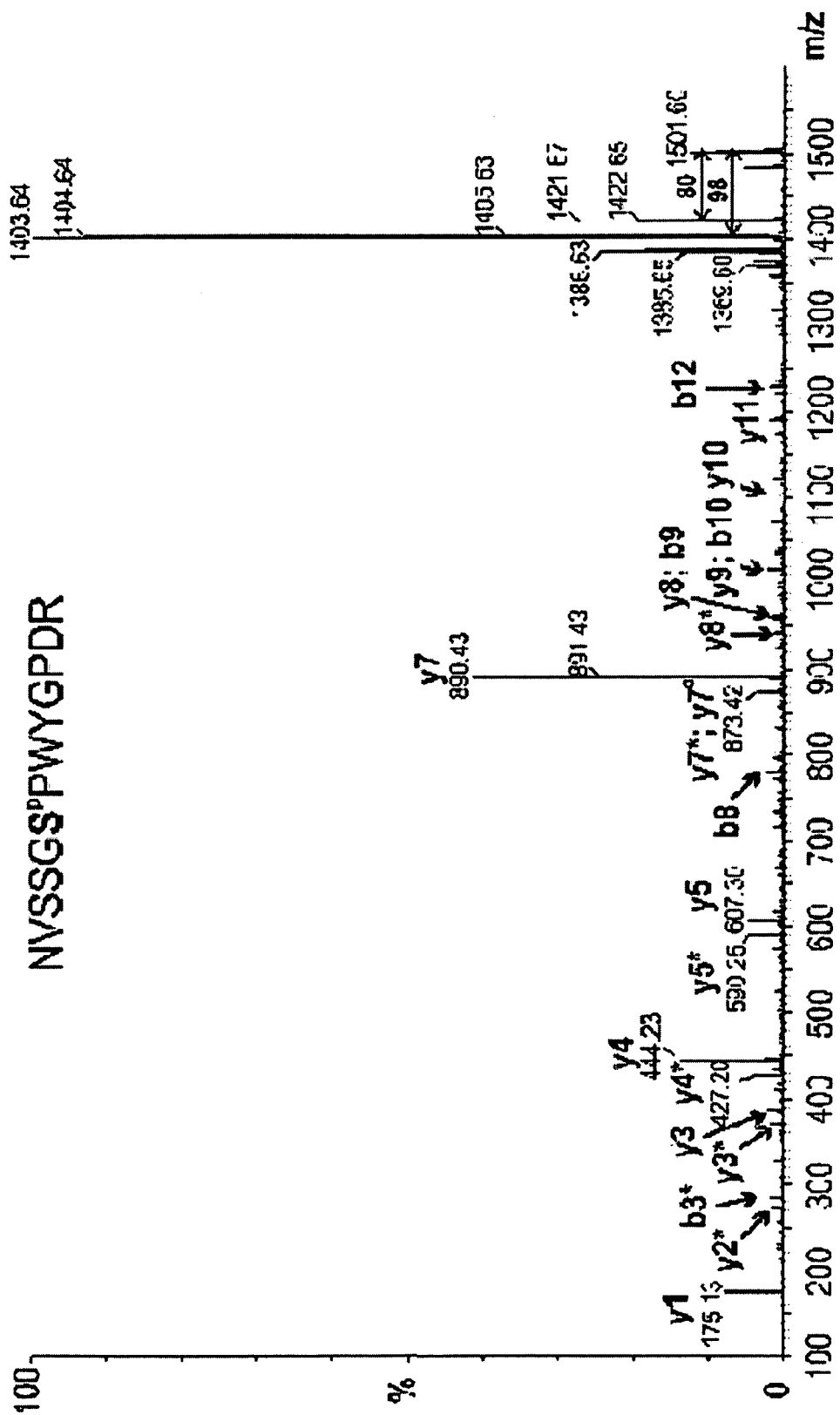
FIG. 19A shows MALDI-Q-TOF tandem MS spectrum of the NVSSGS$^P$PWYGPDR phosphopeptide in the Lhcb1 protein with parent molecular ion at 1501.60 m/z.
FIG. 19B shows MALDI-Q-TOF tandem MS spectrum of the NVSSGS$^P$PWYGPDR phosphopeptide in the Lhcb1 protein after nanoelectrospray ionization and CID.
Figure 19:
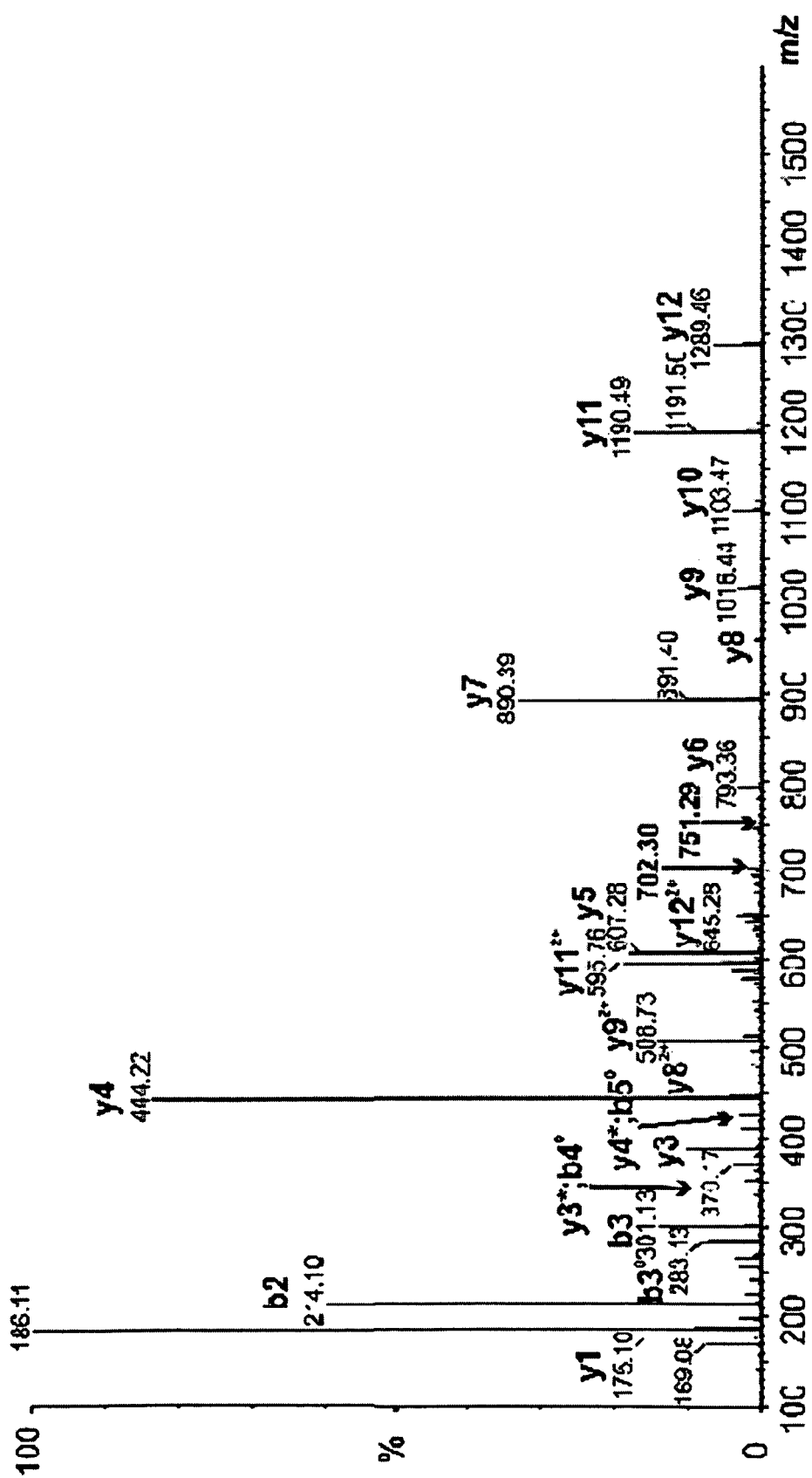

New phosphorylation sites in light harvesting protein Lhcb1—MALDI Q-TOF sequencing of the tryptic mono-charged peptide at 1501.59 m/z identified it as $NVSSGS^PP$-WYGPDR (SEQ ID NO. 2), where SP designates the phosphorylated aminoacid (FIG. 19A). Mascot sequence similarity searching found that this sequence belongs to the light harvesting chlorophyll a/b binding protein Lhcb1 from *Prunus persica* (NCBI accession number gi/556367). To verify this result, we analysed the mixture of peptides with nano LC ESI Q-TOF MS/MS. The electrospray tandem MS spectrum for the same peptide belonging to Lhcb1 (2+, 751.29 m/z) is shown in FIG. 19 B. Much more pronounced b and y ion series were obtained, e.g. the presence of the ion at m/z 301.22 evidently rules out the serine 4 as potential phosphorylation site, as well as the signal corresponding of the doubly charged y8 fragment ion ($y8^{++}$=480.22 m/z) confirming the assignment of the phosphorylation to serine 6. Automatic sequencing by LC ESI MS/MS also identified the sequence of the phosphopeptide $T^PVQSSSPWYGPDR$ (SEQ ID NO. 3) (doubly charged molecular ion with m/z 780.30), whose CID spectrum is displayed in FIG. 20. The peptide tandem mass spectra contained a highly abundant neutral loss peak (corresponding to the signal at m/z 731.35) indicative of phosphorylation. The presence of N-terminal b2-b6 ions with neutral loss of 98 Da (in particular b2=183.10 m/z; b3=311.17 m/z) localizes the phosphorylation site to the first threonine.

It is known that the Lhcb1 protein exists in spinach in three distinct isoforms that differ in their amino terminus called Lhcb1.1 (Ac-RK SAGKPK NVSSGSPWYGPDR) (SEQ ID NO. 4), Lhcb1.2 (Ac-RK TAGKPK TVQSSSPWYGPDR) (SEQ ID NO. 5) and Lhcb1.3 (Ac-RK TAGKPK NVSSGSP-WYGPDR) (SEQ ID NO. 6). In earlier experiments the light-induced phosphorylation of light-harvesting proteins was localized to the threonine or serine 3. Interestingly, the newly identified phosphorylated peptide $T^PVQSSSPWYGPDR$ (SEQ ID NO. 7) belongs to Lhcb1.2 isomer, whereas the sequence $NVSSGS^PPWYGPDR$(SEQ ID NO. 8) can be ascribed either to Lhcb1.1 or to Lhcb1.3 isoforms. However, previous investigations performed by both intact mass measurements and immunoblotting rule out a phosphorylated form of the Lhcb1.1 protein.

New Phosphorylations Sites in CP43 Protein

Figure 21:
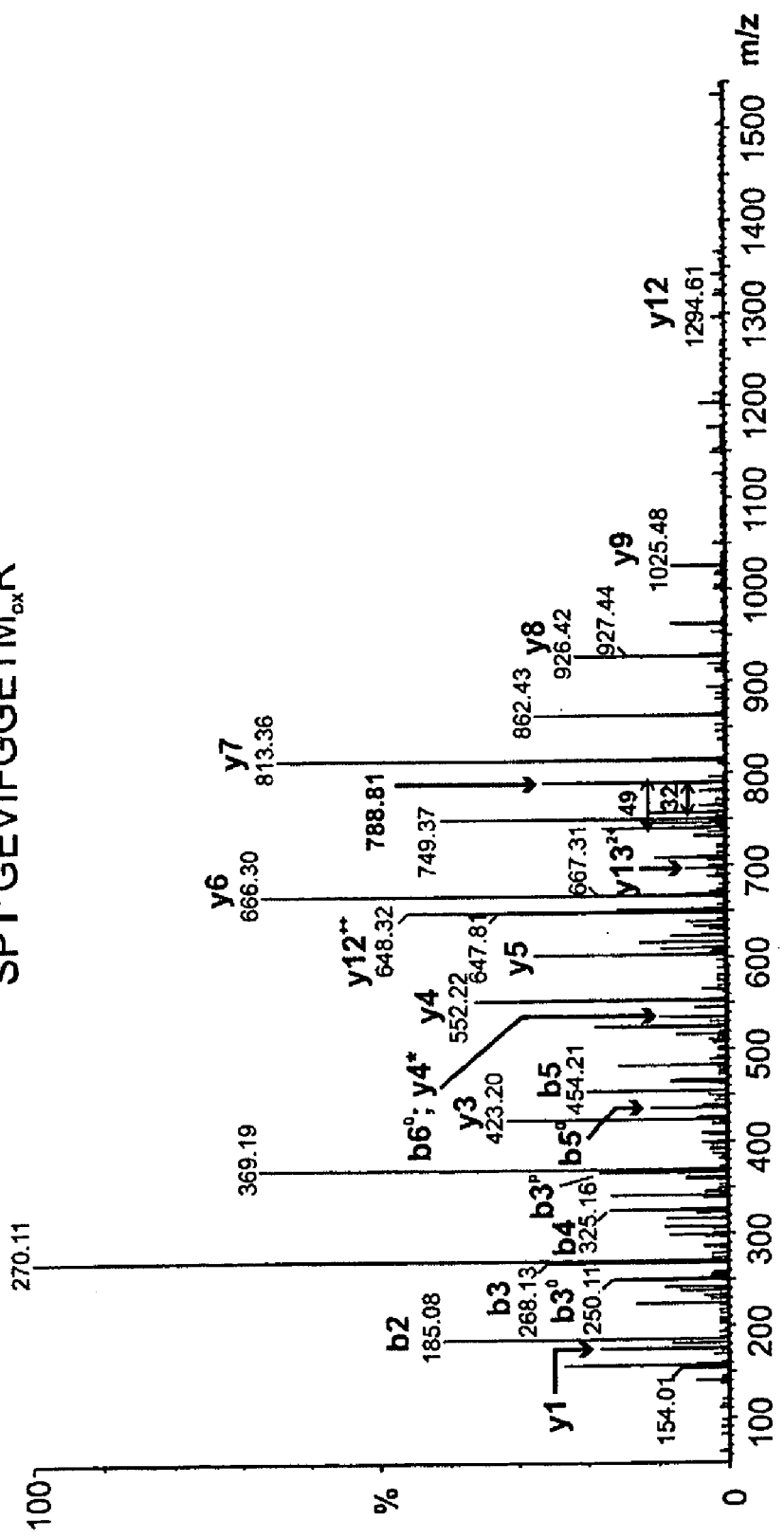
FIG. 21 shows identification of SPT$^P$GEVIFGGETM$_{ox}$R (SEQ ID NO. 9) phosphopeptide in the CP43 protein.

The most characterized thylakoid phosphoproteins have been shown to be phosphorylated at or close to the N-terminus generally exposed to the stromal side. Interestingly, our experimental data revealed for the first time a novel phosphorylation site in a lumen-exposed loop of CP43 protein close to its C-terminal. FIG. 21 shows the ESI tandem mass spectrum of the doubly charged ion at m/z 788.81 matching to the sequence $SPT^PGEVIFGGETM_{ox}R$ (SEQ ID NO. 9) in the CP43 protein. This peptide is located in position 344-357 of the CP43 amino acid sequence (NCBI accession number gi|7443192, *Spinacia oleracea*) and we found the presence of both a phosphorylation and an oxidation. In particular, neutral loss of $H_3PO_4$ from the doubly charged parent ion produced the signal at m/z of 739.84 indicating phosphorylation. The peptide contains two potential phosphorylation sites (serine 1 or threonine 3), but the presence of the b2 ion with m/z 185.08 clearly rules out serine 1 whereas the b3 (m/z 268.13) fragment ion perfectly corresponds to a phosphorylated threonine residue after the neutral loss of 98 Da.

Figure 22:
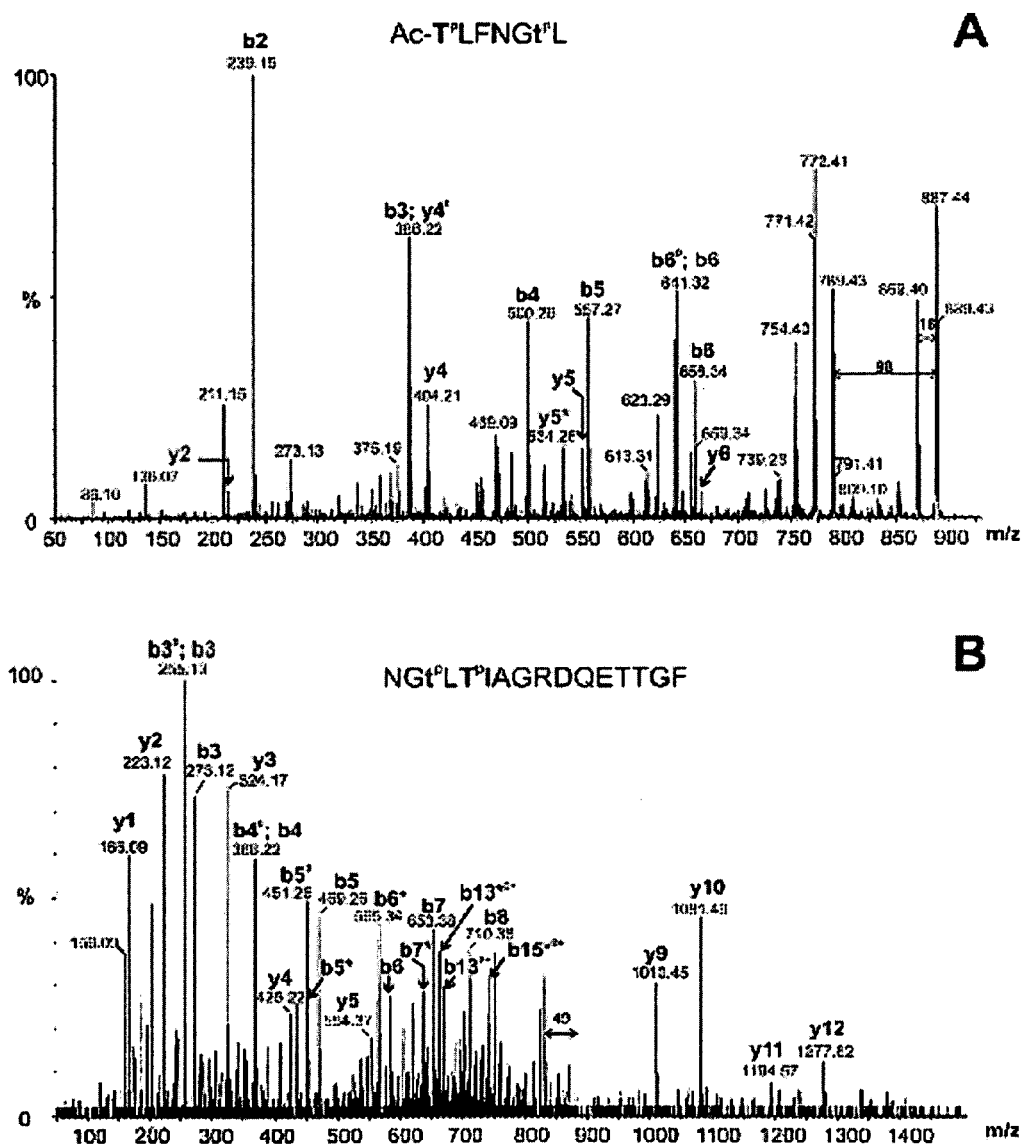
FIG. 22A shows MALDI-Q-TOF tandem MS spectrum of the chymotryptic phosphopeptide Ac-T$^P$LFNGt$^P$L.
FIG. 22B shows Tandem MS spectrum obtained after nanoelectrospray ionization and CID of the peptide NGt$^P$LT$^P$LAGRDQETTGF.

Concerning the well known N-terminal phosphorylation of CP43 protein, we isolated and sequenced the tryptic peptide at 1385.65 m/z (Ac-$T^PLFNGTLTLAGR$)(SEQ ID NO. 10). A careful analysis of the MS/MS spectrum obtained suggested there was a mixture of isomeric peptides. In addition to the presence of the well documented phosphorylation on threonine 1 there was the possibility of phosphorylations on threonines 6 and 8 indicated by some low abundant b and y ions (data not shown). To confirm this we performed an in-solution chymotryptic digestion and two different peptides were detected: Ac-$T^PLFNGt^PL$ (SEQ ID NO. 11) (887.38 m/z); $NGt^PLT^PLAGRDQETTGF$ (SEQ ID NO. 12) (880.93$^{2+}$ m/z) where $T^P$ indicates the main phosphorylation site, whereas the lowercase residue corresponds to a secondary phosphorylation site. The registered m/z values of 887.38 and 880.93 fit with the addition of only one phospho group, but in the ion MS/MS spectra we found the presence of b and y ion fragments at significant levels produced from CID of several isomeric phosphorylated peptides. FIG. 22 A shows the fragment ion spectrum of the chymotryptic mono-charged peptide at 887.38 m/z obtained on a MALDI Q-TOF. The elimination of phosphoric acid (98 Da) from the precursor ion gives rise to the intense signal at 789.43 m/z. The N-terminal acetylation was easily assigned based on the detection of a complete b series with addition of 42 Da. Concerning the phosphorylation, we can surmise that threonine 1 is the main phosphorylation site (clear signals produced after the 98 Da neutral loss at b2(239.15), b3(386.22), b4(500.26), b5(557.27), and b6(658.34) m/z) but several peaks suggest a second minor phosphorylation site on threonine 6 that could represent up to 20% of the total CP43 phosphorylated pool (based on ion signals). Firstly, the 215.14 m/z ion corresponds to the y2 fragment after the neutral loss from the threonine 6. Secondly, the prominent signal at 641.32 m/z could be assigned to an internal β-elimination reaction from the same residue. A confirmation of this behaviour was obtained by analyzing the fragmentation pattern of the second phosphorylated peptide with the calculated molecular mass of 1759.86 Da, the 16-amino acid-long sequence shown in FIG. 22 B. This amino acid stretch was identified as the chymotryptic peptide aa 8-23 of the CP43 protein and its sequence partially overlaps the one of the peptides examined above. The fragment ion spectrum shown in FIG. 22 B corresponds to the doubly protonated molecular ion of this peptide at 880.93 m/z and it is also present in the beta-eliminated form at 831.95 m/z. In this case the phosphorylation site is localizated to threonine 5, however the pronounced peaks at 255.13 and 368.22 m/z designate the threonine 3 as a secondary phosphorylated amino acid residue.

New Phosphorylations Sites in Rieske FeS Protein

Our MS/MS analyses identified the sequence of the previously unknown phosphopeptide $AT^Ps^PIPADNVPDM_{ox}QK$ (SEQ ID NO. 13) belonging to Rieske FeS protein from the cytochrome $b_6$/f-complex of spinach thylakoids. Both doubly (791.81 m/z) and triply (plus a C-terminal arginine, 580.24 m/z) charged forms of this peptide were subjected to CID and the results are displayed in FIGS. 23 A and 23 B, respectively. The series of N-terminal fragments with the neutral loss pattern localized the phosphorylation site to threonine 2 or serine 3. The presence of 242.11 and 224.10 m/z signals strongly suggested the serine as phosphorylation site representing the b3 loss of 98 and 18 Da respectively. However, closer examination of the spectrum in the region m/z 200-450 revealed the ion at 253.06 m/z corresponding to b2+80 Da and the ion at 225.10 m/z corresponding to a2+80 Da (the 225.10 m/z signal height should be significantly smaller if it was the isotopic peak for 224.10 m/z ion, see inset of FIG. 23 A). These ions, jointly with the signal at 155.03 m/z, suggested that the threonine is phosphorylated. On the other hand, it can be noted that also the peak at 340.10 m/z (b3+80 Da) was present providing further evidence to suggest phosphorylation at the serine. From these analyses, it can be suggested that there are two mono-phosphorylated versions of this peptide.

These specific examples should not be interpreted as a limitation to the scope of the invention. Instead, these are merely exemplary embodiments one skilled in the art will understand from the entire disclosure of this invention.

DETAILED DESCRIPTION OF THE FIGURES

FIG. 1: MALDI Mass Spectra of Fetuin and its Tryptic Fragments.

Fetuin, which contain 3 N-linked glycosylation sites, all of which have terminal sialic acid moities, was digested with trypsin. An aliquot of the tryptic peptide mixture was analyzed by MALDI MS (FIG. 1 A). Another aliquot of the tryptic peptide mixture was applied onto $TiO_2$ in DHB loading buffer and the column was washed. The peptides eluted off the $TiO_2$ column were analyzed by MALDI MS (FIG. 1 B). P denotes signals originating from phosphorylated peptides. The signals in the high mass area originate from sialic acid containing glycopeptides. An aliquot of the peptide solution was treated with alkaline phosphatase to remove the phosphate groups on phosphopeptides and subsequently loaded onto $TiO_2$ in DHB loading buffer. A small amount of the eluted peptides was analyzed by MALDI MS (FIG. 1 C). The high mass peptides originate from sialic acid containing glycopeptides. The remaining aliquot was treated with N-glycosidase F to remove N-linked glycan structures. The deglycosylated peptides were analyzed by MALDI MS (FIG. 1 D). The mass at m/z 1443.7 and 1743.0 originates from the peptide 145-159 of the fetuin sequence containing the N156 glycosylation site. The mass at m/z 3019.4 originates from the peptide 160-187 of the fetuin sequence containing the N176 glycosylation site. The mass at m/z 3675.1 originates from the peptide 72-103 of the fetuin sequence containing the N99 glycosylation site.

FIG. 2: MALDI Mass Spectra of $O^{16}$- and $O^{18}$-Labelled Sialylated and De-Sialylated Tryptic Fragments of Fetuin.

Tryptic peptides originating from Fetuin were treated with alkaline phosphatase, split into two tubes and lyophilized. The lyophilized peptides were re-digested using trypsin in normal buffer in one tube and in $O^{18}$ buffer in the other tube. This gives a mass difference between the two populations of peptides of 4 Da after mixing. The peptides in normal buffer were treated with neuramidase (to cleave off terminal sialic acid moities). The two populations of peptides were mixed in DHB loading buffer in a ratio 1:1 and purified on $TiO_2$. After elution, purified glycopeptides were treated with N-glycosidase F to remove glycan structures. Deglycosylated peptides were analyzed by MALDI MS as shown. The ratio between light and the heavy versions of the peptides provide a measure of specificity of $TiO_2$ towards purification of sialylated glycopeptides. The light peptides do not contain sialic acid whereas the heavy peptides are sialylated. The ratios indicate that $TiO_2$ is about 95% specific to sialylated compared to non-sialylated glycopeptides. The small signals from light peptides could be artifacts arising from: (1) Impurity of the $O^{18}$ buffer which may be only 95% pure (5% $O^{16}$ water) (2) Inefficiency of neuramidase digestion resulting in incomplete de-sialylation of the light peptides.

FIG. 3: MALDI Mass Spectra of Tryptic Fragments of Non-Sialylated RNAseB.

The binding of glycopeptides from RNAse B (which contains only high mannose structures without sialic acids) to $TiO_2$ was compared using an HILIC buffer and using loading buffer comprising a substituted aromatic carboxylic acid (DHB). (FIG. 3 A) Isolation of peptides from $TiO_2$ loaded with HILIC buffers which is known to retain glycopeptides. (FIG. 3 B) Isolation of peptides from $TiO_2$ loaded with loading buffer including DHB. No binding of non-sialylated peptides is observed when a substituted aromatic carboxylic acid is included in the loading buffer.

FIG. 4: MALDI Mass Spectra of Sialylated Tryptic Fragments of Fetuin Isolated Using Non-Aromatic, Short Chain, Hydroxylated Carboxylic Acids in the Loading Buffer.

Tryptic peptides originating from Fetuin were treated with alkaline phosphatase then loaded on $TiO_2$ stationary phase material in acidic loading buffer alone (FIG. 4 A) or in acidic loading buffer comprising 2.5% TFA and 80% acetonitrile and the following: (FIG. 4 B) no further additives (FIG. 4 C) saturated phthalic acid (FIG. 4 D) 1 M glycolic acid (FIG. 4 E) 1 M lactic acid (FIG. 4 F) 1 M citric acid (FIG. 4 G) 1 M oxalic acid. All of the peaks between 4000 and 10000 m/z in the figure as shown correspond to sialylated peptides. As shown, while considerable non-specific binding is apparent in the untreated and oxalic acid samples. Each of the other non-aromatic, short chain, hydroxylated carboxylic acids was effective as an additive to the loading buffer in improving enrichment of sialylated peptides.

Figure 5:
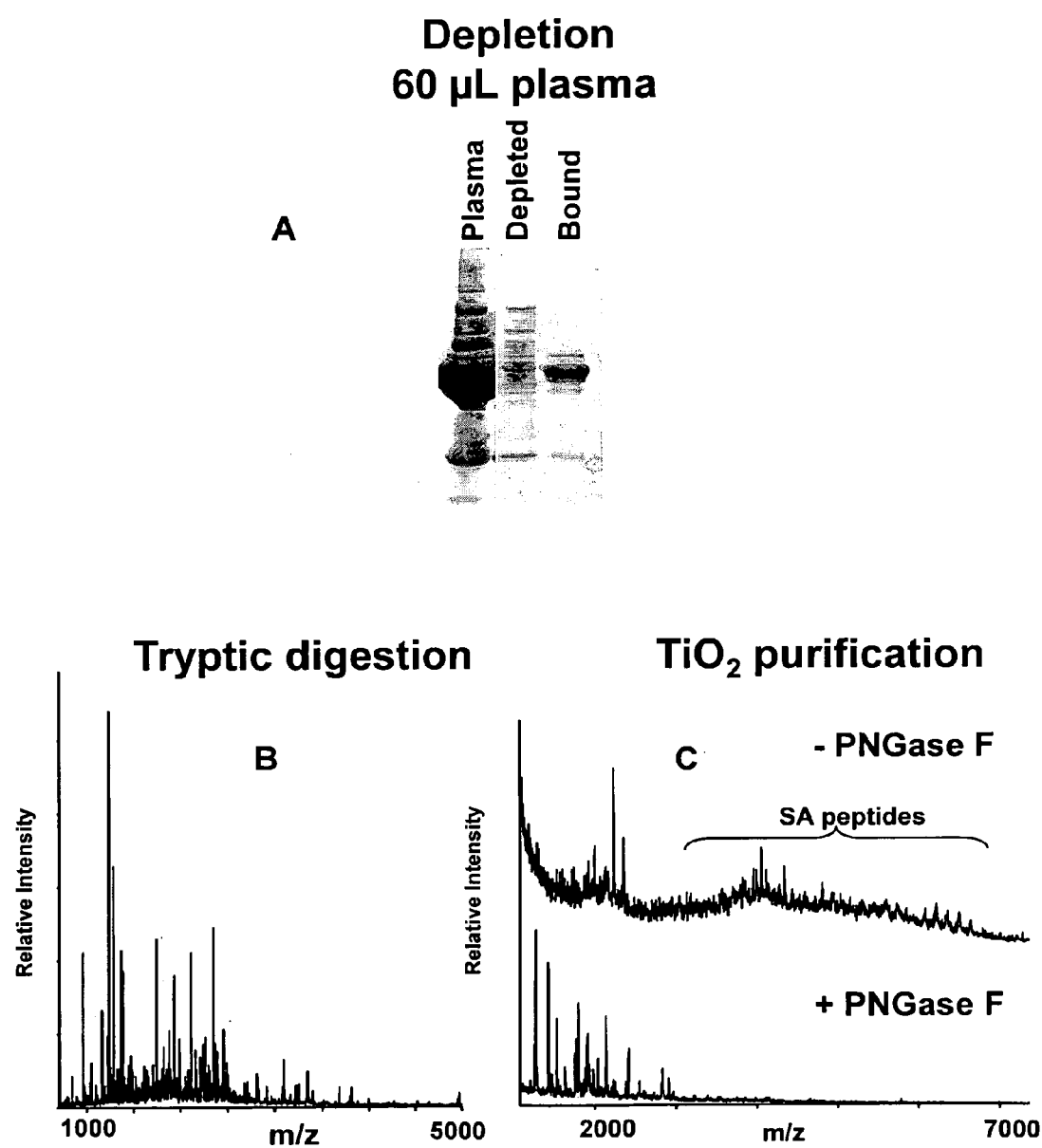
FIG. 5A shows SDS gel electrophoresis of low abundance human plasma proteins before and after depletion.
FIG. 5B shows MALDI mass spectra of tryptic fragments of depleted low abundance human plasma proteins after reduction and alkylation of the cysteins and subsequently with alkaline phosphatase.
FIG. 5C shows MALDI mass spectra of tryptic fragments of depleted low abundance human plasma proteins after reduction and alkylation of the cysteins and subsequently with alkaline phosphatase and then purified by $TiO_2$.

FIG. 5: MALDI Mass Spectra of Tryptic Fragments of Low Abundance Human Plasma Proteins Before and after Isolation of Sialylated Peptides.

Plasma was depleted for the 6 most abundant plasma proteins using an immune-depletion column (Agilent) SDS gel electrophoresis of the plasma proteins before and after depletion are shown in (FIG. 4 A). The depleted fraction was treated with trypsin after reduction and alkylation of the cysteins and subsequently with alkaline phosphatase. An aliquot of the tryptic peptides was analyzed by MALDI MS (FIG. 4 B). An aliquot of the tryptic peptides was purified by $TiO_2$ and a small amount of eluted glycopeptides were analyzed by MALDI MS (FIG. 4 C). The signals at the high mass area originate from sialylated glycopeptides. The remaining sialylated glycopeptides were treated with N-glycosidase F and an aliquot of the deglycosylated peptides was analyzed by MALDI MS (FIG. 4 C inset).

FIG. 6: LC-MSMS Spectra of Sialylated Tryptic Fragments Isolated from Human Plasma Samples.

Deglycosylated peptides originating from $TiO_2$ purification of human plasma were analyzed by liquid chromatography mass spectrometry for mass measurement and sequence information. Two examples of more than 200 deglycosylated peptides found in the sample are shown. (FIG. 6A) shows the fragment ion spectrum of the collision induced dissociated (CID) doubly charged peptide at m/z 666.88. This fragment ion spectrum can be assigned to the sequence IGGIWTWVGTNK(SEQ ID NO. 14) from L-Selectin where the N is deglycosylated. (FIG. 6 B) shows the fragment ion spectrum of the collision induced dissociated (CID) doubly charged peptide at m/z 832.46. This fragment ion spectrum can be assigned to the sequence FNPGAESWLSNSTLK (SEQ ID NO. 15) from Multimerin-1 where the N is deglycosylated. As shown, both peptides contain glycan structures which include sialic acids.

FIG. 7: Strategy for Identification of Biomarkers of Conditions Associated with a Change of Sialylation Status.

A strategy is shown for identification of potential biomarkers of conditions associated with a change of sialylation status, in this case bladder cancer. The control and bladder cancer samples are reduced and alkylated to block cysteines and subsequently digested with trypsin. The tryptic peptide mix is lyophilized and re-digested with trypsin in $O^{16}$ buffer (control) and $O^{18}$ buffer (bladder cancer). The two samples are mixed 1:1 (checked using MALDI MS) and loaded onto TiO2 in DHB loading buffer. The purified sialylated glycopeptides are then analyzed by mass spectrometry or liquid chromatography coupled to mass spectrometry (LC-MS). Alternatively the sialylated glycopeptides can be deglycosylated and the deglycosylated peptides analyzed by mass spectrometry or LC-MS.

FIG. 8: MALDI and LC-MSMS Spectra of $O^{16}$- and $O^{18}$-Sialylated Tryptic Fragments of Low Abundance Plasma Proteins from Normal and Bladder Cancer Samples.

Purified sialylated glycopeptides labeled with $O^{18}$ (bladder cancer) and normal ($O^{16}$) were analyzed by LC-MS shown as an ion trace in (FIG. 8 A) Shown in (FIG. 8 B) is the mass spectrum of the sialylated glycopeptides that elute from the reverse-phased LC-column at the time labelled 1. The circles represent signals from the same peptide by with large glycan-mircoheterogeneity all of which glycans have terminal sialic acid moieties. The insets compare isotopic labelling of corresponding sialylated from control and bladder cancer samples. In this case the peptide is significantly over-sialylated in bladder cancer. (FIG. 8 C) shows the mass spectrum of sialylated glycopeptides that elute from the reversed-phase LC-column at the time labelled 2. The circles represent the signals from the same peptide but with large glycan-microheterogeneity all of which glycans have terminal sialic acid moieties. The inset compares isotopic labelling of corresponding sialylated peptides from control and bladder cancer samples. In this case the peptide is not changed with respect to sialic acid content between control and bladder cancer samples.

FIG. 9: MALDI and LC-MSMS Spectra of $O^{16}$- and $O^{18}$-Sialylated Tryptic Fragments of Low Abundance Plasma Proteins from Normal and Bladder Cancer Samples.

Figure 9A:
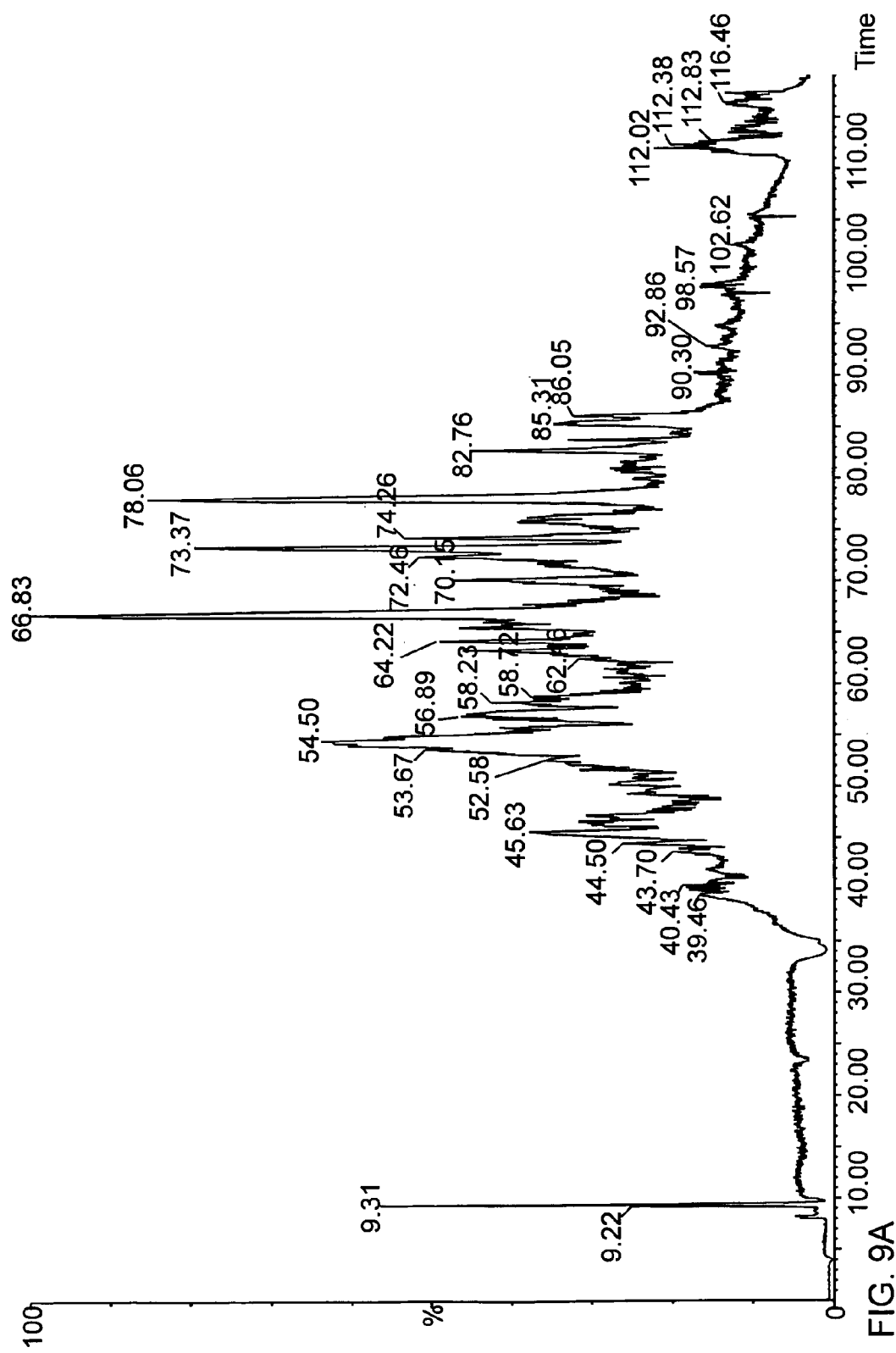
FIG. 9A shows LC-MSMS spectra of purified sialylated glycopeptides from plasma labeled with $O^{18}$ (bladder cancer) and $O^{16}$ (normal).
Figure 9B:
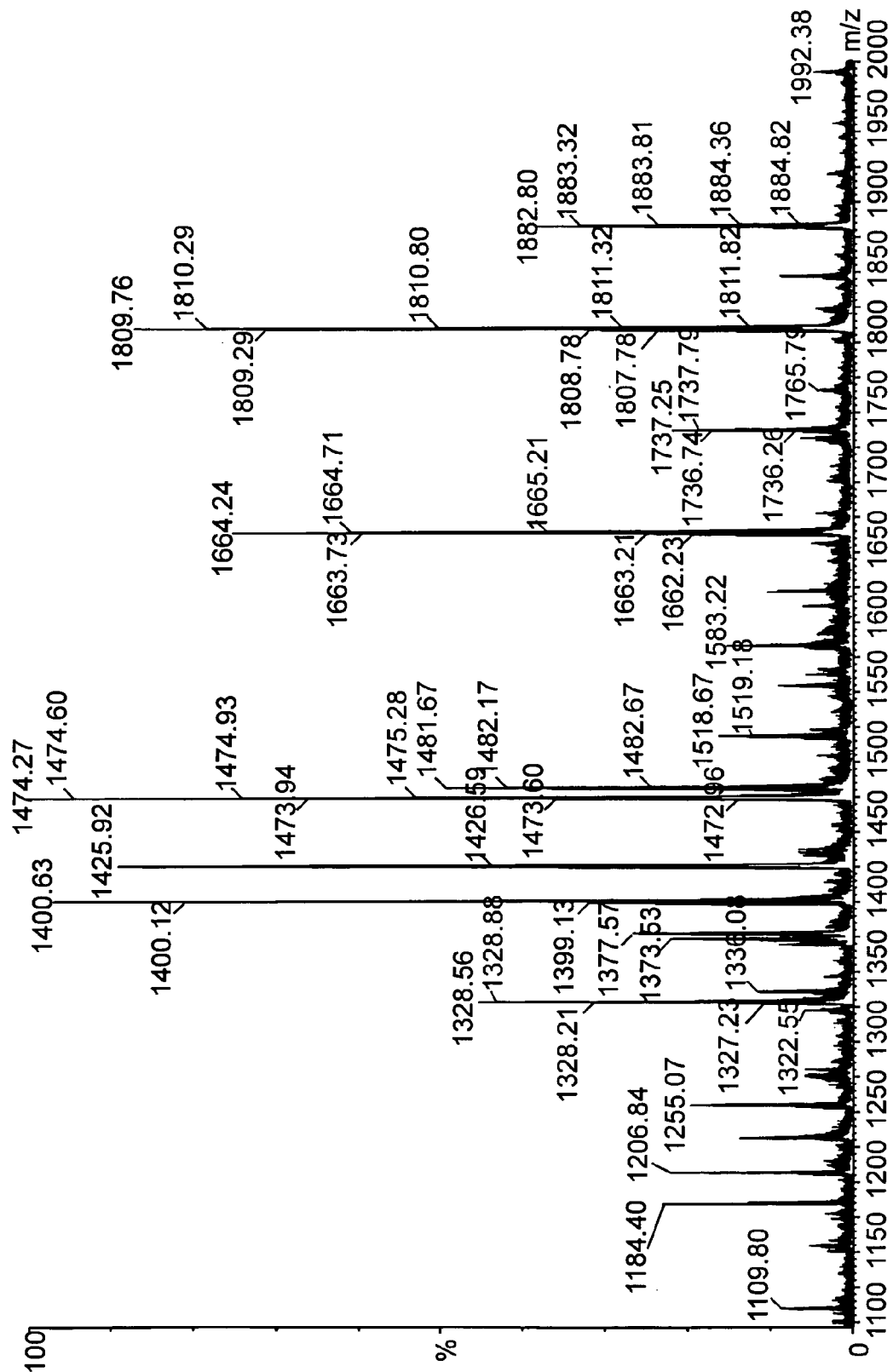
FIG. 9B shows MALDI mass spectra of purified sialylated glycopeptides from plasma labeled with $O^{18}$ (bladder cancer) and $O^{16}$ (normal) eluded from a reversed-phase LC-column.
Figure 9C:
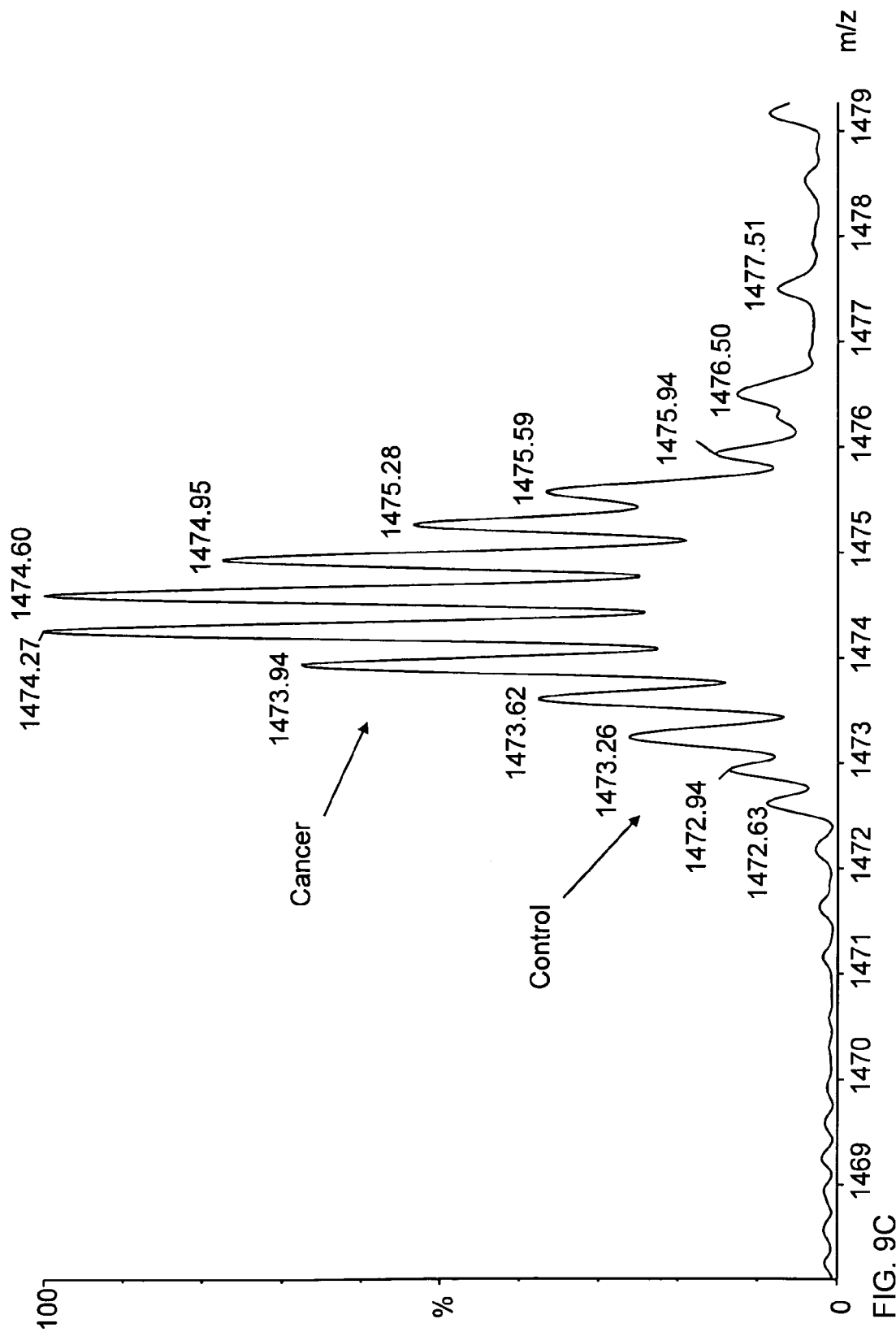
FIG. 9C shows MALDI mass spectra of triply charged sialylated glycopeptides at m/z 1472.61 (control) and 1473.94 (bladder cancer) eluted from a reversed-phase LC-column.
Figure 9D:
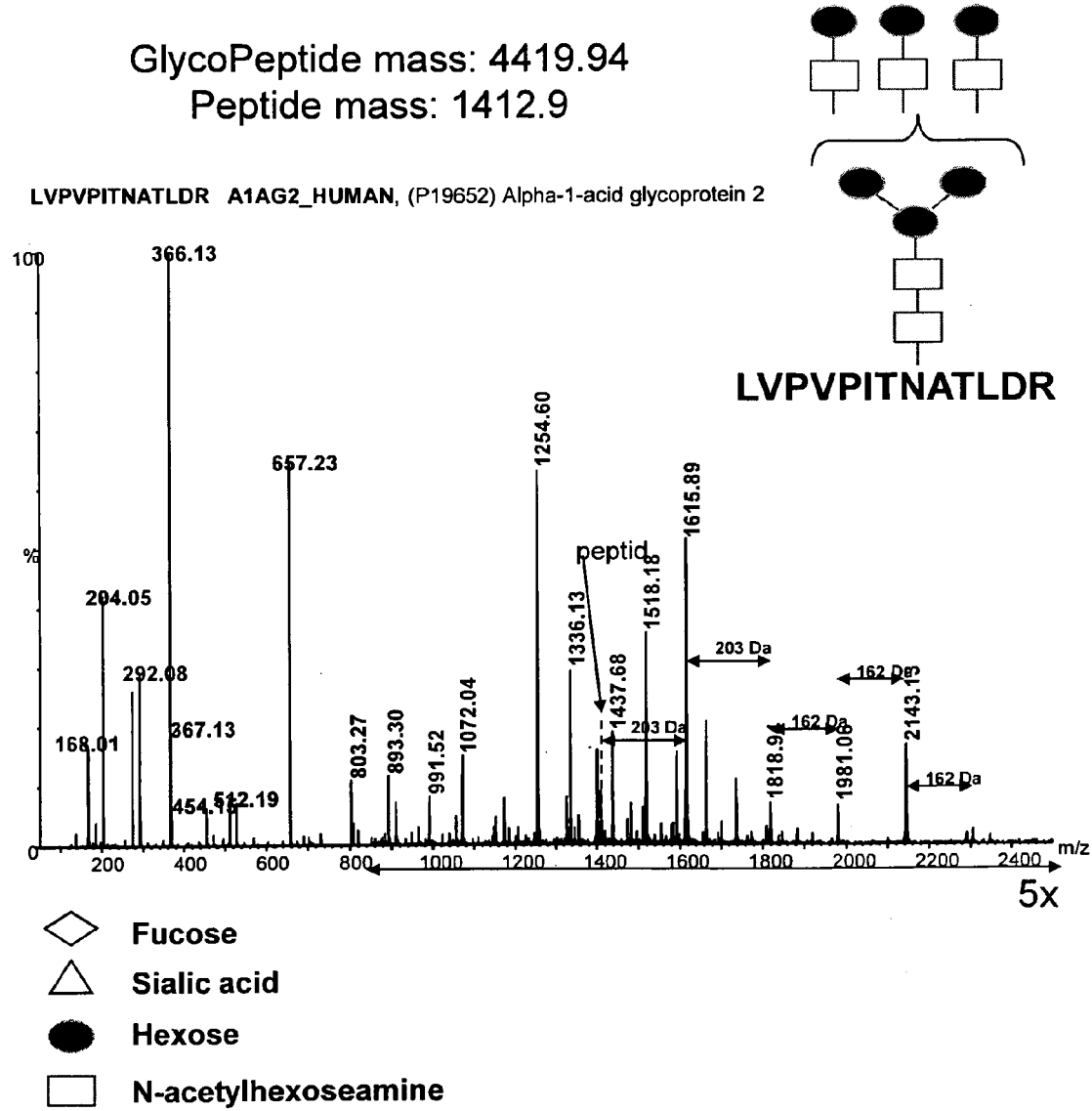
FIG. 9D shows the fragment ion spectrum of the m/z 1473.94 signal shown in FIG. 9C following tandem MS and collision induced dissociation.
Figure 9E:
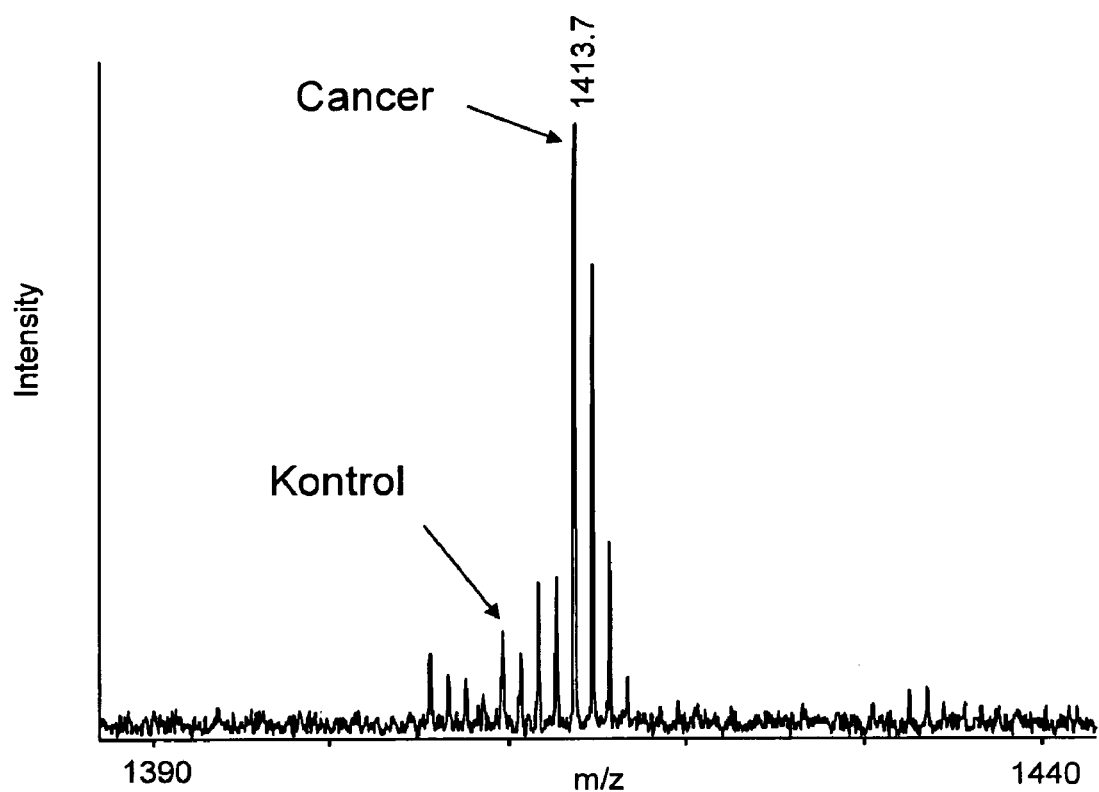
FIG. 9E shows the isotope distribution of the peptide shown in FIG. 9D after deglycosylation with N-glycosidase F.
Figure 9F:
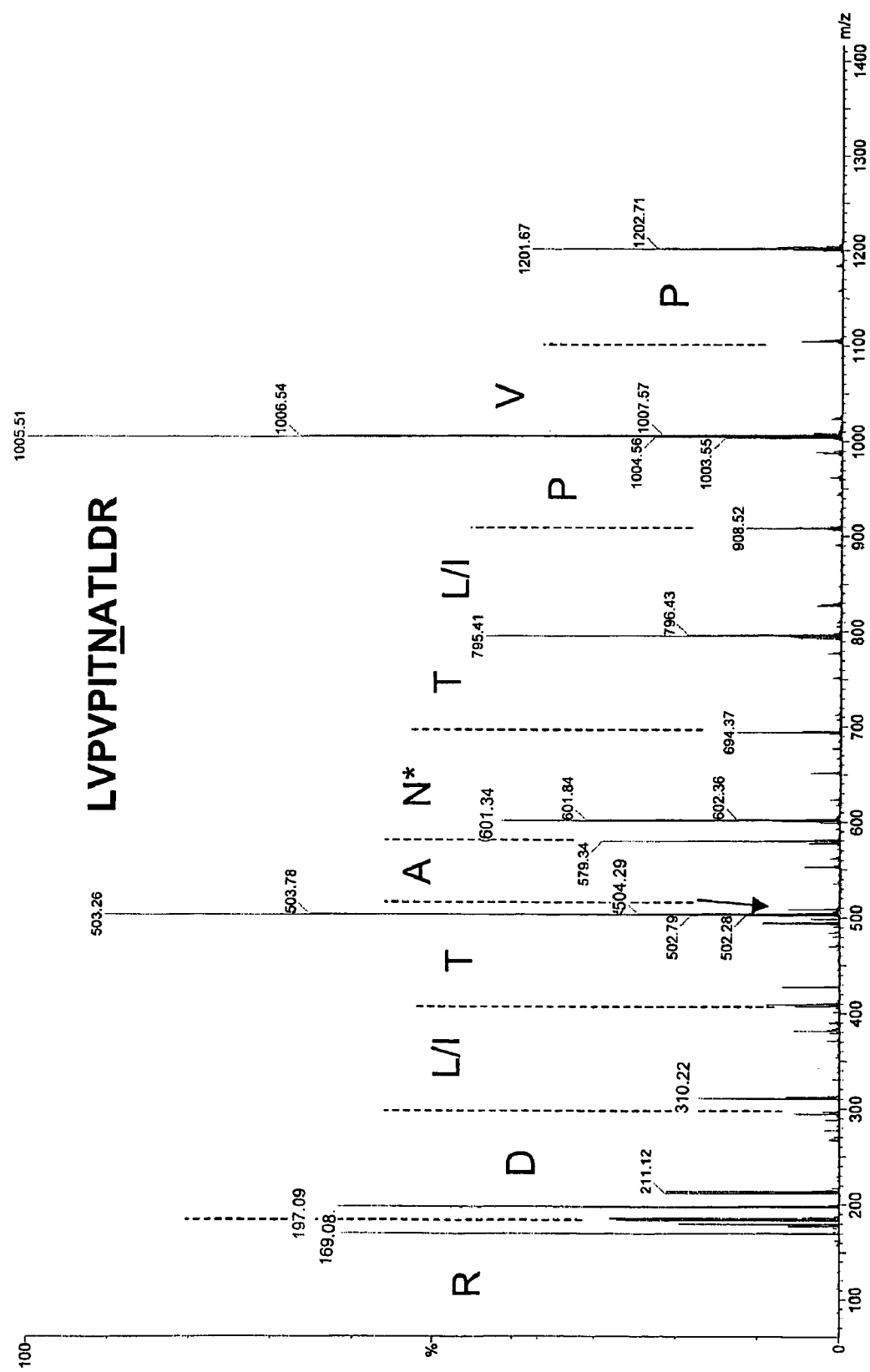
FIG. 9F shows the fragment ion spectrum of the peptide shown in FIG. 9E upon collision induced dissociation.

Purified sialylated glycopeptides from plasma labelled with $O^{18}$ (bladder caner) and normal ($O^{16}$) were analyzed by LC-MS as shown as an ion trace in (FIG. 9A.) Shown in (FIG. 9 B) is the mass spectrum of sialylated glycopeptides that elute from the reversed-phase LC-column at the time labelled with a circle. (FIG. 9 C) shows the mass spectrum of the triply charged sialylated glycopeptides at m/z 1472.61 (control) and 1473.94 (bladder cancer). The signal from the peptide in the bladder cancer sample is significantly higher than that from the corresponding peptide from the control sample. This indicates that the protein from which this peptide is derived is over-sialylated in bladder cancer. The signal at m/z 1473.94 was selected for tandem MS and collision induced dissociation and the fragment ion spectrum is shown in (FIG. 9 D). From the masses of the fragments and the knowledge that N-linked glycans always have a common core structure ((N-acetylglycoseamine)$_2$(Mannose)$_3$) the mass of the peptide can be calculated and a putative composition of the glycan structure proposed. This glycan structure shown in the inset in the right part of (FIG. 9 D). Monosaccharide symbols are indicated. The isotope distribution observed after deglycosylation with N-glycosidase F (PN-GaseF), which gives a mass increment of 1 Da for each N-linked glycosylation, is shown in (FIG. 9 E). In this case, a large increase is observed in the bladder cancer sample. Upon collision induced dissociation this peptide is fragmented to give the fragment ion spectrum shown in (FIG. 9 F). From this fragment ion spectrum the sequence LVPVPITNATLDR (SEQ ID NO. 1) can be read, which is derived from Human Alpha-1-acid glycoprotein 2. The N in NAT is glycosylated.

FIG. 10: Development of the Procedure for Enrichment of Phosphorylated Peptides Using TiO$_2$ Micro-Columns.

MALDI mass spectra obtained from peptide mixture 1 (A) without TiO$_2$ enrichment (B) enriched by TiO$_2$ using acetic acid as loading buffer and NH$_4$HCO$_3$ pH 9.0 as elution buffer (C) subsequent elution with NH$_4$OH, pH 10.5 (D) enriched by TiO$_2$ using 0.1% TFA as loading buffer and NH$_4$OH, pH 10.5 as elution buffer. The phosphorylated peptides are marked with asterisks.

FIG. 11: Further Development of the Procedure for Enrichment of Phosphorylated Peptides Using TiO$_2$ Micro-Columns.

MALDI mass spectra obtained from peptide mixture 1 (A) enriched by TiO$_2$ using 0.1% TFA as loading buffer and NH$_4$OH, pH 10.5 as elution buffer (B) enriched by TiO$_2$ using 0.1% TFA as loading buffer and acidic DHB solution as elution buffer (C) subsequent elution with NH$_4$OH, pH 10.5 (D) enriched by TiO$_2$ using acidic DHB solution as loading buffer and NH$_4$OH, pH 10.5 as elution buffer. The inserts show the m/z range 1920 to 1975. The phosphorylated peptides are marked with asterisks.

FIG. 12: The Effect of the DHB Concentration in the Loading Buffer on the Selective Enrichment of Phosphorylated Tryptic α-Casein Peptides Using TiO$_2$ Micro-Columns.

The MALDI mass spectrum of TiO$_2$ enriched peptides from peptide mixture 1 using 0, 1, 10 and 20 mg/ml DHB (in 80% acetonitrile/0.1% TFA), are shown in A, B, C and D, respectively. The circles mark the loss of phosphoric acid by metastable fragmentation and the m/z ranges containing non-phosphorylated peptides are marked with grey boxes.

FIG. 13: Enrichment of Phosphorylated Peptides.

Phosphorylated peptides enriched from peptide mixture 2 (ratio 1:1). MALDI mass spectrum obtained (A) without TiO$_2$ enrichment (B) enriched by TiO$_2$ using acetic acid as loading buffer (C) enriched by TiO$_2$ using 0.1% TFA as loading buffer (D) enriched by TiO$_2$ using DHB (300 mg/mL) as loading buffer. The phosphorylated peptides are marked with asterisks.

FIG. 14: The Effect of the DHB Concentration on the Selective Enrichment of Phosphorylated Peptides by TiO$_2$.

Enriched phosphorylated peptides were obtained from peptide mixture 2 (ratio 1:1). The MALDI mass spectra obtained from TiO$_2$ enrichments in a loading buffer containing 0, 10, 20, 50, 100 and 200 mg/ml DHB are shown in A, B, C, D, E and F, respectively. The phosphorylated peptides are labelled and the m/z ranges containing non-phosphorylated peptides are marked with grey boxes.

FIG. 15: Comparison of the Performance of $TiO_2$ Micro-Columns and IMAC Beads for the Selective Enrichment of Phosphorylated Peptides from Complex Mixtures.

Phosphorylated peptides from peptide mixture 2 with the ratios 1:1, 1:10 and 1:50, were enriched by $TiO_2$ or IMAC (PHOSselect™). MALDI mass spectra obtained from $TiO_2$ enrichments of the phosphorylated peptides in the three peptide mixtures are shown in A, B and C, respectively. The MALDI mass spectra of similar enrichments using IMAC beads are shown in D, E and F, respectively. The phosphorylated peptides detected here are marked with dots in (A and D).

FIG. 16: The Effect of Various Acids on the Selective Binding of Phosphorylated Peptides to $TiO_2$.

The peptides were obtained from peptide mixture 2 (ratio 1:1). The MALDI mass spectra obtained from $TiO_2$ enrichment using a loading buffer of (A) 0.1% TFA (B) 0.13 M phosphoric acid (C) 0.13 M benzoic acid (D) 0.13 M DHB. The asterisks in (D and B) mark phosphorylated peptides.

Figure 17:
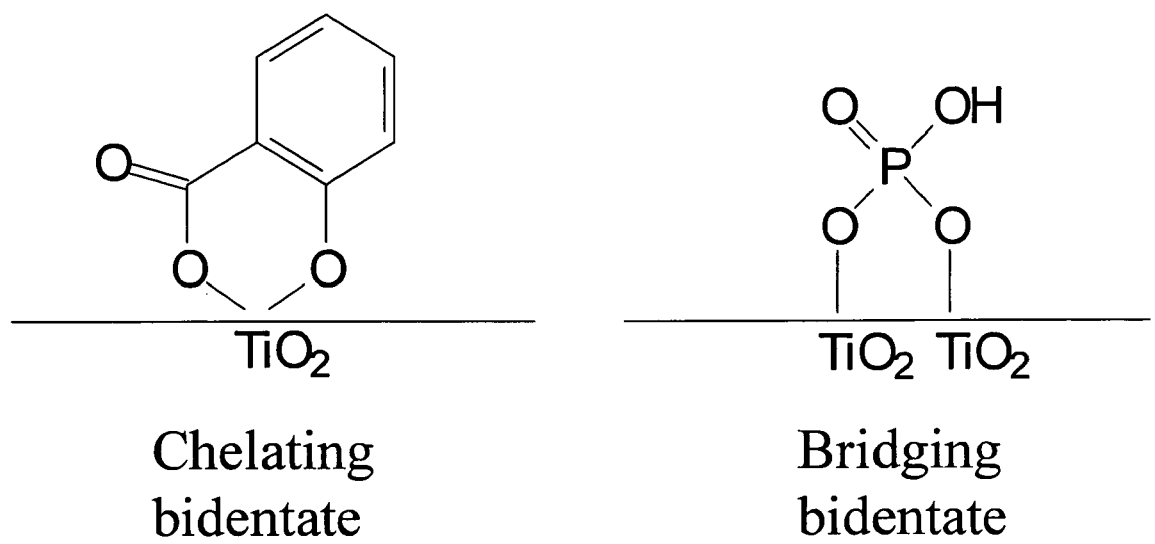
FIG. 17 shows binding modes of phosphate and salicylate species adsorbed to TiO$_2$

FIG. 17: Binding Modes of Phosphate and Salicylate Species Adsorbed to $TiO_2$.

FIG. 18: Purification of Phosphopeptides Derivatized while Immobilized on Stationary Phase Shown is purification of phosphopeptides from alpha casein using TiO2 and derivatization of the peptides while immobilized on stationary phase using the reagent SPITC (4-sulfophenyl isothiocyanate).

FIG. 19: Identification of the NVSSGS$^p$PWYGPDR (SEQ ID NO. 6) Phosphopeptide in the Lhcb1 Protein.

Panel A, MALDI-Q-TOF tandem MS spectrum of the phosphopeptide with parent molecular ion at 1501.60 m/z. The indicated differences of 80 and 98 Da correspond to the neutral losses of $HPO_3$ and $H_3PO_4$, respectively. Panel B, The product ion spectrum obtained after nanoelectrospray ionization and CID of the same peptide. The selected doubly charged molecular ion with m/z 751.29 is indicated along with the ion that underwent the neutral loss of phosphoric acid (m/z 702.30). The detected b (N-terminal) and y (C-terminal) fragment ions are labelled in the spectra. Fragment ions corresponding to the loss of ammonia (17 Da) and water (18 Da) are marked with asterisks and superscript 0, respectively.

Figure 20:
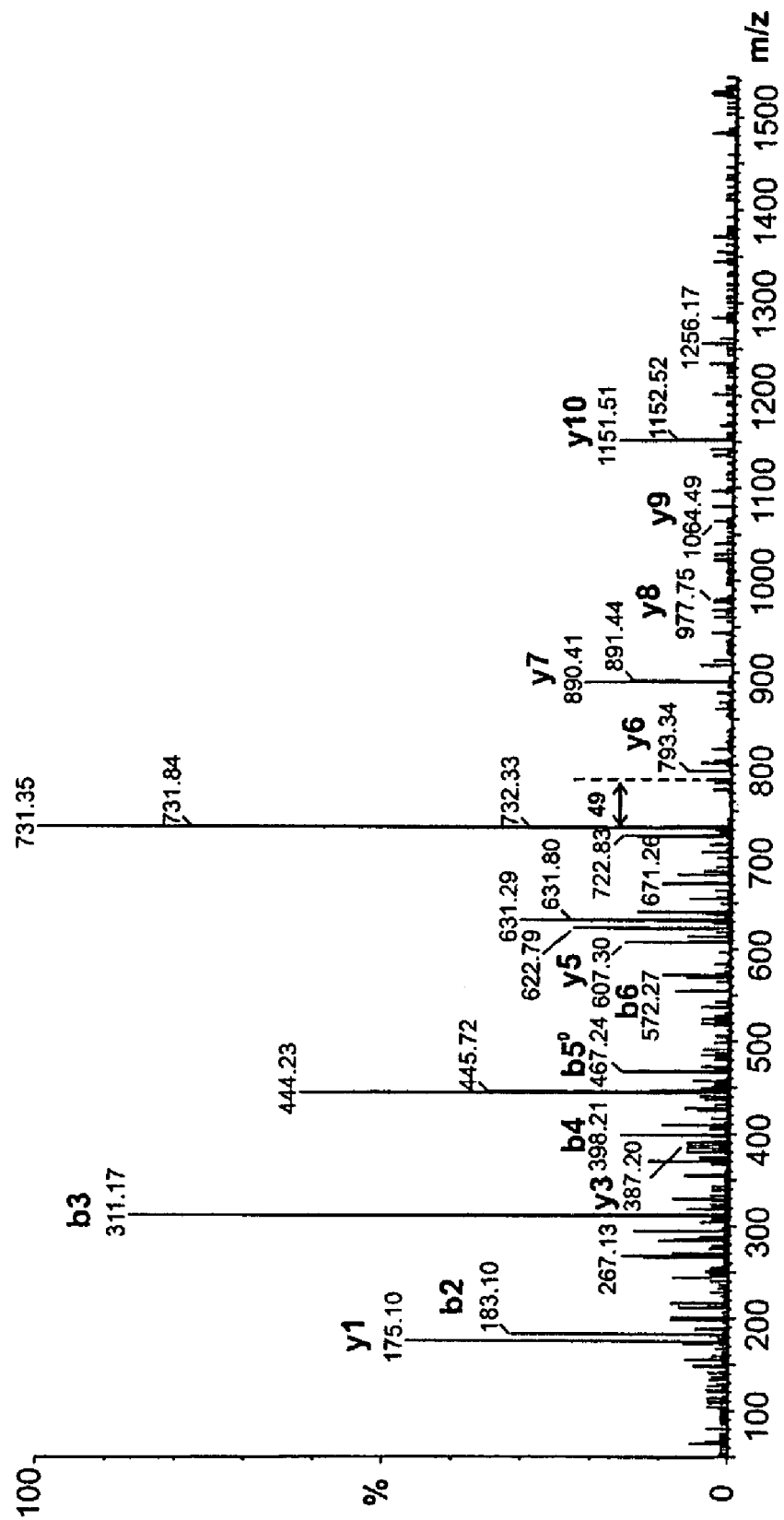
FIG. 20 shows identification of the T$^P$VQSSSPWYGPDR (SEQ ID NO. 3) phosphopeptide in the Lhcb1 protein.

FIG. 20: Identification of the T$^P$VQSSSPWYGPDR (SEQ ID NO. 3) Phosphopeptide in the Lhcb1 Protein.

ESI-Q-TOF tandem MS spectrum of the doubly charged parent molecular ion with 780.30 m/z. The detected b (N-terminal) and y (C-terminal) fragment ions are labelled in the spectrum. Fragment ions corresponding to the loss of water (18 Da) are marked with the superscript 0. The indicated difference of 49 correspond with the neutral loss of phosphoric acid from the doubly charged parent ion at m/z 780.30.

FIG. 21: Identification of SPT$^P$GEVIFGGETM$_{ox}$R (SEQ ID NO. 9) Phosphopeptide in the CP43 Protein.

ESI-Q-TOF tandem MS spectrum of the doubly charged parent molecular ion with m/z=788.81 (shown by an arrow). The indicated differences of 49 and 32 Da correspond to the neutral losses of $H_3PO_4$ and $CH_3SOH$, respectively. The detected b (N-terminal) and y (C-terminal) fragment ions are labelled in the spectrum. Fragment ions corresponding to the loss of ammonia (17 Da) and water (18 Da) are marked with asterisks and superscript 0, respectively. The superscript p designates the b ions with the phosphate group.

FIG. 22: Identification of N-terminal Phosphopeptides in the CP43 Protein.

Panel A, MALDI-Q-TOF tandem MS spectrum of the chymotryptic phosphopeptide Ac-T$^P$LFNGt$^P$L (SEQ ID NO. 11) where the lowercase t designates the secondary phosphorylation site and Ac- indicates acetylation. The indicated differences of 98 and 18 Da correspond to the neutral losses of $H_3PO_4$ and water, respectively. Panel B, Tandem MS spectrum obtained after nanoelectrospray ionization and CID of the peptide NGt$^P$LT$^P$LAGRDQETTGF (SEQ ID NO. 12). The indicated difference of 49 Da correspond to the neutral loss of $H_3PO_4$ from the doubly charged parent molecular ion at 880.93 m/z. The detected b (N-terminal) and y (C-terminal) fragment ions are labelled in the spectra. Gray b and y ions correspond to the fragments due to the secondary phosphorylation site. Fragment ions corresponding to the loss of ammonia (17 Da) and water (18 Da) are marked with asterisks and superscript 0, respectively.

Figure 23:
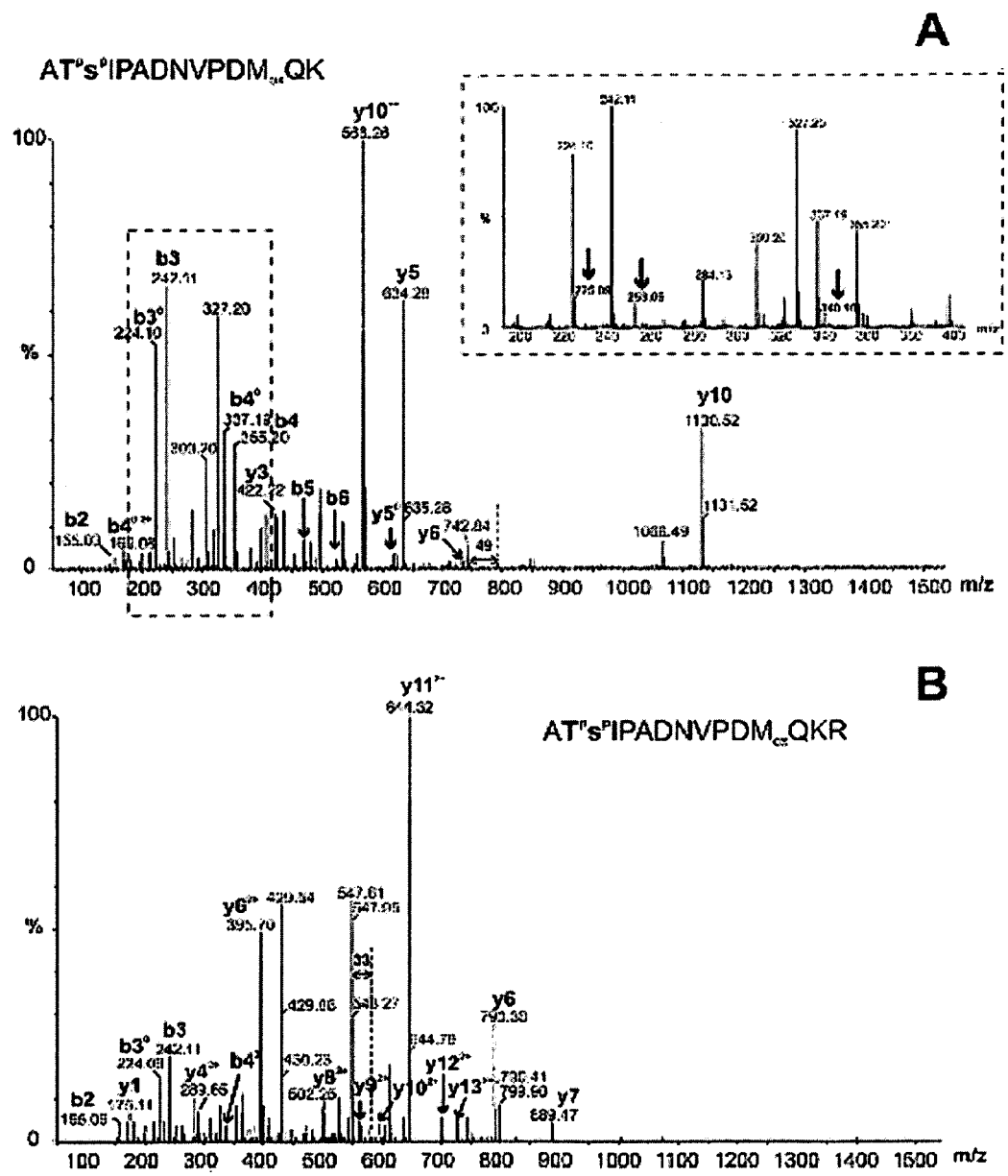
FIG. 23A shows Tandem MS spectrum obtained after nanoelectrospray ionization and CID of the peptide AT$^P$s$^P$I-PADNVPDM$_{OX}$OK.
FIG. 23B shows Tandem MS spectrum obtained after nanoelectrospray ionization and CID of the peptide AT$^P$s$^P$I-PADNVPDM$_{OX}$QKR.

FIG. 23: Identification of N-terminal phosphopeptides in the Rieske Fe—S Protein.

Panel A, Tandem MS spectrum obtained after nanoelectrospray ionization and CID of the peptide AT$^P$s$^P$IPADNVPD-M$_{ox}$QK (SEQ ID NO. 13). The indicated difference of 49 Da correspond to the neutral loss of $H_3PO_4$ from the doubly charged parent molecular ion at 791.81 m/z. Inset displays a zoom of the spectrum in the region of m/z 200-400 for indication of some fragment ions suggesting two mono-phosphorylated versions of this peptide. Panel B points out the tandem MS spectrum obtained after nanoelectrospray ionization and CID of the peptide AT$^P$s$^P$IPADNVPDM$_{ox}$QKR (SEQ ID NO. 16). The shown difference of 33 Da corresponds to the neutral loss of $H_3PO_4$ from the triply charged parent molecular ion at 580.24 m/z. The detected b (N-terminal) and y (C-terminal) fragment ions are labelled in the spectra. Fragment ions corresponding to the loss of water (18 Da) are marked with superscript 0.

CITED REFERENCES

1. C. A. Buck, M. C. Glick, and L. Warren. 1971. Glycopeptides from the surface of control and virus-transformed cells *Science* 172: 169-171.
2. G. G. Wickus and P. W. Robbins. 1973. Plasma membrane proteins of normal and Rous sarcoma virus-transformed chick-embryo fibroblasts *Nat. New Biol.* 245: 65-67.
3. T. Feizi. 1985. Demonstration by monoclonal antibodies that carbohydrate structures of glycoproteins and glycolipids are onco-developmental antigens *Nature* 314: 53-57.
4. S. Hakomori. 1986. Tumor associated glycolipid antigens, their metabolism and organization *Chem. Phys. Lipids* 42: 209-233.
5. T. Miyagi, T. Wada, K. Yamiguchi and K. Hata 2004 Sialidase and malignancy: a minireview. Glycoconj. J. 20(3): 189-198.
6. E. Pearlstein, P. L. Salk, G. Yogeeswaran, and S. Karpatkin. 1980. Correlation between spontaneous metastatic potential, platelet-aggregating activity of cell surface extracts, and cell surface sialylation in 10 metastatic-variant derivatives of a rat renal sarcoma cell line *Proc. Natl. Acad. Sci.* 77: 4336-4339.
7. G. Yogeeswaran and P. L. Salk. 1981. Metastatic potential is positively correlated with cell surface sialylation of cultured murine tumor cell lines *Science* 212: 1514-1516.
8. J. Dennis, C. Waller, R. Timpl, and V. Schirrmacher. 1982. Surface sialic acid reduces attachment of metastatic tumour cells to collagen type IV and fibronectin *Nature* 300: 274-276.
9. S. D. Hoff, Y. Matsushita, D. M. Ota, K. R. Cleary, T. Yamori, S. Hakomori, and T. Irimura. 1989. Increased expression of sialyl-dimeric LeX antigen in liver metastases of human colorectal carcinoma *Cancer Res.* 49: 6883-6888.

10. Y. S. Kim, J. Gum, and 1. Brockhausen. 1996. Mucin glycoproteins in neoplasia *Glycoconj. J.* 13: 693-707.
11. K. Fukushima, M. Hirota, P. I. Terasaki, A. Wakisaka, H. Togashi, D. Chia, N. Suyama, Y. Fukushi, E. Nudelman, and S. Hakomori. 1984. Characterization of sialosylated Lewis$^x$ as a new tumor-associated antigen Cancer Res. 44: 5279-5285.
12. S, Nakamori, H. Furukawa, M. Hiratsuka, T. Iwanaga, S. Imaoka, O. Ishikawa, T. Kabuto, Y. Sasaki, M. Kameyama, S. Ishiguro, and T. Irimura. 1997. Expression of carbohydrate antigen sialyl Lea: A new functional prognostic factor in gastric cancer *J. Clin. Oncol.* 15: 816-825.
13. S, Nakamori, M. Kameyama, S. Imaoka, H. Furukawa, O. Ishikawa, Y. Sasaki, Y. Izumi, and T. Irimura. 1997. Involvement of carbohydrate antigen sialyl Lewis$^x$ in colorectal cancer metastasis *Dis. Colon Rectum* 40: 420-431.
14. Y. J. Kim, L. Borsig, N. M. Varki, and A. Varki. 1998. P-selectin deficiency attenuates tumor growth and metastasis *Proc. Natl. Acad. Sci.* 95: 9325-9330.
15. Passaniti A, Hart G W (1988) Cell surface sialylation and tumor metastases: metastatic potential of B16 melanoma variants correlates with their relative number of specific penultimate oligosaccharide structures. J. Biol. Chem. 263, 7591-7603.
16. Yogeswaran G (1983) Cell surface glycolipids and glycoproteins in malignant transformation. Adv. Cancer Res. 38, 289-350.
17. O. Seksek, J. Biwersi, and A., S. Verkman. Evidence against Defective trans-Golgi Acidification in Cystic Fibrosis. *J. Biol. Chem.* (1996) 271 (26): 15542-15546.
18. M. Lanteri, V. Giordanengo, N. Hiraoka, J. G. Fuzibet, P. Auberger, M. Fukuda, L. G. Baum, J. C. Lefebvre. Altered T cell surface glycosylation in HIV-1 infection results in increased susceptibility to galectin-1-induced cell death. *Glycobiology* (2003) 13 (12):909-18.
19. M. T. Goodarzi, M. Shafiei, H. Nomani, A. Shahriarahmadi. Relationship Between Total and Lipid-bound Serum Sialic Acid and Some Tumor Markers. *IJMS* (2005) 30 (3): 124-127.
20. Selma Süer Gökmen, Cemal Kazezoglu, Erhan Tabakoglu, Gundeniz Altiay, Özgül Güngör, Mevlüt Türe. Serum Total Sialic Acid Levels in Lung Cancer Patients of Different Histological Types with and No Extrapulmonary Metastases. *Turk J. Biochem.* (2004) 29 (4): 262-267.
21. Yoichiro Kakugawa, Tadashi Wada, Kazunori Yamaguchi, Hideaki Yamanami, Kiyoaki Ouchi, Ikuro Sato, and Taeko Miyagi. Up-regulation of plasma membrane-associated ganglioside sialidase (Neu3) in human colon cancer and its involvement in apoptosis suppression. *Proc Natl Acad Sci USA*. (2002); 99 (16): 10718-10723.
22. He Z, Aristoteli L P, Kritharides L, Garner B. HPLC analysis of discrete haptoglobin isoform N-linked oligosaccharides following 2D-PAGE isolation. *Biochem Biophys Res Commun*. (2006) 5; 343(2):496-503.
23. Sebzda T, Saleh Y, Gburek J, Warwas M, Andrzejak R, Siewinski M, Rudnicki J. Total and lipid-bound plasma sialic acid as diagnostic markers in colorectal cancer patients: correlation with cathepsin B expression in progression to Dukes stage. *J Exp Ther Oncol.* 2006; 5(3): 223-9.
24. Odani H, Hiki Y, Takahashi M, Nishimoto A, Yasuda Y, Iwase H, Shinzato T, Maeda K. Direct evidence for decreased sialylation and galactosylation of human serum IgA1 Fc O-glycosylated hinge peptides in IgA nephropathy by mass spectrometry. *Biochem Biophys Res Commun.* (2000) 271(1):268-74.
25. O. Seksek, J. Biwersi, and A. S. Verkman. Evidence against Defective trans-Golgi Acidification in Cystic Fibrosis. *The Journal of Biological Chemistry.* (1996): 15542-15548.
26. Larsen, M. R., Thingholm, T. E., Jensen, O. N., Roepstorff, P., and Jorgensen, T. J. D., Highly selective enrichment of phosphorylated peptides from peptide mixtures using titanium dioxide microcolumns. Mol. Cell. Proteomics (2995) 4(7):873-886.
27. Hood, B. L., Lucas, D. A. Quantitative analysis of the low molecular weight serum proteome using $O^{18}$ stable isotope labelling in lung tumor xenograft mouse model. J. Am. Soc. Mass. Spectrom. (2005) 16(8):1221-1230.
28. Neville, D. C., Rozanas, C. R., Price, E. M., Gruis, D. B., Verkman, A. S., and Townsend, R. R. (1997) Evidence for phosphorylation of serine 753 in CFTR using a novel metal-ion affinity resin and matrix-assisted laser desorption mass spectrometry. Protein Sci. 6, 2436-2445.
29. Posewitz, M. C., and Tempst, P. (1999) Immobilized gallium(III) affinitychromatography of phosphopeptides. *Anal. Chem.* 71, 2883-2892.
30. Figeys, D., Gygi, S. P., Zhang, Y., Watts, J., Gu, M., and Aebersold, R. (1998) Electrophoresis combined with novel mass spectrometry techniques: powerful tools for the analysis of proteins and proteomes. *Electrophoresis* 19, 1811-1818
31. Li, S. H., and Dass, C. (1999) Iron(111)-immobilized metal ion affinity chromatography and mass spectrometry for the purification and characterization of synthetic phosphopeptides. *Anal. Biochem.* 270, 9-14.
32. Ficarro, S., Chertihin, O., Westbrook, V. A., White, F., Jayes, F., Kalab, P., Marto, J. A., Shabanowitz, J., Herr, J. C., Hunt, D. F., and Visconti, P. E. (2003) Phosphoproteome analysis of capacitated human sperm. Evidence of tyrosine phosphorylation of a kinase-anchoring protein 3 and valosin-containing protein/p97 during capacitation. *J. Biol. Chem.* 278, 11579-11589.
33. Nuhse, T. S., Stensballe, A., Jensen, O. N., and Peck, S. C. (2003) Largescale analysis of in vivo phosphorylated membrane proteins by immobilized metal ion affinity chromatography and mass spectrometry. *Mol. Cell. Proteomics* 2, 1234-1243.
34. Gruhler, A., Olsen, J. V., Mohammed, S., Mortensen, P., Faergeman, N. J., Mann, M., and Jensen, O. N. (2005) Quantitative phosphoproteomics applied to the yeast pheromone signalling pathway. *Mol. Cell. Proteomics* 4, 310-327.
35. Ficarro, S. B., McCleland, M. L., Stukenberg, P. T., Burke, D. J., Ross, M. M., Shabanowitz, J., Hunt, D. F., and White, F. M. (2002) Phosphoproteome analysis by mass spectrometry and its application to *Saccharomyces cerevisiae*. *Nat. Biotechnol.* 20, 301-305.
36. Seward, R. J., Perlman, D. H., Berg, E. A., Hu, J., and Costello, C. E. (2004) in 52nd ASMS Conference on Mass Spectrometry and Allied Topics, Nashville, May 23-27, 2004, Abstr. A042056, American Society for Mass Spectrometry, Santa Fe, N. Mex.
37. Stewart, I. I., Thomson, T., and Figeys, D. (2001) 0-18 labelling: a tool for proteomics. *Rapid Commun. Mass Spectrom.* 15, 2456-2465.
38. Speicher, K. D., Kolbas, O., Harper, S., and Speicher, D. W. (2000) Systematic analysis of peptide recoveries from in-gel digestions for protein identifications in proteome studies. *J. Biomol. Tech.* 11, 74-86.
39. Oda, Y., Nagasu, T., and Chait, B. T. (2001) Enrichment analysis of phosphorylated proteins as a tool for probing the phosphoproteome. *Nat. Biotechnol.* 19, 379-382.

40. McLachlin, D. T., and Chait, B. T. (2003) Improved-elimination-based affinity purification strategy for enrichment of phosphopeptides. *Anal. Chem.* 75, 6826-6836.
41. Pinkse, M. W., Uitto, P. M., Hilhorst, M. J., Ooms, B., and Heck, A. J. (2004).
   Selective isolation at the femtomole level of phosphopeptides from proteolytic digests using 2D-nanoLC-ESI-MS/MS and titanium oxide precolumns. *Anal. Chem.* 76, 3935-3943.
42. Rapid communications in mass spectrometry 18:3019 (2004) Isotope-coded N-terminal sulfonation of peptides allows quantitative proteomic analysis with increased de novo peptide sequencing capability.
   Rapid Communications in Mass Spectrometry Volume 18, Issue 24, Date: 30 Dec. 2004, Pages: 3019-3027 Yong Ho Lee, Hoon Han, Seok-Bok Chang, Sang-Won Lee.
43. Analytical Chemistry 68: 3413 (1996) Phosphopeptide Analysis by Matrix-Assisted Laser Desorption Time-of-Flight Mass Spectrometry Annan, R. S.; Carr, S. A. *Anal. Chem.*; (Article); 1996; 68(19); 3413-3421.
44. Larsen, M. R., Cordwell, S. J., and Roepstorff, P. (2002) Graphite powder as an alternative or supplement to reversed-phase material for desalting and concentration of peptide mixtures prior to matrix-assisted laser desorption/ionization-mass spectrometry. *Proteomics* 2, 1277-1287.
45. Gobom, J., Nordhoff, E., Mirgorodskaya, E., Ekman, R., and Roepstorff, P. (1999) Sample purification and preparation technique based on nanoscale reversed-phase columns for the sensitive analysis of complex peptide mixtures by matrix-assisted laser desorption/ionization mass spectrometry. *J Mass Spectrom.* 34, 105-116.
46. Cole, A. R., Knebel, A., Morrice, N. A., Robertson, L. A., Irving, A. J., Connolly, C. N., and Sutherland, C. (2004) GSK-3 phosphorylation of the Alzheimer epitope within collapsin response mediator proteins regulates axon elongation in primary neurons. *J. Biol. Chem.* 279, 50176-50180.
47. Saha, A., Saha, N., Ji, L. N., Zhao, J., Gregan, F., Sajadi, S. A. A., Song, B., and Sigel, H. (1996) Stability of metal ion complexes formed with methyl phosphate and hydrogen phosphate. *J. Biol. Inorg. Chem.* 1, 231-238 48. Hart, S. R., Waterfield, M. D., Burlingame, A. L., and Cramer, R. (2002).
   Factors governing the solubilization of phosphopeptides retained on ferric NTA IMAC beads and their analysis by MALDI TOFMS. *J. Am. Soc Mass Spectrom.* 13, 1042-1051.
49. Dobson, K. D., and McQuillan, A. J. (2000) In situ infrared spectroscopic analysis of the adsorption of aromatic carboxylic acids to TiO2, ZrO2, Al2O3, and Ta2O5 from aqueous solutions. *Spectrochim. Acta Part A Mol. Biomol. Spectrosc.* 56, 557-565.
50. Connor, P. A., and McQuillan, A. J. (1999) Phosphate adsorption onto TiO2 from aqueous solutions: an in situ internal reflection infrared spectroscopic study. *Langmuir* 15, 2916-2921.
51. Tunesi, S., and Anderson, M. (1991) Influence of chemisorption on the photodecomposition of salicylic acid and related compounds using suspended TiO2 ceramic membranes. *J. Phys. Chem.* 95, 3399-3405.
52. Garrone, E., Bolis, V., Fubini, B., and Morterra, C. (1989) Thermodynamic and spectroscopic characterization of heterogeneity among adsorption sites-Co on anatase at ambient temperature. *Langmuir* 5, 892-899.
53. Nilsson, A.; Stys, D.; Drakenberg, T.; Spangfort, M. D.; Forsen, S.; Allen, J. F. *J. Biol. Chem.* 1997, 272, 18350-18357.
   Anders Nilsson, Dalibor Stys, Torbjörn Drakenberg, Michael D. Spangfort, Sture Forsén, and John F. Allen, Phosphorylation Controls the Three-dimensional Structure of Plant Light Harvesting Complex II J. Biol. Chem., July 1997; 272: 18350.
54. Barber, J. *Biochim. Biophys. Acta* 1998, 1365, 269-277. Barber J title Photosystem two. BIOCHIMICA ET BIOPHYSICA ACTA-BIOENERGETICS 1365 (1-2): 269-277 Jun. 10 1998.
55. Anderson, J. M.; Boardman, N. K. *Biochim. Biophys. Acta* 1966, 112, 403-410. ANDERSON J M, BOARDMAN N K title: FRACTIONATION OF PHOTOCHEMICAL SYSTEMS OF PHOTOSYNTHESIS .I. CHLOROPHYLL CONTENTS AND PHOTOCHEMICAL ACTIVITIES OF PARTICLES ISOLATED FROM SPINACH CHLOROPLASTS BIOCHIMICA ET BIOPHYSICA ACTA 112 (3): 403& 1.
56, Carlberg, I.; Andersson, B. *Photosynth. Res.* 1996, 47, 145-156. Carlberg I, Andersson B title: Phosphatase activities in spinach thylakoid membranes—Effectors, regulation and location, PHOTOSYNTHESIS RESEARCH 47 (2): 145-156 FEB 199.
57, Melis, A. *Trends Plant Sci.* 1999, 4, 130-135. Melis A title: Photosystem-II damage and repair cycle in chloroplasts: what modulates the rate of photodamage in vivo? TRENDS IN PLANT SCIENCE 4 (4): 130-135 APR 1999

TABLE 1

| Peptide sequence | SEQ ID No. | Number of phosphate groups | $(M + H)^+$ Da |
|---|---|---|---|
| EVVGSAEAGVDAA (Ov. 340-352)*[1] | 17 | 1 | 1254.52 |
| EQLSTSEENSK (α-S2. 141-151) | 18 | 1 | 1331.53 |
| EQLSTSEENSK (α-S2. 141-151) | 19 | 2 | 1411.50 |
| TVDMESTEVFTK (α-S2. 153-164) | 20 | 1 | 1466.61 |
| TVDMESTEVFTKK (α-S2. 153-165) | 21 | 1 | 1594.70 |
| VPQLEIVPNSAEER (α-S1. 121-134) | 22 | 1 | 1660.79 |
| YLGEYLIVPNSAEER (α-S1)*[2] | 23 | 1 | 1832.83 |
| DIGSESTEDQAMEDIK (α-S1. 58-73) | 24 | 1 | 1847.69 |
| DIGSESTEDQAMEDIK (α-S1. 58-73) | 24 | 2 | 1927.69 |
| YKVPQLEIVPNSAEER (α-S1. 119-134) | 25 | 1 | 1951.95 |
| FQSEEQQQTEDELQDK (β-C. 33-48) | 26 | 1 | 2061.83 |
| EVVGSAEAGVDAASVSEEFR (Ov. 340-359) | 27 | 1 | 2088.89 |
| NVPGEIVESLSSSEESITR (β-C. 7-25)*[3] | 28 | 4 | 2352.85 |
| NTMEHVSSSEESIISQETYK (α-S2. 17-36) | 29 | 4 | 2619.04 |
| VNELSKDIGSESTEDQAMEDIK (α-S1. 52-73) | 30 | 3 | 2678.01 |

TABLE 1-continued

| Peptide sequence | SEQ ID No. | Number of phosphate groups | (M + H)+ Da |
|---|---|---|---|
| QMEAESISSSEEIVPNSVEAQK (α-S1. 74-94) | 31 | 5 | 2720.91 |
| NTMEHVSSSEESIISQETYKQ (α-S2. 17-37) *4 | 32 | 4 | 2747.10 |
| EKVNELSKDIGSESTEDQAMEDIK (α-S1. 50-73) | 33 | 3 | 2935.15 |
| ELEELNVPGEIVESLSSSEESITR (β-C. 17-40) | 34 | 4 | 2966.16 |
| NANEEEYSIGSSSEESAEVATEEVK (α-S2. 61-85) | 35 | 4 | 3008.01 |
| NANEEEYSIGSSSEESAEVATEEVK (α-S2. 61-85) | 35 | 5 | 3087.99 |
| RELEELNVPGEIVESLSSSEESITR (β-C. 16-40) | 36 | 4 | 3122.27 |
| KNTMEHVSSSEESIISQETYKQEK (α-S2. 16-39) *3 | 37 | 4 | 3132.20 |

Table 1 Overview of observed phosphorylated peptides derived by tryptic digestion of ovalbumin (Ov.), alpha casein S1 (α-S1) and S2 (α-S2) and beta casein (β-C.). The phosphorylation sites are underlined.
*1 Unusual cleavage (sequence was verified by MALDI tandem MS).
*2 The peptide signal at m/z 1832.8 represents a new sequence variant of the alpha-S1 casein in the region 104-119, corresponding to the sequence YLGEYLIVPNpSAEER, in contrast to the published sequence 104-YKVPQLEIVPNpSAEER-119 (SEQ ID NO. 38). This sequence could originate from an alternative splicing. The sequence was verified by MALDI tandem MS.
*3 Chymotryptic cleavage (sequence was verified by MALDI tandem MS).
*4 Sequence partly verified by MALDI tandem MS. Trypsin indicates K instead of Q in the C-terminal.

What is claimed:

1. A method for isolation of peptides comprising the steps of
    loading a solution containing one or more peptides onto titanium dioxide or zirconium dioxide stationary phase material wherein said solution is acidic and comprises at least 20% organic phase and one member selected from the group consisting of (a) at least about 6.5 mM of substituted aromatic carboxylic acid, and (b) at least about 11 mM of short chain, non-aromatic, hydroxylated carboxylic acid; and
    eluting proteins from said stationary phase material with an alkaline solution having pH of at least 9.0.

2. A method for isolation of peptides according to claim 1, wherein said peptides loaded onto said stationary phase material are
    sialylated peptides and wherein said solution is acidic and comprises at least 20% organic phase and at least about 6.5 mM of substituted aromatic carboxylic acid.

3. A method for isolation of peptides according to claim 1, wherein said peptides loaded onto said stationary phase material are
    sialylated peptides and wherein said solution is acidic and comprises at least 20% organic phase and at least about 11 mM of short chain, non-aromatic, hydroxylated carboxylic acid.

4. A method for isolation of peptides according to claim 1, wherein said peptides loaded onto said stationary phase material are
    phosphorylated peptides and wherein said solution is acidic and comprises at least 20% organic phase and at least about 6.5 mM of substituted aromatic carboxylic acid.

5. The method of claim 2, 3 or 4 further comprising the steps of characterizing isolated peptides by mass spectrometry.

6. The method of claim 2 or 4 wherein substituted aromatic carboxylic acid is any one or more of 2,5-di-hydroxy benzoic acid (DHB), phthalic acid or salicylic acid.

7. The method of claim 3 wherein short chain, non-aromatic, hydroxylated carboxylic is any one or more of lactic acid, glycolic acid, beta-hydroxy proprionic acid, or citric acid.

8. The method of claim 2, 3 or 4 wherein the alkaline solution has pH at least 10.5.

9. The method of claim 2, 3, or 4 wherein the peptides comprise fragments of larger proteins.

10. The method of claim 2, 3, or 4 wherein the solution is obtained from a tissue sample.

11. The method of claim 10 wherein the tissue sample is a biopsy.

12. The method of claim 2, 3, or 4 wherein the solution is obtained from a bodily fluid sample.

13. The method of claim 2, 3, or 4 wherein the solution is obtained from a cell culture.

14. The method of claim 2, 3 or 4 wherein the sample solution comprises proteins subject to one or more pre-treatments involving enzymatic modification.

15. The method of claim 2, 3 or 4 wherein a solution comprising or derived from the eluate is subject to one or more treatments involving enzymatic modification of proteins.

16. The method of claim 14 wherein the treatment or pre-treatment comprises digestion with one or more proteolytic enzymes.

17. The method of claim 15 wherein the treatment or pre-treatment comprises digestion with one or more proteolytic enzymes.

18. The method of claim 14 wherein the treatment or pre-treatment comprises digestion with one or more phosphatase enzymes.

19. The method of claim 15 wherein the treatment or pre-treatment comprises digestion with one or more phosphatase enzymes.

20. The method of claim 14 wherein the treatment or pre-treatment comprises digestion with one or more glycosidase enzymes.

21. The method of claim 15 wherein the treatment or pre-treatment comprises digestion with one or more glycosidase enzymes.

22. The method of claim 2, 3 or 4 wherein the sample solution comprises proteins subject to one or more pre-treatments whereby proteins are mass-modified with isotopic labels.

23. The method of claim 22 wherein one of the one or more isotopic labels is $O^{18}$.

24. The method of claim 2, 3 or 4 wherein a solution comprising or derived from the eluate is subject to one or more treatments whereby proteins are mass-modified with one or more isotopic labels.

25. The method of claim 24 wherein one of the one or more isotopic labels is $O^{18}$.

* * * * *

SEQUENCE LISTING

<160> NUMBER OF SEQ ID NOS: 38

<210> SEQ ID NO 1
<211> LENGTH: 13
<212> TYPE: PRT
<213> ORGANISM: Homo sapiens

<400> SEQUENCE: 1

Leu Val Pro Val Pro Ile Thr Asn Ala Thr Leu Asp Arg
1               5                   10

<210> SEQ ID NO 2
<211> LENGTH: 13
<212> TYPE: PRT
<213> ORGANISM: Prunus persica

<400> SEQUENCE: 2

Asn Val Ser Ser Gly Ser Pro Trp Tyr Gly Pro Asp Arg
1               5                   10

<210> SEQ ID NO 3
<211> LENGTH: 13
<212> TYPE: PRT
<213> ORGANISM: Spinacia oleracea

<400> SEQUENCE: 3

Thr Val Gln Ser Ser Ser Pro Trp Tyr Gly Pro Asp Arg
1               5                   10

<210> SEQ ID NO 4
<211> LENGTH: 19
<212> TYPE: PRT
<213> ORGANISM: Spinacia oleracea

<400> SEQUENCE: 4

Ser Ala Gly Lys Pro Lys Asn Val Ser Ser Gly Ser Pro Trp Tyr Gly
1               5                   10                  15

Pro Asp Arg

<210> SEQ ID NO 5
<211> LENGTH: 19

```
<212> TYPE: PRT
<213> ORGANISM: Spinacia oleracea

<400> SEQUENCE: 5

Thr Ala Gly Lys Pro Lys Thr Val Gln Ser Ser Pro Trp Tyr Gly
1               5                   10                  15

Pro Asp Arg

<210> SEQ ID NO 6
<211> LENGTH: 19
<212> TYPE: PRT
<213> ORGANISM: Spinacia oleracea

<400> SEQUENCE: 6

Thr Ala Gly Lys Pro Lys Asn Val Ser Ser Gly Ser Pro Trp Tyr Gly
1               5                   10                  15

Pro Asp Arg

<210> SEQ ID NO 7
<211> LENGTH: 13
<212> TYPE: PRT
<213> ORGANISM: Spinacia oleracea

<400> SEQUENCE: 7

Thr Val Gln Ser Ser Ser Pro Trp Tyr Gly Pro Asp Arg
1               5                   10

<210> SEQ ID NO 8
<211> LENGTH: 13
<212> TYPE: PRT
<213> ORGANISM: Spinacia oleracea

<400> SEQUENCE: 8

Asn Val Ser Ser Gly Ser Pro Trp Tyr Gly Pro Asp Arg
1               5                   10

<210> SEQ ID NO 9
<211> LENGTH: 14
<212> TYPE: PRT
<213> ORGANISM: Spinacia oleracea

<400> SEQUENCE: 9

Ser Pro Thr Gly Glu Val Ile Phe Gly Gly Glu Thr Met Arg
1               5                   10

<210> SEQ ID NO 10
<211> LENGTH: 12
<212> TYPE: PRT
<213> ORGANISM: Spinacia oleracea

<400> SEQUENCE: 10

Thr Leu Phe Asn Gly Thr Leu Thr Leu Ala Gly Arg
1               5                   10

<210> SEQ ID NO 11
<211> LENGTH: 6
<212> TYPE: PRT
<213> ORGANISM: Spinacia oleracea

<400> SEQUENCE: 11

Thr Leu Phe Asn Gly Leu
1               5

<210> SEQ ID NO 12
```

```
<211> LENGTH: 15
<212> TYPE: PRT
<213> ORGANISM: Spinacia oleracea

<400> SEQUENCE: 12

Asn Gly Leu Thr Leu Ala Gly Arg Asp Gln Glu Thr Thr Gly Phe
1               5                   10                  15

<210> SEQ ID NO 13
<211> LENGTH: 13
<212> TYPE: PRT
<213> ORGANISM: Spinacia oleracea

<400> SEQUENCE: 13

Ala Thr Ile Pro Ala Asp Asn Val Pro Asp Met Gln Lys
1               5                   10

<210> SEQ ID NO 14
<211> LENGTH: 12
<212> TYPE: PRT
<213> ORGANISM: Spinacia oleracea

<400> SEQUENCE: 14

Ile Gly Gly Ile Trp Thr Trp Val Gly Thr Asn Lys
1               5                   10

<210> SEQ ID NO 15
<211> LENGTH: 16
<212> TYPE: PRT
<213> ORGANISM: Spinacia oleracea

<400> SEQUENCE: 15

Phe Asn Pro Gly Ala Glu Ser Val Val Leu Ser Asn Ser Thr Leu Lys
1               5                   10                  15

<210> SEQ ID NO 16
<211> LENGTH: 14
<212> TYPE: PRT
<213> ORGANISM: Spinacia oleracea

<400> SEQUENCE: 16

Ala Thr Ser Pro Ala Asp Asn Val Pro Asp Met Gln Lys Arg
1               5                   10

<210> SEQ ID NO 17
<211> LENGTH: 13
<212> TYPE: PRT
<213> ORGANISM: Gallus gallus

<400> SEQUENCE: 17

Glu Val Val Gly Ser Ala Glu Ala Gly Val Asp Ala Ala
1               5                   10

<210> SEQ ID NO 18
<211> LENGTH: 11
<212> TYPE: PRT
<213> ORGANISM: Bos taurus

<400> SEQUENCE: 18

Glu Gln Leu Ser Thr Ser Glu Glu Asn Ser Lys
1               5                   10

<210> SEQ ID NO 19
<211> LENGTH: 11
<212> TYPE: PRT
<213> ORGANISM: Bos taurus
```

<400> SEQUENCE: 19

Glu Gln Leu Ser Thr Ser Glu Glu Asn Ser Lys
1               5                   10

<210> SEQ ID NO 20
<211> LENGTH: 12
<212> TYPE: PRT
<213> ORGANISM: Bos taurus

<400> SEQUENCE: 20

Thr Val Asp Met Glu Ser Thr Glu Val Phe Thr Lys
1               5                   10

<210> SEQ ID NO 21
<211> LENGTH: 13
<212> TYPE: PRT
<213> ORGANISM: Bos taurus

<400> SEQUENCE: 21

Thr Val Asp Met Glu Ser Thr Glu Val Phe Thr Lys Lys
1               5                   10

<210> SEQ ID NO 22
<211> LENGTH: 14
<212> TYPE: PRT
<213> ORGANISM: Bos taurus

<400> SEQUENCE: 22

Val Pro Gln Leu Glu Ile Val Pro Asn Ser Ala Glu Glu Arg
1               5                   10

<210> SEQ ID NO 23
<211> LENGTH: 15
<212> TYPE: PRT
<213> ORGANISM: Bos taurus

<400> SEQUENCE: 23

Tyr Leu Gly Glu Tyr Leu Ile Val Pro Asn Ser Ala Glu Glu Arg
1               5                   10                  15

<210> SEQ ID NO 24
<211> LENGTH: 16
<212> TYPE: PRT
<213> ORGANISM: Bos taurus

<400> SEQUENCE: 24

Asp Ile Gly Ser Glu Ser Thr Glu Asp Gln Ala Met Glu Asp Ile Lys
1               5                   10                  15

<210> SEQ ID NO 25
<211> LENGTH: 16
<212> TYPE: PRT
<213> ORGANISM: Bos taurus

<400> SEQUENCE: 25

Tyr Lys Val Pro Gln Leu Glu Ile Val Pro Asn Ser Ala Glu Glu Arg
1               5                   10                  15

<210> SEQ ID NO 26
<211> LENGTH: 16
<212> TYPE: PRT
<213> ORGANISM: Bos taurus

<400> SEQUENCE: 26

```
Phe Gln Ser Glu Glu Gln Gln Thr Glu Asp Glu Leu Gln Asp Lys
1               5                   10                  15
```

<210> SEQ ID NO 27
<211> LENGTH: 20
<212> TYPE: PRT
<213> ORGANISM: Gallus gallus

<400> SEQUENCE: 27

```
Glu Val Val Gly Ser Ala Glu Ala Gly Val Asp Ala Ala Ser Val Ser
1               5                   10                  15

Glu Glu Phe Arg
            20
```

<210> SEQ ID NO 28
<211> LENGTH: 19
<212> TYPE: PRT
<213> ORGANISM: Bos taurus

<400> SEQUENCE: 28

```
Asn Val Pro Gly Glu Ile Val Glu Ser Leu Ser Ser Glu Glu Ser
1               5                   10                  15

Ile Thr Arg
```

<210> SEQ ID NO 29
<211> LENGTH: 20
<212> TYPE: PRT
<213> ORGANISM: Bos taurus

<400> SEQUENCE: 29

```
Asn Thr Met Glu His Val Ser Ser Ser Glu Glu Ser Ile Ile Ser Gln
1               5                   10                  15

Glu Thr Tyr Lys
            20
```

<210> SEQ ID NO 30
<211> LENGTH: 22
<212> TYPE: PRT
<213> ORGANISM: Bos taurus

<400> SEQUENCE: 30

```
Val Asn Glu Leu Ser Lys Asp Ile Gly Ser Glu Ser Thr Glu Asp Gln
1               5                   10                  15

Ala Met Glu Asp Ile Lys
            20
```

<210> SEQ ID NO 31
<211> LENGTH: 22
<212> TYPE: PRT
<213> ORGANISM: Bos taurus

<400> SEQUENCE: 31

```
Gln Met Glu Ala Glu Ser Ile Ser Ser Ser Glu Glu Ile Val Pro Asn
1               5                   10                  15

Ser Val Glu Ala Gln Lys
            20
```

<210> SEQ ID NO 32
<211> LENGTH: 21
<212> TYPE: PRT
<213> ORGANISM: Bos taurus

<400> SEQUENCE: 32

```
Asn Thr Met Glu His Val Ser Ser Glu Ser Ile Ile Ser Gln
1               5                   10                  15

Glu Thr Tyr Lys Gln
            20

<210> SEQ ID NO 33
<211> LENGTH: 24
<212> TYPE: PRT
<213> ORGANISM: Bos taurus

<400> SEQUENCE: 33

Glu Lys Val Asn Glu Leu Ser Lys Asp Ile Gly Ser Glu Ser Thr Glu
1               5                   10                  15

Asp Gln Ala Met Glu Asp Ile Lys
            20

<210> SEQ ID NO 34
<211> LENGTH: 24
<212> TYPE: PRT
<213> ORGANISM: Bos taurus

<400> SEQUENCE: 34

Glu Leu Glu Glu Leu Asn Val Pro Gly Glu Ile Val Glu Ser Leu Ser
1               5                   10                  15

Ser Ser Glu Glu Ser Ile Thr Arg
            20

<210> SEQ ID NO 35
<211> LENGTH: 25
<212> TYPE: PRT
<213> ORGANISM: Bos taurus

<400> SEQUENCE: 35

Asn Ala Asn Glu Glu Glu Tyr Ser Ile Gly Ser Ser Ser Glu Glu Ser
1               5                   10                  15

Ala Glu Val Ala Thr Glu Glu Val Lys
            20                  25

<210> SEQ ID NO 36
<211> LENGTH: 25
<212> TYPE: PRT
<213> ORGANISM: Bos taurus

<400> SEQUENCE: 36

Arg Glu Leu Glu Glu Leu Asn Val Pro Gly Glu Ile Val Glu Ser Leu
1               5                   10                  15

Ser Ser Ser Glu Glu Ser Ile Thr Arg
            20                  25

<210> SEQ ID NO 37
<211> LENGTH: 24
<212> TYPE: PRT
<213> ORGANISM: Bos taurus

<400> SEQUENCE: 37

Lys Asn Thr Met Glu His Val Ser Ser Glu Ser Ile Ile Ser
1               5                   10                  15

Gln Glu Thr Tyr Lys Gln Glu Lys
            20

<210> SEQ ID NO 38
<211> LENGTH: 16
<212> TYPE: PRT
```

```
<213> ORGANISM: Bos taurus

<400> SEQUENCE: 38

Tyr Lys Val Pro Gln Leu Glu Ile Val Pro Asn Ser Ala Glu Glu Arg
1               5                   10                  15
```